US008183023B2

(12) United States Patent
Peters et al.

(10) Patent No.: US 8,183,023 B2
(45) Date of Patent: May 22, 2012

(54) *THERMUS EGERTSSONII* DNA POLYMERASES

(75) Inventors: Lars-Erik Peters, Lafayette, CO (US); Nan Fang, Neuss (DE)

(73) Assignee: QIAGEN GmbH (DE)

( * ) Notice: Subject to any disclaimer, the term of this patent is extended or adjusted under 35 U.S.C. 154(b) by 364 days.

(21) Appl. No.: 12/442,600

(22) PCT Filed: Oct. 9, 2007

(86) PCT No.: PCT/EP2007/060724
§ 371 (c)(1),
(2), (4) Date: Sep. 8, 2009

(87) PCT Pub. No.: WO2008/043765
PCT Pub. Date: Apr. 7, 2008

(65) Prior Publication Data
US 2009/0317888 A1 Dec. 24, 2009

(30) Foreign Application Priority Data
Oct. 9, 2006 (EP) .................................. 06021140

(51) Int. Cl.
*C12N 9/00* (2006.01)
*C12N 15/00* (2006.01)
(52) U.S. Cl. ...................... 435/183; 435/320.1; 435/975
(58) Field of Classification Search .................... None
See application file for complete search history.

(56) References Cited

U.S. PATENT DOCUMENTS

| | | | |
|---|---|---|---|
| 4,179,337 A | 12/1979 | Davis et al. |
| 4,301,144 A | 11/1981 | Iwashita et al. |
| 4,458,006 A | 7/1984 | Donges et al. |
| 4,469,863 A | 9/1984 | Ts'o et al. |
| 4,496,689 A | 1/1985 | Mitra |
| 4,640,835 A | 2/1987 | Shimizu et al. |
| 4,670,417 A | 6/1987 | Iwasaki et al. |
| 4,683,195 A | 7/1987 | Mullis et al. |
| 4,683,202 A | 7/1987 | Mullis |
| 4,791,192 A | 12/1988 | Nakagawa et al. |
| 4,962,020 A | 10/1990 | Tabor et al. |
| 4,962,022 A | 10/1990 | Fleming et al. |
| 5,034,506 A | 7/1991 | Summerton et al. |
| 5,216,141 A | 6/1993 | Benner |
| 5,235,033 A | 8/1993 | Summerton et al. |
| 5,386,023 A | 1/1995 | Sanghvi et al. |
| 5,409,818 A | 4/1995 | Davey et al. |
| 5,436,149 A | 7/1995 | Barnes |
| 5,455,166 A | 10/1995 | Walker |
| 5,498,523 A | 3/1996 | Tabor et al. |
| 5,602,240 A | 2/1997 | Mesmaeker et al. |
| 5,614,365 A | 3/1997 | Tabor et al. |
| 5,637,684 A | 6/1997 | Cook et al. |
| 5,644,048 A | 7/1997 | Yau |
| 5,804,375 A | 9/1998 | Gelfand et al. |
| 6,001,645 A | 12/1999 | Slater et al. |
| 6,077,664 A | 6/2000 | Slater et al. |
| 6,875,573 B2 * | 4/2005 | Fuller et al. .................. 435/91.2 |
| 6,946,273 B1 | 9/2005 | Sorge et al. |
| 2003/0198978 A1 | 10/2003 | Rozzelle et al. |
| 2004/0025205 A1 * | 2/2004 | Spangenberg et al. ....... 800/287 |

FOREIGN PATENT DOCUMENTS

| | | |
|---|---|---|
| WO | WO/92/03566 | 3/1992 |
| WO | WO 03/004632 A2 | 1/2003 |
| WO | WO 03004632 A2 * | 1/2003 |
| WO | WO 03/023029 | 3/2003 |
| WO | WO 03/048308 A2 | 6/2003 |
| WO | WO 2006/030455 A | 3/2006 |

OTHER PUBLICATIONS

Altschul et al., "Gapped BLAST and PSI-BLAST: A New Generation of Protein Database Search Programs". Nucleic Acids Res. 25:3389-3402 (1997).
Altschul et al., "Local Alignment Statistics". Methods in Enzymology, 266: 460-480 (1996).
Altschul et at, "Basic Local Alignment Search Tool". J. Mol. Biol. 215, 403-410, (1990).
Barnes, W.M., "PCR Amplification of Up to 35-Kb DNA With High Fidelity and High Yield From a Bacteriophage Templates". Proc. Natl. Acad. Sci. USA, 1:2216-2220 (1994).
Beaucage et al., "Deoxynucleoside Phosphoramidites—A New Class of Key Intermediates for Deoxypolynucleotide Synthesis". Tetrahedron Letters, 22:1859-1862 (1981).
Beaucage, et al., "The Functionalization of Oligonucleotides Via Phosphoramidite Derivatives" Tetrahedron, 49(10):1925 (1993).
Black, "Microbiology Principles and Applications", 2d edition, Prentice Hall, New Jersey, 145-146, 1991.
Bolli, et al., "Bicyclo DNA Synthesis, Characterization, and Pairing Properties of a DNA Analogues With Restricted Conformational Flexibility in the Sugar Phosphate Backbone". American Chemical Society 7:100-117 (1994).
Brill, et al., "Synthesis of Oligodeoxynucleoside Phosphorodithioates Via Thioamidites" J. Am. Chem. Soc., 111:2321 (1989).
Caetano-Anolles et al., "DNA Amplification fingerprinting using very short arbitrary oligonucleotide primers". Bic/Technology, 9:553-557, (1991).
Caetano-Anolles, Scanning of Nucleic Acids by In Vivo Amplification: New Developments and Applications. Nat. Biotechnol. 14 (1996) 1668-1674.
Carlsson, et aL, "Screening for Genetic Mutations". Nature, 380:207 (1996).
Caruthers et al., "New Chemical Methods for Synthesizing Polynucleotides". Nuc. Acids Res. Symp. Ser., 7:215-233, 1980.
Chapters 2 and 3, ASC Symposium Series 580, "Carbohydrate Modifications in Antisense Research", Ed. Y.S. Sanghui and P. Dan Cook, Date: 1994.

(Continued)

*Primary Examiner* — Christopher M. Babic
(74) *Attorney, Agent, or Firm* — Ballard Spahr LLP

(57) ABSTRACT

The present invention relates to a thermophilic polymerase, wherein the DNA polymerase has an in-vitro primer extension rate that is >35 bases/second and faster relative to the primer extension rate of a DNA polymerase comprising amino acid sequences SEQ ID NO: 2 or 4, when measured under identical conditions in a DNA replication assay using primed single strand M13mp18 DNA and an incubation temperature of 60° C. The invention also relates to a vector comprising the polymerase, a host cell comprising the vector. The invention relates to a nucleic acid replication kit comprising the polymerase according to the invention.

12 Claims, 33 Drawing Sheets

OTHER PUBLICATIONS

Chapters 6 and 7, ASC Symposium Series 580, "Carbohydrate Modifications in Antisense Research", Ed. Y.S. Sanghui and P. Dan Cook, Date: 1994.

Cheng, S., et al., "Effective Amplification of Long Targets from Cloned Inserts and Human Genomic DNA," Proc. Natl. Acad. Sci. USA, 91(12):5695-5699 (1994).

Chow and Kempe, "Synthesis of Oligodeoxyribonucleotides on Silica Gel Support". Nuc. Acids Res., 9:2807-2817, (1981).

Crea and Horn, "Synthesis of Oligonucleotides on Cellulose by a Phosphotriester Method". Nuc. Acids Res., 9:2331, 1980.

Creighton, T.E., "Proteins: Structure and Molecular Properties", W.H. Freeman & Co., San Francisco, pp. 79-86 (1983).

Davies et al., "Long Range PCR". Methods Mol Biol. 2002;187: 51-5.

Dempcy, et al, "Synthesis of a Thymidyl Pentamer of Deoxyribonucleic Guanidine and Binding Studies With DNA Homopolynucleotides". Proc. Natl. Acad. Sci. USA, 92:6097 (1995).

Devereux et al., "A Comprehensive Set of Sequence Analysis Programs for the VAX". Nucl. Acid Res. 12:387-395 (1984).

Echols and Goodman, "Fidelity Mechanisms in DNA Replication," Annual Review of Biochemistry, 60:477-511, 1991.

Eckert, K. "DNA Polymerase Fidelity and the Polymerase Chain Reaction". PCR Methods and Applications, 1:17-24, (1991).

Egholm, et al., "Peptide Nucleic Acids(PNA). Oligonucleotide Analogues With an Achiral Peptide Backbone". J. Am. Chem. Soc., 114:1895 (1992).

Egholm, et al., "PNA Hybridizes to Complementary Oligonucleotides Obeying the Watson-Crick Hydrogen Bonding Rules". Nature, 365:566 (Oct. 7, 1993).

Evan et al., "Isolation of Monoclonal Antibodies Specific for Human c-myc Proto-Oncogene Product. Molecular and Cellular Biology", 5:3610-3616 (1985).

FAQ sheet for Wayne Barnes' thermostable enzymes http://biochem.wustl.edu/~barnes/faq.wpa/, Date: Oct. 27, 2005.

Feng & Doolittle, "Progressice Sequence Alignment As a Prerequisite to Correct Phylogenetic Trees". J. Mol. Evol. 35:351-360 (1987).

Field et al., "Purification of a Ras-Responsive Adenylyl Cyclase Complex From *Saccharomyces cerevisiae* by Use of an Epitope Addition Method". Molecular and Cellular Biology 8:2159-2165 (1988).

Gao, et al, "Unusual Conformation of A 3-Thioformecetal Linkage in a DNA Duplex". J. Biomolecular NMR, 34:17 (1994).

George et al., "Current Methods in Sequence Comparison and Analysis". Macromolecule Sequencing and Synthesis, Selected Methods and Applications, pp. 20127-20149 (1988), Alan R. Liss, Inc.

Heath, D.D., et al., "PCR Primed With VNTR Core Sequences Yields Species Specific Patterns and Hypervariable Probes". Nucl. Acids Res., 21(24): 5782-5785, (1993).

Higgins & Sharp., "Fast and Sensitive Multiple Sequence Alignments on a Microcomputer". CABIOS 5:151-153 (1989).

Hopp et al., "A Short Polypeptide Marker Sequence Useful for Recombinant Protein Identification and Purification," BioTechnology, 6:1204-1210 (1988).

Horn et al, Tetrahedron Lett., "Oligonucleotides with Alternating Anionic and Cationic Phosphoramidate Linkages: Synthesis and Hybridization of Stereo-uniform Isomers" 37:743 (1996).

Huang, M., et al., "Extension of Base Mispairs by Taq DNA Polymerase: Implications for Single Nucleotide Discrimination in PCR". Nucleic Acids Research 20:17 4567-4573 (1992).

Jenkins, et al., Chem. Soc. Rev., (1995)pp. 169-176.

Joyce et al., "Function and Structure Relationships in DNA Polymerases". Annu. Rev. Biochem. 63 (1994) 777-822.

Jung, et al., "Hybridization of Alternating Cationic/Anionic Oligonucleotides to RNA Segments", Nucleoside & Nucleotide, 13:1597 (1994).

Karlin et at, "Applications and Statistics for Multiple High Scoring Segments in Molecular Sequences" PNAS USA 90:5873-5787 (1993).

Kiedrowski, et al., "Parabolic Growth of a Self Replication Hexadeoxynucleotide Bearing a 3'5' Phosphoamidate Linkage". Angew. Chem. Intl. Ed. English, 30:423 (1991).

Letsinger, "Phosphoramidate Analogs of Oligonucleotides" Org. Chem., 35:3800 (1970).

Letsinger, et al., "Cationic Oligonucleotides". J. Am. Chem. Soc., 110:4470 (1988).

Letsinger, et al., "Effects of Pendant Groups At Phosphorus on Binding Properties of D-Apa Analogues". Nucl. Acids Res., 14:3487 (1986).

Lin, J. J., et al., "A Novel PCR Based Assay for Plant and Bacterial DNA Fingerprinting". FOCUS, 17(2):66-70, (1995).

Lutz-Freyennuth et al., "Quantitative Determination That One of Two Potential RNA-Binding Domains of the A Protein Component of the U1 Small Nuclear Ribonucleoprotein Complex Binds With High Affinity to Stem-Loop II of U1 RNA". Proc. Natl. Acad. Sci. USA, 87:6393-6397 (1990).

Mag, et al., "Synthesis and Selective Cleavage of an Oligodeoxynucleotide Containing a Bridged Internucleotide 5'-Phosphorothioate Linkage". Nucleic Acids Res., 19:1437 (1991).

Martin et al., "GAP Domains Responsible for Ras-21 Dependent Inhibition of Muscarinic Atrial K+ Channel Currants". Science, 255:192-194 (1992).

Matteucci and Caruthers, "The Synthesis of Oligdeoxypyrimidines on a Polymer Support". Tetrahedron Lett., 21:719, 1980.

Meier, et al, "Peptide Nucleic Acids (Pnas) Unusual Properties of Nonionic Oligonucleotide Analogues". Chem. Int. Ed. Engl., 31:1008 (1992).

Mendelman, L., et al., "Nearest Neighbor Influences on DNA Polymerase Insertion Fidelity". 264:24 14415-14423, (1989).

Mesmaeker, et al, "Comparison and Rigid Flexible Backbones in Antisense Oligonuckeotides". Bioorganic & Medicinal Chem. Lett., 4:395 (1994).

Needleman & Wunsch, "A General Method Applicable to the Search for Similarities in the Amino Acid Sequence of Two Proteins". J. Mol. Biol. 48:443 (1970).

O'Donnell, "Accessory Proteins Bind a Primed Template and Mediate Rapid Cycling of DNA Polymerase III Holoenzyme From *Escherichia coli*". J. Biol. Chem. 262:16558-16565 (1987).

Paborsky et al., "Mammalian Cell Transient Expression of Tissue Factor for the Production of Antigen". Protein Engineering, 3(6):547-553 (1990).

Pauwels, et al., "Biological Activity of New 2-5A Analogues". Chemica Scripta, 26:141 (1986).

Pavlov A R et al: "Recent Developments in the Optimization of Thêrmostable DNA Polymerases for Efficient Applications" Trends in Biotechnology, Elsevier Publications, Cambridge, GB, vol. 22,No. 5, pp. 253-260, (2004) XP004504365 ISSN: 0167-7799.

Pearson & Lipman, "Improved Tools for Biological Sequence Comparison". PNAS USA 85:2444 (1988).

Radding, "Homologous Pairing and Strand Exchange in Genetic Recombination" Ann. Rev. Genetics, 16:405-37, Date: Oct. 27, 2005.

Rawls, "Optimistic About Antisense" C & E News, Jun. 2, 1997, p. 35.

Roberge et al., "A Strategy for a Convergent Synthesis of N Linked Glycopeptides on a Solid Support". Science 269:202-204, 1995.

Sanger, F., et al., "DNA Sequencing With Chain-Terminating Inhibitors". Proc. Natl. Acad. Sci. USA, 74:5463-5467 (1977).

Sanger, F., et al., "A Rapid Method for Determining Sequences in DNA by Primed Synthesis With DNA Polymerase" J. Mol. Biol., 94:444-448 (1975).

Sawai, et al., "Synthesis and Properties of Oligoadenylic Acids Containing 2'-5' Phosphoramide Linkage" Chem. Lett., 805 (1984).

Skinner et al., "Use of Glu Glu Phe C Terminal Epitope for Rapid Purification of the Catalytic Domain of Normal and Mutant Ras GTpase Activating Proteins" J. Biol. Chem., 266:15163-15166 (1991).

Smith & Waterman, "Comparison of Biosequences". Adv. Appl. Math. 2:482 (1981).

Sprinzl, et al., "Enzymatic Incorpororation of ATP and CTP Analogues Into the 3' End of tRNA". Eur. J. Biochem., 81:579 (1977).

Tabor, S., "Selective Inactivation of the Exonuclease Activity of Bacteriophage T7 DNA Polymerase by In Vitro Mutagenesis". Journal of Biological Chemistry, 264:11 6447-6458 (1999).

Tabor, S., Richardson, C.C., "A Single Residue and DNA Polymerase of the *Eschericia coil* DNA Polymerase I Family Is Critical for Distinguishing Between Deoxy- and Dideoxyriboncleotides", Proc. Natl. Acad. Sci. USA, Jul. 3, 1995, 92 (14): 6339-43.

Vos, P., et al., "AFLP: A New Technique for DNA Fingerprinting". Nucl. Acids Res., 23(21):4407-4414 (1995).

Welsh, J., et al., "Fingerprinting Genomes Using PCR With Arbitrary Primers". Nucl. Acids Res., 18(24):7213-7218 (1990).

Williams, J. G. K., et al., "DNA Polymorphisms Amplified by Arbitrary Primers Are Useful As Genetic Markers". Nucl. Acids Res., 18(22):65316535, (1990).

Yang Guangwei et al., "A Conserved Tyr Residue Is Required for Sugar Selectivity in a Pol Alpha DNA Polymerase" Biochemistry, vol. 41, No. 32, pp. 10256-10261, (2002), XP002413785 ISSN:0006-2960.

Yuzhakov et al., "Replisome Assembly Reveals the Basis for Asymmetric Function in Leading and Lagging Strand Replication" Cell 86:877-886 (1996).

* cited by examiner

Fig. 1

Enzyme Allele Frequencies within Lineages for Different Loci.

| Locus/ no. of alleles | Lineage[a] | | | | | |
|---|---|---|---|---|---|---|
| | T. brockianus | T. thermophilus | T. igniterrae | T. scotoductus | Teg | T. oshimai |
| Alkaline phosphatase | 1 | 1 | 5 | 4 | 2 | 2 |
| Aspartate aminotransferase | 4 | 4 | 6 | 4 | 2 | 2 |
| Esterase | 3 | 6 | 2 | 5 | 1 | 3 |
| Glucose-6-phosphate isomerase | 1 | 4 | 4 | 6 | 1 | 3 |
| Hexokinase | 2 | 1 | 2 | 4 | 2 | 1 |
| Isocitrate dehydrogenase | 2 | 1 | 1 | 4 | 1 | 1 |
| Malate dehydrogenase | 3 | 2 | 2 | 4 | 2 | 1 |
| Nucleoside phosphorylase | 3 | 4 | 3 | 8 | 1 | 3 |
| Superoxide dismutase | 1 | 1 | 1 | 5 | 1 | 2 |
| Unspecific dehydrogenase | 1 | 4 | 3 | 10 | 1 | 1 |
| Mean | 2.1 | 2.8 | 2.9 | 5.4 | 1.4 | 1.9 |

Fig. 2
Genetic Diversity within Lineages.

| Lineage[a] | No. of strains | No. of ETs | Polymorphic loci | Mean no. of alleles | ETs $H_T$ | Isolates $H_T$ |
|---|---|---|---|---|---|---|
| T. brockianus | 21 | 13 | 0.6 | 2.1 | 0.254 | 0.193 |
| T. thermophilus | 15 | 14 | 0.6 | 2.8 | 0.438 | 0.433 |
| T. igniterrae | 22 | 19 | 0.8 | 2.9 | 0.376 | 0.358 |
| T. scotoductus[b] | 30 | 24 | 1 | 5.4 | 0.583 | 0.55 |
| T. eggertssonii | 7 | 5 | 0.4 | 1.4 | 0.16 | 0.047 |
| T. oshimai | 6 | 6 | 0.6 | 1.9 | 0.293 | 0.293 |

*Thermus spec.* Dendrogram after MLEE Analysis

Fig. 4a

Percentage of Positive Phenotypic Tests for the Strain Lineages Derived from the MLEE Analysis.

| Phenotypic test | Lineage (no. analyzed) | | | | | | |
|---|---|---|---|---|---|---|---|
| | T. brockianus (10) | T. thermophilus (5) | T. igniterrae (9) | T. scotoductus (12) | Tegf(5) | T. oshimai (A) | |
| Acetate | 0 | 0 | 0 | 0 | 0 | 0 | |
| Arabinose | 10 | 0 | 0 | 7 | 40 | 0 | |
| Arginine | 100 | 60 | 44 | 93 | 100 | 75 | |
| Asparagine | 0 | 0 | 0 | 0 | 0 | 0 | |
| Aspartate | 0 | 0 | 0 | 0 | 0 | 0 | |
| Casein | 0 | 0 | 0 | 7 | 0 | 0 | |
| Citrate | 20 | 0 | 33 | 14 | 0 | 50 | |
| Formic acid | 100 | 80 | 44 | 71 | 100 | 75 | |
| Fructose | 0 | 0 | 0 | 0 | 0 | 0 | |
| Galactose | 50 | 100 | 33 | 100 | 100 | 100 | |
| Glutamate | 0 | 0 | 0 | 0 | 0 | 0 | |
| Glutamine | 30 | 100 | 33 | 29 | 80 | 50 | |
| Glucose | 63 | 60 | 44 | 79 | 80 | 75 | |
| Glycerol | 100 | 100 | 56 | 93 | 100 | 100 | |
| Histidine | 0 | 17 | 0 | 0 | 20 | 0 | |
| Alpha-ketoglutaric acid | 0 | 0 | 0 | 0 | 0 | 0 | |
| Lactose | 10 | 0 | 0 | 0 | 0 | 0 | |
| Leucine | 0 | 0 | 11 | 0 | 20 | 0 | |
| Lysine | 0 | 0 | 0 | 0 | 0 | 0 | |
| Malate | 20 | 0 | 33 | 9 | 40 | 25 | |
| Maltose | 10 | 0 | 0 | 0 | 40 | 0 | |
| Mineral | 0 | 0 | 0 | 0 | 0 | 0 | |
| Ornithine | 22 | 20 | 33 | 15 | 40 | 33 | |
| Proline | 100 | 60 | 33 | 62 | 100 | 100 | |
| Pyruvate | 56 | 50 | 38 | 14 | 80 | 75 | |
| Raffinose | 0 | 0 | 0 | 7 | 0 | 0 | |
| Rhamnose | 10 | 0 | 0 | 0 | 0 | 25 | |
| Serine | 0 | 0 | 0 | 0 | 0 | 0 | |

Fig. 4b

Percentage of Positive Phenotypic Tests for the Strain Lineages Derived from the MLEE Analysis

| Phenotypic test | T. brockianus (10) | T. thermophilus (5) | T. igniterrae (9) | T. scotoductus (12) | Teg (5) | T. oshimai (4) |
|---|---|---|---|---|---|---|
| Starch | 56 | 50 | 38 | 15 | 80 | 75 |
| Tartrate | 0 | 0 | 0 | 0 | 40 | 0 |
| Threonine | 22 | 20 | 33 | 15 | 40 | 33 |
| Valine | 10 | 0 | 0 | 0 | 0 | 25 |
| Xylose | 0 | 0 | 0 | 0 | 0 | 0 |
| Ampicillin | 0 | 0 | 0 | 0 | 0 | 0 |
| Penicillin-G | 0 | 0 | 0 | 0 | 0 | 0 |
| Nalidixic acid | 100 | 100 | 100 | 86 | 20 | 20 |
| Bacitracin | 0 | 0 | 0 | 0 | 0 | 0 |
| Streptomycin | 0 | 0 | 11 | 0 | 0 | 0 |
| Chloramphenicol | 0 | 0 | 22 | 0 | 0 | 0 |
| Vancomycin | 0 | 0 | 11 | 0 | 0 | 0 |
| Rifampicin | 100 | 100 | 100 | 100 | 100 | 100 |
| Gentamicin | 0 | 0 | 0 | 0 | 20 | 0 |
| Tetracyclin | 0 | 0 | 22 | 0 | 0 | 0 |
| Nitrate reduction | 43 | 33 | 95 | 18 | 43 | 50 |

Fig. 5

Ratio of Thiosulfate Oxidation within Lineages.

| Lineage | Number of strains analyzed | Thiosulfate-oxidation % |
|---|---|---|
| T. brockianus | 5 | 100 |
| T. thermophilus | 5 | 60 |
| T. igniterrae | 5 | 80 |
| T. scotoductus | 9 | 78 |
| T. eggertssonii. | 5 | 0 |
| T. oshimai | 4 | 100 |

Fig. 6

| Polymerase Gene | |
|---|---|
| Organism | NCBI Accession Number |
| T. aquaticus | D32013 |
| T. flavus | X66105 |
| T. filiformis | AF030320 |
| T. thermophilus | D28878 |

| 16S rRNA Gene | |
|---|---|
| Organism | NCBI Accession Number |
| T. aquaticus | L09663 |
| T. brockianus | Y18409 |
| T. flavus | L09660 |
| T. filiformis | L09667 |
| T. thermophilus | X07998 |
| T. antranikianus | Y18415 |
| T. igniterrae | Y18408 |
| T. oshimai | Y18416 |
| T. scotoductus | Y18410 |

Fig. 7a    16S rRNA Gene Sequence Alignment

Fig. 7b 16S rRNA Gene Sequence Alignment

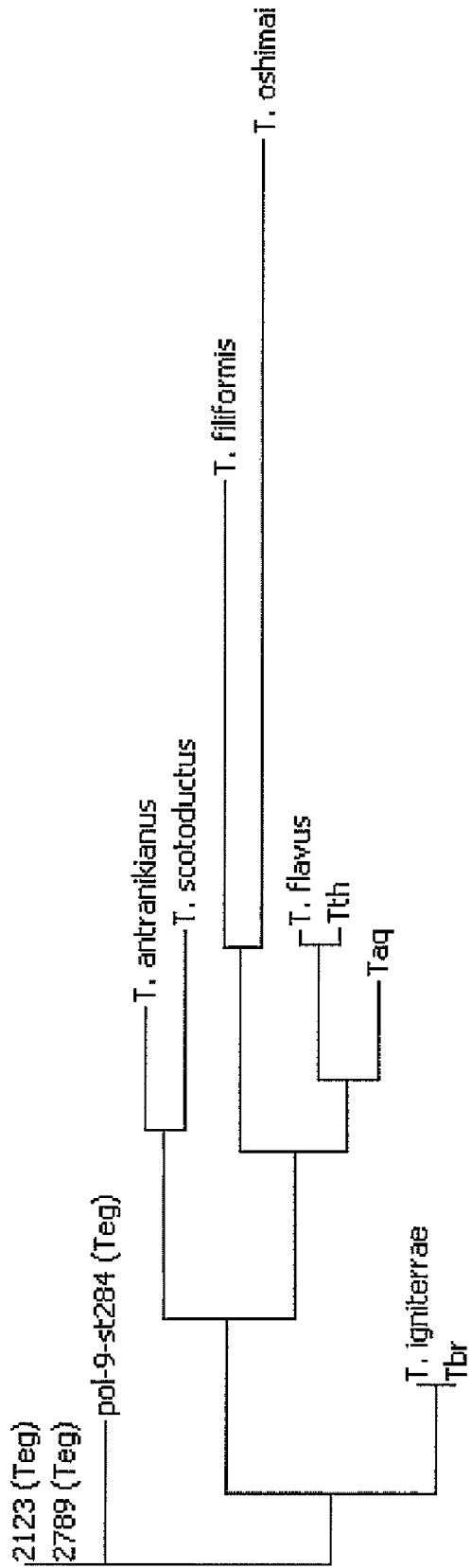
Fig. 8  Phylogentic Tree (16S rRNA)

Fig. 9 polA Gene (Conserved Core Region) Sequence Alignment

| | | |
|---|---|---|
| 2123 (Teg) Pol | 1 | ELRVLAHLSGDENLIQVFQEGRDIHTQTASUMFGLPAEAIDPLMRRAAKTINFGVLYGMSAHRLSQELSIPYEEAVAFI |
| 2124 (Teg) Pol | 1 | ELRVLAHLSGDENLIQVFQEGRDIHTQTASUMFGLPAEAIDPLMRRAAKTINFGVLYGMSAHRLSQELSIPYEEAVAFI |
| 2789 (Teg) Pol | 1 | ELRVLAHLSGDENLIQVFQEGRDIHTQTASUMFGLPAEAINPLMRRAAKTINFGVLYGMSAHRLSQELSIPYEEAVAFI |
| 2795 (Teg) Pol | 1 | ELRVLAHLSGDENLIQVFQEGRDIHTQTASUMFGLPAEAINPLMRRAAKTINFGVLYGMSAHRLSQELSIPYEEAVAFI |
| 2798 (Teg) Pol | 1 | ELRVLAHLSGDENLIQVFQEGRDIHTQTASUMFGLPAEAIDPLMRRAAKTINFGVLYGMSAHRLSQELSIPYEEAVAFI |
| pol-9-st284 (Teg) Pol | 1 | ELRVLAHLSGDENLIQVFQEGRDIHTQTASUMFGLPAEAIDPLMRRAAKTINFGVLYGMSAHRLSQELSIPYEEAVAFI |
| pol-7-st140 (Teg) Pol | 1 | ELRVLAHLSGDENLIQVFQEGRDIHTETASUMFGLPAEAIDPLFRRAAKTINFGVLYGMSAHRLSQELGIPYEEAVAFI |
| Taq Pol | 1 | ELRVLAHLSGDENLIRVFQEGRDIHTETASUMFGVPREAVDPLMRRAAKTINFGVLYGMSAHRLSQELAIPYEEAVAFI |
| Tth Pol | 1 | ELRVLAHLSGDENLIRVFQEGKDIHTQTASUMFGVPPEAVDPLMRRAAKTVNFGVLYGMSAHRLSQELAIPYEEAVAFI |
| Tfl Pol | 1 | ELRVLAHLSGDENLIRVFQEGRDIHTQTASUMFGVSPEGVDPLMRRAAKTINFGVLYGMSAHRLSCELSIPYEEAVAFI |
| Tfi Pol | 1 | ELRVLAHLSGDENLRVFREGKDIHTETAAUMFGLDPRLVDPFMRRAAKTINFGVLYGMSAHRLSQELGIDYKEAVAFI |
| Tbr Pol | 1 | ELRVLAHLSGDENLIRVFQEGRDIHTQTASUMFGLPAEAIDPLFRRAAKTINFGVLYGMSAHRLSQELGIPYEEAVAFI |
| | | |
| 2123 (Teg) Pol | 80 | DRYFQSYPKVKAWIERTLEEGRQRGYVETLFGRRRYVPDLNARVKSVREAAERMAFNMPVQGTAADLMKLAMVRLFPRLPEVGARML |
| 2124 (Teg) Pol | 80 | DRYFQSYPKVKAWIERTLEEGRQRGYVETLFGRRRYVPDLNARVKSVREAAERMAFNMPVQGTAADLMKLAMVRLFPRLPEVGARML |
| 2789 (Teg) Pol | 80 | DRYFQSYPKVKAWIERTLEEGRQRGYVETLFGRRRYVPDLNARVKSVREAAERMAFNMPVQGTAADLMKLAMVRLFPRLPEVGARML |
| 2795 (Teg) Pol | 80 | DRYFQSYPKVKAWIERTLEEGRQRGYVETLFGRRRYVPDLNARVKSVREAAERMAFNMPVQGTAADLMKLAMVRLFPRLPEVGARML |
| 2798 (Teg) Pol | 80 | DRYFQSYPKVKAWIERTLEEGRQRGYVETLFGRRRYVPDLNARVKSVREAAERMAFNMPVQGTAADLMKLAMVRLFPRLPEVGARML |
| pol-9-st284 (Teg) Pol | 80 | DRYFQSYPKVKAWIERTLEEGRQRGYVETLFGRRRYVPDLNARVKSVREAAERMAFNMPVQGTAADLMKLAMVRLFPRLPEVGARML |
| pol-7-st140 (Teg) Pol | 80 | DRYFQSYPKVKAWIERTLEEGRKRGYVETLFGRRRYVPDLNARVKSVREAAERMAFNMPVQGTAADLMKLAMVRLFPRLEMGARML |
| Taq Pol | 80 | ERYFQSFPKVRAWIEKTLEEGRRRGYVETLFGRRRYVPDLEARVKSVREAAERMAFNMPVQGTAADLMKLAMVRLFPRLEMGARML |
| Tth Pol | 80 | ERYFQSFPKVRAWIEKTLEEGRRRGYVETLFGRRRYVPDLNARVKSVREAAERMAFNMPVQGTAADLMKLAMVRLFPRLEMGARML |
| Tfl Pol | 80 | ERYFQSYPKVRAWIECTLEEGRQRGYVETLFGRRRYVPDLNARVKSVREAAERMAFNMPVQGTAADLMKLAMVRLFPRLCELGARML |
| Tfi Pol | 80 | ERYFQSFPKVRAWIETLEEGRIRGYVETLFGRRRYVPDLSRVRSVREAAERMAFNMPVQGTAADLMKIAMVKLFPRLNLGAHLL |
| Tbr Pol | 80 | DRYFQSYPKVKAWIERTLEEGRQRGYVETLFGRRRYVPDLNARVKSVREAAERMAFNMPVQGTAAWLMKLAMVKLFPRLPEVGARML |

Phylogentic Dendrogram (polA Gene - Conserved Region)

Full Length *Thermus spec.* PolA Sequence Alignment

Fig. 11b
Full Length *Thermus spec.* PolA Sequence Alignment Cont.

Phylogentic Dendrogram Based on Full Length PolA Sequence Alignment

Outline of Large-Scale Teg DNA Polymerase Purification

Purification of Teg DNA Polymerase on Butyl-Sepharose

Purification of Teg DNA Polymerase on Heparin-Sepharose

Final Gel Analysis of the Teg DNA Polymerase vs. Taq and Tbr DNA Polymerase

Beta Actin PCR Activity Assay with the First Step Enzyme Stock Dilutions of Teg DNA Polymerase Beta Actin PCR Activity Assay with the Second Step Enzyme Dilutions of Teg DNA Polymerase

Fig. 21 *Beta Actin PCR Activity Titration Assay with Final Teg and Tbr DNA Polymerase Dilutions*

*Plot of the Endpoint PCR Product Yield versus Polymerase Activity in the Final Beta Actin PCR Activity Titration Assay*

Fig. 24  Real-Time PCR Heat Stability Challenge

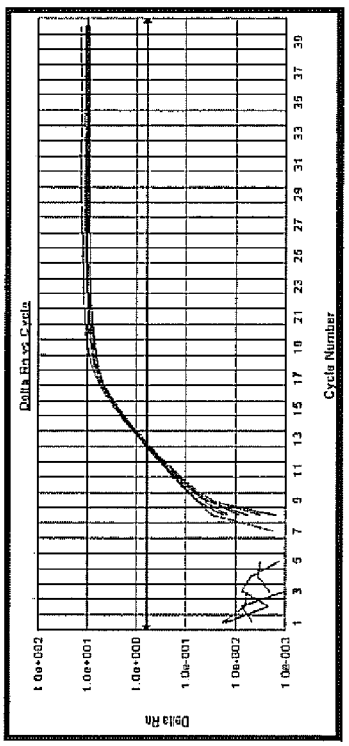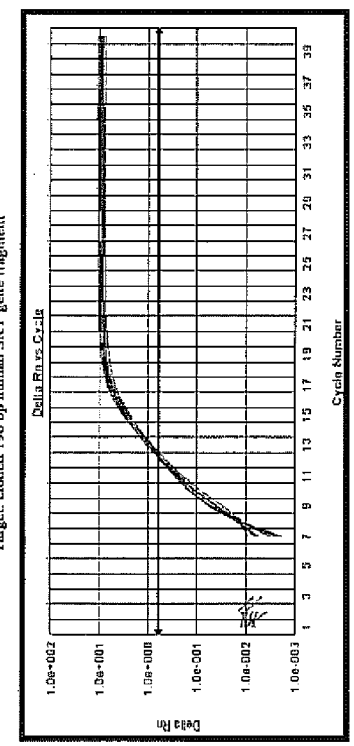
Fig. 25

Fig. 26    Fidelity Assay

Fig. 27  Fidelity Assay

Fig. 30 List of sequences disclosed

SequenceName : SEQ ID NO. 1 (Taq Pol I DNA Sequence)
SequenceName : SEQ ID NO. 2 (Taq Pol I Prot. Sequence)
SequenceName : SEQ ID NO. 3 (Thermus brockianus Pol I DNA Sequence)
SequenceName : SEQ ID NO. 4 (Thermus brockianus Pol I Prot. Sequence)
SequenceName : SEQ ID NO. 5 (Thermus eggertssonii DNA Pol. I DNA Sequence)
SequenceName : SEQ ID NO. 6 (Thermus eggertssonii DNA Pol. I Prot. Sequence)
SequenceName : SEQ ID NO. 7 (Thermus flavus DNA Pol I DNA Sequence)
SequenceName : SEQ ID NO. 8 (Thermus flavus DNA Pol. I Prot. Sequence)
SequenceName : SEQ ID NO. 9 (Thermus filiformis DNA Pol. I DNA Sequence)
SequenceName : SEQ ID NO. 10 (Thermus filiformis DNA Pol. I Prot. Sequence)
SequenceName : SEQ ID NO. 11 (Thermus thermophilus DNA Pol. I DNA Sequence)
SequenceName : SEQ ID NO. 12 (Thermus thermophilus DNA Pol. I Prot. Sequence)
SequenceName : SEQ ID NO. 13 (Thermus flavus DNA Pol I Conserved Region)
SequenceName : SEQ ID NO. 14 (Thermus filiformis DNA Pol I Conserved Region)
SequenceName : SEQ ID NO. 15 (Thermus thermophilus DNA Pol I Conserved Region)
SequenceName : SEQ ID NO. 16 (Thermus aquaticus DNA Pol I Conserved Region)
SequenceName : SEQ ID NO. 17 strain #249 (Teg) DNA Pol I Conserved Region
SequenceName : SEQ ID NO. 18 strain #2123 (Teg) DNA Pol I Conserved Region
SequenceName : SEQ ID NO. 19 strain #2124 (Teg) DNA Pol I Conserved Region
SequenceName : SEQ ID NO. 20 strain #284 (Teg) DNA Pol I Conserved Region
SequenceName : SEQ ID NO. 21 (2795 (Teg) DNA Pol I Conserved Region)
SequenceName : SEQ ID NO. 22 strain #2789 (Teg) DNA Pol I Conserved Region
SequenceName : SEQ ID NO. 23 strain #2798 (Teg) DNA Pol I Conserved Region
SequenceName : SEQ ID NO. 24 strain #140 {Tbr} 16S rRNA
SequenceName : SEQ ID NO. 25 strain #284 {Teg} 16S rRNA
SequenceName : SEQ ID NO. 26 strain #2789 {Teg} 16S rRNA
SequenceName : SEQ ID NO. 27 strain #2123 {Teg} 16S rRNA
SequenceName : SEQ ID NO. 28 (Thermus aquaticus 16S rRNA)
SequenceName : SEQ ID NO. 29 (Thermus thermophilus 16S rRNA)
SequenceName : SEQ ID NO. 30 (Thermus brockianus 16S rRNA)
SequenceName : SEQ ID NO. 31 (Thermus ignitarrae 16S rRNA)
SequenceName : SEQ ID NO. 32 (Thermus antranikianus 16S rRNA)
SequenceName : SEQ ID NO. 33 (Thermus scotoductus 16S rRNA)
SequenceName : SEQ ID NO. 34 (Thermus oshimai 16S rRNA)
SequenceName : SEQ ID NO. 35 (Example)
SequenceName : SEQ ID NO. 36 A-Forw.
SequenceName : SEQ ID NO. 37 C-Rev.
SequenceName : SEQ ID NO. 38 Arb. 1
SequenceName : SEQ ID NO. 39. Arb. 2
SequenceName : SEQ ID NO. 40 Arb. 3
SequenceName : SEQ ID NO. 41 M13 Revers Primer - 24 (-48)
Sequence Name: SEQ ID NO. 42 Primer R805
Sequence Name: SEQ ID NO. 43 Thermus eggertsonii DNA polymerase codon optimized - DNA sequence; Sense strand
Sequence Name: SEQ ID NO. 44 Thermus eggertsonii DNA polymerase codon optimized - amino acid sequence

SEQUENCE LISTING

<160> NUMBER OF SEQ ID NOS: 44

<210> SEQ ID NO 1
<211> LENGTH: 2499
<212> TYPE: DNA
<213> ORGANISM: Thermus aquaticus

<400> SEQUENCE: 1

```
atgaggggga tgctgcccct ctttgagccc aagggccggg tcctcctggt ggacggccac      60
cacctggcct accgcacctt ccacgccctg aagggcctca ccaccagccg ggggagccg      120 gtgcaggcgg tctacggctt cgccaagagc ctcctcaagg ccctcaagga ggacggggac     180
gcggtgatcg tggtctttga cgccaaggcc ccctccttcc gccacgaggc ctacggggggg   240 tacaaggcgg gccgggcccc cacgccgag gactttcccc ggcaactcgc cctcatcaag      300
gagctggtgg acctcctggg gctggcgcgc ctcgaggtcc cgggctacga ggcggacgac     360
gtcctggcca gctggccaa gaaggcgaa aaggagggct acgaggtccg catcctcacc       420
gccgacaaag acctttacca gctcctttcc gaccgcatcc acgccctcca ccccgagggg     480
tacctcatca cccccggcctg gctttgggaa agtacggcc tgaggcccga ccagtgggcc     540
gactaccggg ccctgaccgg ggacgagtcc gacaaccttc ccggggtcaa gggcatcggg     600
gagaagacgg cgaggaagct tctggaggag tgggggagcc tggaagccct cctcaagaac     660
ctggaccggc tgaagcccgc catccgggag aagatcctgg cccacatgga cgatctgaag     720
ctctcctggg acctggccaa ggtgcgcacc gacctgcccc tggaggtgga cttcgccaaa     780
aggcgggagc ccgaccggga gaggcttagg gcctttctgg agaggcttga gtttggcagc     840
ctcctccacg agttcggcct tctggaaagc ccaaggccc tggaggaggc ccctggccc       900 ccgccggaag gggccttcgt gggctttgtg ctttcccgca aggagcccat gtgggccgat     960
cttctggccc tggccgccgc caggggggc cgggtccacc gggcccccga gccttataaa    1020
gccctcaggg acctgaagga ggcgcgggggg cttctcgcca aagacctgag cgttctggcc   1080
ctgagggaag gccttggcct cccgcccggc gacgacccca tgctcctcgc ctacctcctg    1140
gacccttcca acaccacccc cgaggggtg gcccggcgct acggcgggga gtggacggag    1200
gaggcggggg agcgggccgc cctttccgag aggctcttcg ccaacctgtg ggggaggctt    1260 gaggggagg agaggctcct ttggctttac cgggaggtgg agaggcccct ttccgctgtc     1320
ctggcccaca tggaggccac gggggtgcgc ctggacgtgg cctatctcag ggccttgtcc    1380
ctggaggtgg ccgaggagat cgcccgcctc gaggccgagg tcttccgcct ggccggccac    1440
cccttcaacc tcaactcccg ggaccagctg gaaagggtcc tctttgacga gctagggctt    1500
cccgccatcg gcaagacgga gaagaccggc aagcgctcca ccagcgccgc cgtcctggag    1560
gccctccgcg aggcccaccc catcgtggag aagatcctgc agtaccggga gctcaccaag    1620
ctgaagagca cctacattga ccccttgccg gacctcatcc accccaggac gggccgcctc    1680
cacacccgct tcaaccagac ggccacggcc acgggcaggc taagtagctc cgatcccaac    1740
ctccagaaca tcccgtccg caccccgctt ggcagagga tccgccgggc cttcatcgcc     1800 gaggagggt ggctattggt ggccctggac tatagccaga tagagctcag ggtgctggcc    1860
cacctctccg gcgacgagaa cctgatccgg gtcttccagg aggggcggga catccacacg    1920
gagaccgcca gctggatgtt cggcgtcccc cgggaggccg tggacccccct gatgcgccgg    1980
```

```
gcggccaaga ccatcaactt cggggtcctc tacggcatgt cggcccaccg cctctcccag    2040
gagctagcca tcccttacga ggaggcccag gccttcattg agcgctactt tcagagcttc    2100
cccaaggtgc gggcctggat tgagaagacc ctggaggagg caggaggcg ggggtacgtg     2160 gagaccctct tcggccgccg ccgctacgtg ccagacctag aggcccgggt gaagagcgtg    2220
cgggaggcgg ccgagcgcat ggccttcaac atgcccgtcc agggcaccgc cgccgacctc    2280
atgaagctgg ctatggtgaa gctcttcccc aggctggagg aaatgggggc caggatgctc    2340
cttcaggtcc acgacgagct ggtcctcgag gccccaaaag agagggcgga ggccgtggcc    2400
cggctggcca aggaggtcat ggaggggtg tatcccctgg ccgtgcccct ggaggtggag     2460
gtggggatag ggaggactg gctctccgcc aaggagtga                            2499
```

<210> SEQ ID NO 2
<211> LENGTH: 832
<212> TYPE: PRT
<213> ORGANISM: Thermus aquaticus

<400> SEQUENCE: 2

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Ala Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285
```

```
Glu Ser Pro Lys Ala Leu Glu Ala Pro Trp Pro Pro Glu Gly
    290                 295                 300
Ala Phe Val Gly Phe Val Leu Ser Arg Lys Glu Pro Met Trp Ala Asp
305                 310                 315                 320
Leu Leu Ala Leu Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
            340                 345                 350
Ala Lys Asp Leu Ser Val Leu Ala Leu Arg Glu Gly Leu Gly Leu Pro
    355                 360                 365
Pro Gly Asp Asp Pro Met Leu Leu Ala Tyr Leu Leu Asp Pro Ser Asn
370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
            420                 425                 430
Val Glu Arg Pro Leu Ser Ala Val Leu Ala His Met Glu Ala Thr Gly
    435                 440                 445
Val Arg Leu Asp Val Ala Tyr Leu Arg Ala Leu Ser Leu Glu Val Ala
450                 455                 460
Glu Glu Ile Ala Arg Leu Glu Ala Glu Val Phe Arg Leu Ala Gly His
465                 470                 475                 480
Pro Phe Asn Leu Asn Ser Arg Asp Gln Leu Glu Arg Val Leu Phe Asp
                485                 490                 495
Glu Leu Gly Leu Pro Ala Ile Gly Lys Thr Glu Lys Thr Gly Lys Arg
            500                 505                 510
Ser Thr Ser Ala Ala Val Leu Glu Ala Leu Arg Glu Ala His Pro Ile
    515                 520                 525
Val Glu Lys Ile Leu Gln Tyr Arg Glu Leu Thr Lys Leu Lys Ser Thr
530                 535                 540
Tyr Ile Asp Pro Leu Pro Asp Leu Ile His Pro Arg Thr Gly Arg Leu
545                 550                 555                 560
His Thr Arg Phe Asn Gln Thr Ala Thr Ala Thr Gly Arg Leu Ser Ser
                565                 570                 575
Ser Asp Pro Asn Leu Gln Asn Ile Pro Val Arg Thr Pro Leu Gly Gln
            580                 585                 590
Arg Ile Arg Arg Ala Phe Ile Ala Glu Glu Gly Trp Leu Leu Val Ala
    595                 600                 605
Leu Asp Tyr Ser Gln Ile Glu Leu Arg Val Leu Ala His Leu Ser Gly
610                 615                 620
Asp Glu Asn Leu Ile Arg Val Phe Gln Glu Gly Arg Asp Ile His Thr
625                 630                 635                 640
Glu Thr Ala Ser Trp Met Phe Gly Val Pro Arg Glu Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
    675                 680                 685
Ala Gln Ala Phe Ile Glu Arg Tyr Phe Gln Ser Phe Pro Lys Val Arg
690                 695                 700
Ala Trp Ile Glu Lys Thr Leu Glu Glu Gly Arg Arg Arg Gly Tyr Val
```

|     |     |     |     | 705 |     |     |     |     | 710 |     |     |     |     | 715 |     |     |     |     | 720 |
|-----|-----|-----|-----|-----|-----|-----|-----|-----|-----|-----|-----|-----|-----|-----|-----|-----|-----|-----|-----|

Glu Thr Leu Phe Gly Arg Arg Arg Tyr Val Pro Asp Leu Glu Ala Arg
                  725                730                735

Val Lys Ser Val Arg Glu Ala Ala Glu Arg Met Ala Phe Asn Met Pro
           740                745                750

Val Gln Gly Thr Ala Ala Asp Leu Met Lys Leu Ala Met Val Lys Leu
        755                760                765

Phe Pro Arg Leu Glu Glu Met Gly Ala Arg Met Leu Leu Gln Val His
      770                775                780

Asp Glu Leu Val Leu Glu Ala Pro Lys Glu Arg Ala Glu Ala Val Ala
785                790                795              800

Arg Leu Ala Lys Glu Val Met Glu Gly Val Tyr Pro Leu Ala Val Pro
           805                810                815

Leu Glu Val Glu Val Gly Ile Gly Glu Asp Trp Leu Ser Ala Lys Glu
        820                825                830

<210> SEQ ID NO 3
<211> LENGTH: 3942
<212> TYPE: DNA
<213> ORGANISM: Thermus brockianus

<400> SEQUENCE: 3

| | | | | |
|---|---|---|---|---|
| atgcttcccc | tctttgagcc | caagggccgg | gtgctcctgg | tggacggcca | ccacctggcc | 60 |
| taccgtaact | tcttcgccct | caaggggctc | accacgagcc | ggggcgagcc | cgtgcaaggg | 120 |
| gtctacggct | tcgccaaaag | cctcctcaag | gccctgaagg | aggacgggga | cgtggtcatc | 180 |
| gtggtctttg | acgccaaggc | ccctcttttt | cgccacgagg | cctacggggc | ctacaaggcg | 240 |
| ggccgggccc | ctaccccgga | ggactttccg | aggcagcttg | ccctcatgaa | ggagcttgtg | 300 |
| gaccttttgg | ggctggagcg | cctcgaggtc | ccgggctttg | aggcggacga | tgtcctcgcc | 360 |
| gccctggcca | gaaggcggga | gcggaaggg | tacgaggtgc | gcatcctcac | cgccgaccgg | 420 |
| gacctcttcc | agcttctttc | ggaccgcatc | gccgtcctgc | acccggaagg | ccacctcatc | 480 |
| accccggggt | ggctttggga | gaggtacggc | ctgagaccgg | agcagtgggt | ggacttccgc | 540 |
| gccctggccg | gcgacccttc | cgacaacatc | cccggggtga | aggggatcgg | cgagaagacg | 600 |
| gccctgaagc | tcctaaagga | gtggggtagt | ctggaaaata | tccaaaaaaa | cctggaccag | 660 |
| gtcagtcccc | cttccgtgcg | cgagaagatc | caggcccacc | tggacgacct | caggctctcc | 720 |
| caggagcttt | cccgggtgcg | cacggacctt | cccttggagg | tggactttag | aaggcggcgg | 780 |
| gagcccgata | gggaaggcct | tagggccttc | ttagagcggc | ttgagttcgg | gagcctcctc | 840 |
| cacgagttcg | gcctcctgga | aagccccag | gcggcggagg | aggcccttg | gccgccgccg | 900 |
| gaagggcct | tcttgggctt | ccgcctctcc | cggcccgagc | ccatgtgggc | ggaactcctt | 960 |
| tccttggcgg | caagcgccaa | gggccgggtc | taccggcgg | aggcgcccca | taaggccctt | 1020 |
| tcggacctga | aggagatccg | ggggcttctc | gccaaggacc | tcgccgtctt | ggccctgagg | 1080 |
| gaggggctcg | gccttccccc | cacggacgat | cccatgctcc | tcgcctacct | cctggacccc | 1140 |
| tccaacacca | cccccgaggg | cgtggcccgg | cgctacgggg | gggagtggac | ggaggaggcg | 1200 |
| ggggagaggg | ccttgcttgc | cgaaaggctt | tacgagaacc | tcctaagacg | cctgaaaggg | 1260 |
| gaagaaaagc | tcctttggct | ctacgaggag | gtggaaaagc | ccctttcccg | ggtcctcgcc | 1320 |
| cacatggagg | ccacggggt | gaggctggac | gtaccctacc | taagggccct | ttccctggag | 1380 |
| gtggcggcg | agatgggccg | cctggaggag | gaggttttcc | gcctggcggg | ccaccccttc | 1440 |
| aacctgaaca | tgcttcccct | ctttgagccc | aagggccggg | tgctcctggt | ggacggccac | 1500 |

```
cacctggcct accgtaactt cttcgccctc aagggctca ccacgagccg gggcgagccc      1560
gtgcaagggg tctacggctt cgccaaaagc ctcctcaagg ccctgaagga ggacggggac      1620
gtggtcatcg tggtctttga cgccaaggcc ccctctttc gccacgaggc ctacggggcc      1680
tacaaggcgg gccgggcccc taccccggag gactttccga ggcagcttgc cctcatgaag      1740
gagcttgtgg accttttggg gctggagcgc ctcgaggtcc cgggctttga ggcggacgat      1800
gtcctcgccg ccctggccaa gaaggcggag cgggaagggt acgaggtgcg catcctcacc      1860
gccgaccggg acctcttcca gcttctttcg gaccgcatcg ccgtcctgca cccgaaggc       1920
cacctcatca ccccggggtg gctttgggag aggtacggcc tgagaccgga gcagtgggtg      1980
gacttccgcg ccctggccgg cgaccccttcc gacaacatcc ccggggtgaa ggggatcggc     2040
gagaagacgg ccctgaagct cctaaaggag tggggtagtc tggaaaatat ccaaaaaaac     2100
ctggaccagg tcagtccccc ttccgtgcgc gagaagatcc aggcccacct ggacgacctc     2160
aggctctccc aggagctttc ccgggtgcgc acggaccttc ccttggaggt ggactttaga     2220
aggcggcggg agcccgatag ggaaggcctt agggccttct tagagcggct tgagttcggg     2280
agcctcctcc acgagttcgg cctcctggaa agccccagg cggcggagga ggcccttgg       2340
ccgccgccgg aaggggcctt cttgggcttc cgcctctccc ggcccgagcc catgtgggcg     2400
gaactccttt ccttggcggc aagcgccaag ggccgggtct accgggcgga ggcgcccat     2460
aaggcccttt cggacctgaa ggagatccgg gggcttctcg ccaaggacct cgccgtcttg     2520
gccctgaggg aggggctcgg ccttccccc acggacgatc ccatgctcct cgcctacctc     2580
ctggacccct ccaacaccac ccccgagggc gtggcccggc gctacggggg ggagtggacg     2640
gaggaggcgg gggagagggc cttgcttgcc gaaaggcttt acgagaacct cctaagacgc     2700
ctgaaagggg aagaaaagct cctttggctc tacgaggagg tggaaaagcc cctttcccgg     2760
gtcctcgccc acatggaggc cacggggtg aggctgacg taccctacct aagggccctt     2820
tccctggagg tggcggcgga gatgggccgc ctggaggagg aggttttccg cctggcgggc    2880
caccccttca acctgaactc ccgcgaccag ctggaaaggg tgctctttga cgagcccggg    2940
cttccccca tcggcaagac ggaaaaaacc gggaagcgct ccaccagcgc cgccgtcctc     3000
gaggccctgc gggaggccca ccccatcgtg gagaagatcc tccagtaccg ggagctcgcc    3060
aagctcaagg gcacctacat tgacccctt cccgccctgg tccaccccag gacgggcagg    3120
ctccacaccc gcttcaacca gacggccacg gccacgggcc gcctttccag ctccgacccc    3180
aacctgcaga acattcccgt gcgcacccc ttgggccaaa ggatccgccg ggccttcgtg    3240
gccgaggagg ggtaccttct cgtggccctg gactactccc aaattgagtt gagggtcctg    3300
gcccacctct cggggacga aaacctcatc cgggtcttcc aggagggccg ggacatccac    3360
acccagacgg cgagctggat gttcggcctg ccggcggagg ccatagaccc cctcaggcgc    3420
cgggcggcca agaccatcaa cttcggcgtc ctctacggca tgtccgccca ccggctttcc    3480
caggagctgg cgatccccta cgaggaggcg gtggccttca ttgaccgcta tttccagagc    3540
taccccaagg tgaaggcctg gattgaaagg accctggagg aggggcggca aaggggtac     3600
gtggagaccc tcttcggccg caggcgctac gtgcccgacc tcaacgcccg ggtaaagagc    3660
gtgcgggagg cggcggagcg catggccttt aacatgccgt tgcagggcac cgccgctgtc    3720
ctgatgaagc tcgccatggt gaggctcttc cctaggcttc ccgaggtggg ggcgaggatg    3780
ctcctccagg tccacgacga gctcctcctg gaggcgccca aggagcgggc ggaggaggcg    3840
gcggccctgg ccaaggaggt catggagggg gtctggcccc tggccgtgcc cctggaggtg    3900
```
gaggtgggca tcggggagga ctggctttcc gccaagggct ag         3942

<210> SEQ ID NO 4
<211> LENGTH: 830
<212> TYPE: PRT
<213> ORGANISM: Thermus brockianus

<400> SEQUENCE: 4

Met Leu Pro Leu Phe Glu Pro Lys Gly Arg Val Leu Val Asp Gly
1               5                   10                  15

His His Leu Ala Tyr Arg Asn Phe Phe Ala Leu Lys Gly Leu Thr Thr
            20                  25                  30

Ser Arg Gly Glu Pro Val Gln Gly Val Tyr Gly Phe Ala Lys Ser Leu
        35                  40                  45

Leu Lys Ala Leu Lys Glu Asp Gly Asp Val Ile Val Val Phe Asp
    50                  55                  60

Ala Lys Ala Pro Ser Phe Arg His Glu Ala Tyr Gly Ala Tyr Lys Ala
65                  70                  75                  80

Gly Arg Ala Pro Thr Pro Glu Asp Phe Pro Arg Gln Leu Ala Leu Met
                85                  90                  95

Lys Glu Leu Val Asp Leu Leu Gly Leu Glu Arg Leu Glu Val Pro Gly
            100                 105                 110

Phe Glu Ala Asp Asp Val Leu Ala Ala Leu Ala Lys Lys Ala Glu Arg
        115                 120                 125

Glu Gly Tyr Glu Val Arg Ile Leu Thr Ala Asp Arg Asp Leu Phe Gln
    130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Arg Pro Glu Gln Trp
                165                 170                 175

Val Asp Phe Arg Ala Leu Ala Gly Asp Pro Ser Asp Asn Ile Pro Gly
            180                 185                 190

Val Lys Gly Ile Gly Glu Lys Thr Ala Leu Lys Leu Leu Lys Glu Trp
        195                 200                 205

Gly Ser Leu Glu Asn Ile Gln Lys Asn Leu Asp Gln Val Ser Pro Pro
    210                 215                 220

Ser Val Arg Glu Lys Ile Gln Ala His Leu Asp Asp Leu Arg Leu Ser
225                 230                 235                 240

Gln Glu Leu Ser Arg Val Arg Thr Asp Leu Pro Leu Glu Val Asp Phe
                245                 250                 255

Arg Arg Arg Arg Glu Pro Asp Arg Glu Gly Leu Arg Ala Phe Leu Glu
            260                 265                 270

Arg Leu Glu Phe Gly Ser Leu Leu His Glu Phe Gly Leu Leu Glu Ser
        275                 280                 285

Pro Gln Ala Ala Glu Glu Ala Pro Trp Pro Pro Glu Gly Ala Phe
    290                 295                 300

Leu Gly Phe Arg Leu Ser Arg Pro Glu Pro Met Trp Ala Glu Leu Leu
305                 310                 315                 320

Ser Leu Ala Ala Ser Ala Lys Gly Arg Val Tyr Arg Ala Glu Ala Pro
                325                 330                 335

His Lys Ala Leu Ser Asp Leu Lys Glu Ile Arg Gly Leu Leu Ala Lys
            340                 345                 350

Asp Leu Ala Val Leu Ala Leu Arg Glu Gly Leu Gly Leu Pro Pro Thr
        355                 360                 365

```
Asp Asp Pro Met Leu Leu Ala Tyr Leu Leu Asp Pro Ser Asn Thr Thr
370                 375                 380

Pro Glu Gly Val Ala Arg Arg Tyr Gly Gly Glu Trp Thr Glu Glu Ala
385                 390                 395                 400

Gly Glu Arg Ala Leu Leu Ala Glu Arg Leu Tyr Glu Asn Leu Leu Arg
                405                 410                 415

Arg Leu Lys Gly Glu Glu Lys Leu Leu Trp Leu Tyr Glu Glu Val Glu
            420                 425                 430

Lys Pro Leu Ser Arg Val Leu Ala His Met Glu Ala Thr Gly Val Arg
        435                 440                 445

Leu Asp Val Pro Tyr Leu Arg Ala Leu Ser Leu Glu Val Ala Ala Glu
450                 455                 460

Met Gly Arg Leu Glu Glu Val Phe Arg Leu Ala Gly His Pro Phe
465                 470                 475                 480

Asn Leu Asn Ser Arg Asp Gln Leu Glu Arg Val Leu Phe Asp Glu Pro
                485                 490                 495

Gly Leu Pro Pro Ile Gly Lys Thr Glu Lys Thr Gly Lys Arg Ser Thr
                500                 505                 510

Ser Ala Ala Val Leu Glu Ala Leu Arg Glu Ala His Pro Ile Val Glu
        515                 520                 525

Lys Ile Leu Gln Tyr Arg Glu Leu Ala Lys Leu Lys Gly Thr Tyr Ile
530                 535                 540

Asp Pro Leu Pro Ala Leu Val His Pro Arg Thr Gly Arg Leu His Thr
545                 550                 555                 560

Arg Phe Asn Gln Thr Ala Thr Ala Thr Gly Arg Leu Ser Ser Ser Asp
                565                 570                 575

Pro Asn Leu Gln Asn Ile Pro Val Arg Thr Pro Leu Gly Gln Arg Ile
                580                 585                 590

Arg Arg Ala Phe Val Ala Glu Glu Gly Tyr Leu Leu Val Ala Leu Asp
            595                 600                 605

Tyr Ser Gln Ile Glu Leu Arg Val Leu Ala His Leu Ser Gly Asp Glu
        610                 615                 620

Asn Leu Ile Arg Val Phe Gln Glu Gly Arg Asp Ile His Thr Gln Thr
625                 630                 635                 640

Ala Ser Trp Met Phe Gly Leu Pro Ala Glu Ala Ile Asp Pro Leu Arg
                645                 650                 655

Arg Arg Ala Ala Lys Thr Ile Asn Phe Gly Val Leu Tyr Gly Met Ser
            660                 665                 670

Ala His Arg Leu Ser Gln Glu Leu Gly Ile Pro Tyr Glu Glu Ala Val
        675                 680                 685

Ala Phe Ile Asp Arg Tyr Phe Gln Ser Tyr Pro Lys Val Lys Ala Trp
690                 695                 700

Ile Glu Arg Thr Leu Glu Glu Gly Arg Gln Arg Gly Tyr Val Glu Thr
705                 710                 715                 720

Leu Phe Gly Arg Arg Tyr Val Pro Asp Leu Asn Ala Arg Val Lys
                725                 730                 735

Ser Val Arg Glu Ala Ala Glu Arg Met Ala Phe Asn Met Pro Val Gln
            740                 745                 750

Gly Thr Ala Ala Val Leu Met Lys Leu Ala Met Val Arg Leu Phe Pro
        755                 760                 765

Arg Leu Pro Glu Val Gly Ala Arg Met Leu Leu Gln Val His Asp Glu
770                 775                 780

Leu Leu Leu Glu Ala Pro Lys Glu Arg Ala Glu Glu Ala Ala Ala Leu
785                 790                 795                 800
```

Ala Lys Glu Val Met Glu Gly Val Trp Pro Leu Ala Val Pro Leu Glu
        805                 810                 815

Val Glu Val Gly Ile Gly Glu Asp Trp Leu Ser Ala Lys Gly
        820                 825                 830

<210> SEQ ID NO 5
<211> LENGTH: 2493
<212> TYPE: DNA
<213> ORGANISM: Thermus eggertssonii

<400> SEQUENCE: 5

```
atgcttcccc tctttgagcc aagggccgg gtgctcctgg tggacggcca ccacctggcc      60
taccgcaact ttttcgccct caaagggctc accacgagcc ggggcgagcc ggtgcaaggg     120
gtctacggct tcgccaaaag cctcctcaag gccctgaagg aggacgggga cgtggtcatc     180
gtggtctttg acgccaaggc ccccttttc cgccacgagg cctacgaggc ctacaaggcg     240
ggccgggccc ccaccccgga ggactttccc cggcagctcg ccctcataaa ggagctggtg     300
gacctcttgg ggctggagcg cctcgaggtc ccgggctttg aagcggacga tgtcctcgcc     360
accttggcca agcaagcgga gcgggaaggg tacgaggtgc gcatcctcac cgccgaccgg     420
gacctcttcc agctcctttc ggaccgcatc gccgtcctcc acccggaagg cacctcatc      480
accccggggt ggctttggga gcggtacggt ctgaagccgg agcagtgggt ggacttccgc     540
gccctggccg gcgaccctc cgacaacatc cccgggtga agggaatcgg ggagaagacc      600
gccctgaagc tcctcaagga gtgggggagc ctggaaaacc tcctcaagaa cctggaccat     660
gtgaagcctc cttccgtaag ggagaagatc ctcgcccacc tggacgacct caggctctcc     720
caggagcttt cccgggtgcg cacggacctc cccttgaagg tggactttaa aaagcggcgg     780
gagcccgata gggaagggct taaggccttc ttggagcggc ttgagtttgg aagcctcctc     840
cacgagttcg gcctcctgga agccccctt ccggcggagg aggcccatg gccgccgccg       900
gaagggcct ttttgggcta ccgcctttcc cggcccgagc catgtgggc ggagcttctt       960
gccttggcgg cgagcgccaa gggccgggtt taccggcgg aggagcccta tggggcccta    1020
aggggcctga aggaggtgcg ggggcttctt gccaaggacc tcgccgtctt ggccctaagg    1080
gagggcctgg accttccccc cacggacgac cccatgctcc tcgcttacct cctggacccc    1140
tccaacacca ccccgaggg cgtggcccgg cggtatgggg gggagtggac ggaggaggcg     1200
ggggagcggg cggtgctttc cgaaaggctc tacgagaacc tccttgggcg cttgagaggg    1260
gaagagaagc tcctttggct ttacgaggag gtggaaaagc ccctctcccg ggtcctcgcc    1320
cacatggagg ccacggggt gaggctggac gtggcctacc tcaaggccct ttccctggag    1380
gtggcggagg agatgcgccg cctggaggag gaggtcttcc gcctggcggg ccaccccttc    1440
aacctcaatt cccgcgacca gctggaaagg gtgctctttg acgagctcgg ccttccccc     1500
atcggcaaga cggagaagac tgggaagcgc tccacgagcg ccgccgtcct cgaggccctg    1560
cgggaggccc accccatcgt ggaaaagatc cttcagtacc gggaactggc caagctcaag    1620
ggcacctaca ttgacccct ccccgccctg gtccaccccca agacggggcg gctccacacc   1680
cgcttcaacc agacggccac ggccacgggc cgccttttcca gctccgaccc caacctgcag    1740
aacatccccg tgcgcacccc cttgggccaa aggatccgcc gggccttcgt ggccgaggag    1800
gggtacctgc tcgtggccct ggactatagc cagattgagc tcagggtcct ggcccacctc    1860
tcgggggacg agaacctcat ccaggtcttc caggagggcc gggacatcca cacccagacg    1920
gcgagctgga tgttcggcct gccggcggag gccatagacc ccctcatgcg ccgggcggcc    1980
```

```
aagaccatca acttcggcgt cctttacggc atgtccgccc atcggctttc ccaagagctc    2040
agcatcccct acgaggaggc ggtggccttc attgaccgct atttccagag ctaccccaag    2100
gtgaaggcct ggattgaaag gaccctggag gaggggcggc agaggggggta tgtggaaacc   2160 ctcttcggcc gcaggcgcta cgtgcccgac ctcaacgccc gggtaaagag cgtgcgggag    2220
gcggcggagc gcatggcctt taacatgccc gtgcagggca ccgccgccga cctgatgaag    2280
ctcgccatgg tgaggctttt ccccaggctt cccgaggtgg gggcgcggat gctcctccag    2340
gtccacgacg agctcctcct ggaggcgccc aaggagcggg cggaggcggc ggcggccctg    2400
gccaaggagg tcatggaggg ggtctggccc ctggccgtgc ccctggaggt ggaggtgggc    2460
atcggggagg actggctttc cgccaagggc tag                                 2493
```

<210> SEQ ID NO 6
<211> LENGTH: 830
<212> TYPE: PRT
<213> ORGANISM: Thermus eggertssonii

<400> SEQUENCE: 6

```
Met Leu Pro Leu Phe Glu Pro Lys Gly Arg Val Leu Val Asp Gly
1               5                   10                  15

His His Leu Ala Tyr Arg Asn Phe Phe Ala Leu Lys Gly Leu Thr Thr
                20                  25                  30

Ser Arg Gly Glu Pro Val Gln Gly Val Tyr Gly Phe Ala Lys Ser Leu
            35                  40                  45

Leu Lys Ala Leu Lys Glu Asp Gly Asp Val Val Ile Val Val Phe Asp
        50                  55                  60

Ala Lys Ala Pro Phe Phe Arg His Glu Ala Tyr Glu Ala Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Leu Glu Arg Leu Glu Val Pro Gly
            100                 105                 110

Phe Glu Ala Asp Asp Val Leu Ala Thr Leu Ala Lys Gln Ala Glu Arg
        115                 120                 125

Glu Gly Tyr Glu Val Arg Ile Leu Thr Ala Asp Arg Asp Leu Phe Gln
    130                 135                 140

Leu Leu Ser Asp Arg Ile Ala Val Leu His Pro Glu Gly His Leu Ile
145                 150                 155                 160

Thr Pro Gly Trp Leu Trp Glu Arg Tyr Gly Leu Lys Pro Glu Gln Trp
                165                 170                 175

Val Asp Phe Arg Ala Leu Ala Gly Asp Pro Ser Asp Asn Ile Pro Gly
            180                 185                 190

Val Lys Gly Ile Gly Glu Lys Thr Ala Leu Lys Leu Leu Lys Glu Trp
        195                 200                 205

Gly Ser Leu Glu Asn Leu Leu Lys Asn Leu Asp His Val Lys Pro Pro
    210                 215                 220

Ser Val Arg Glu Lys Ile Leu Ala His Leu Asp Asp Leu Arg Leu Ser
225                 230                 235                 240

Gln Glu Leu Ser Arg Val Arg Thr Asp Leu Pro Leu Lys Val Asp Phe
                245                 250                 255

Lys Lys Arg Arg Glu Pro Asp Arg Glu Gly Leu Lys Ala Phe Leu Glu
            260                 265                 270

Arg Leu Glu Phe Gly Ser Leu Leu His Glu Phe Gly Leu Leu Glu Ser
        275                 280                 285
```

```
Pro Leu Pro Ala Glu Glu Ala Pro Trp Pro Pro Glu Gly Ala Phe
    290                 295                 300
Leu Gly Tyr Arg Leu Ser Arg Pro Glu Pro Met Trp Ala Glu Leu Leu
305                 310                 315                 320
Ala Leu Ala Ala Ser Ala Lys Gly Arg Val Tyr Arg Ala Glu Glu Pro
                325                 330                 335
Tyr Gly Ala Leu Arg Gly Leu Lys Glu Val Arg Gly Leu Leu Ala Lys
            340                 345                 350
Asp Leu Ala Val Leu Ala Leu Arg Glu Gly Leu Asp Leu Pro Pro Thr
        355                 360                 365
Asp Asp Pro Met Leu Leu Ala Tyr Leu Leu Asp Pro Ser Asn Thr Thr
370                 375                 380
Pro Glu Gly Val Ala Arg Arg Tyr Gly Gly Glu Trp Thr Glu Glu Ala
385                 390                 395                 400
Gly Glu Arg Ala Val Leu Ser Glu Arg Leu Tyr Glu Asn Leu Leu Gly
                405                 410                 415
Arg Leu Arg Gly Glu Glu Lys Leu Leu Trp Leu Tyr Glu Glu Val Glu
            420                 425                 430
Lys Pro Leu Ser Arg Val Leu Ala His Met Glu Ala Thr Gly Val Arg
        435                 440                 445
Leu Asp Val Ala Tyr Leu Lys Ala Leu Ser Leu Glu Val Ala Glu Glu
    450                 455                 460
Met Arg Arg Leu Glu Glu Glu Val Phe Arg Leu Ala Gly His Pro Phe
465                 470                 475                 480
Asn Leu Asn Ser Arg Asp Gln Leu Glu Arg Val Leu Phe Asp Glu Leu
                485                 490                 495
Gly Leu Pro Pro Ile Gly Lys Thr Glu Lys Thr Gly Lys Arg Ser Thr
            500                 505                 510
Ser Ala Ala Val Leu Glu Ala Leu Arg Glu Ala His Pro Ile Val Glu
        515                 520                 525
Lys Ile Leu Gln Tyr Arg Glu Leu Ala Lys Leu Lys Gly Thr Tyr Ile
    530                 535                 540
Asp Pro Leu Pro Ala Leu Val His Pro Lys Thr Gly Arg Leu His Thr
545                 550                 555                 560
Arg Phe Asn Gln Thr Ala Thr Ala Thr Gly Arg Leu Ser Ser Ser Asp
                565                 570                 575
Pro Asn Leu Gln Asn Ile Pro Val Arg Thr Pro Leu Gly Gln Arg Ile
            580                 585                 590
Arg Arg Ala Phe Val Ala Glu Glu Gly Tyr Leu Leu Val Ala Leu Asp
        595                 600                 605
Tyr Ser Gln Ile Glu Leu Arg Val Leu Ala His Leu Ser Gly Asp Glu
    610                 615                 620
Asn Leu Ile Gln Val Phe Gln Glu Gly Arg Asp Ile His Thr Gln Thr
625                 630                 635                 640
Ala Ser Trp Met Phe Gly Leu Pro Ala Glu Ala Ile Asp Pro Leu Met
                645                 650                 655
Arg Arg Ala Ala Lys Thr Ile Asn Phe Gly Val Leu Tyr Gly Met Ser
            660                 665                 670
Ala His Arg Leu Ser Gln Glu Leu Ser Ile Pro Tyr Glu Glu Ala Val
        675                 680                 685
Ala Phe Ile Asp Arg Tyr Phe Gln Ser Tyr Pro Lys Val Lys Ala Trp
    690                 695                 700
Ile Glu Arg Thr Leu Glu Glu Gly Arg Gln Arg Gly Tyr Val Glu Thr
```

```
                705              710              715              720
Leu Phe Gly Arg Arg Tyr Val Pro Asp Leu Asn Ala Arg Val Lys
                725              730              735
Ser Val Arg Glu Ala Ala Glu Arg Met Ala Phe Asn Met Pro Val Gln
                740              745              750
Gly Thr Ala Ala Asp Leu Met Lys Leu Ala Met Val Arg Leu Phe Pro
                755              760              765
Arg Leu Pro Glu Val Gly Ala Arg Met Leu Leu Gln Val His Asp Glu
            770              775              780
Leu Leu Leu Glu Ala Pro Lys Glu Arg Ala Glu Ala Ala Ala Ala Leu
785              790              795              800
Ala Lys Glu Val Met Glu Gly Val Trp Pro Leu Ala Val Pro Leu Glu
                805              810              815
Val Glu Val Gly Ile Gly Glu Asp Trp Leu Ser Ala Lys Gly
                820              825              830

<210> SEQ ID NO 7
<211> LENGTH: 3047
<212> TYPE: DNA
<213> ORGANISM: Thermus flavus

<400> SEQUENCE: 7
atggcgatgc ttccctctct tgagcccaaa ggccgcgtgc tcctggtgga cggccaccac     60
ctggcctacc gcaccttctt tgccctcaag ggcctcacca ccagccgcgg cgaacccgtt    120
caggcggtct acggcttcgc caaaagcctc ctcaaggccc tgaaggagga cggggacgtg    180
gtggtggtgg tctttgacgc caaggccccc tccttccgcc acgaggccta cgaggcctac    240
aaggcggggc gggcccccac cccggaggac tttccccggc agctggccct catcaaggag    300
ttggtggacc tcctaggcct tgtgcggctg gaggttcccg gctttgaggc ggacgacgtg    360
ctggccaccc tggccaagcg gcggaaaaag gaggggtacg aggtgcgcat cctcactgcc    420
gaccgcgacc tctaccagct cctttcggag cgcatcgcca tcctccaccc tgagggtac     480
ctgatcaccc cggcgtggct ttacgagaag tacggcctgc gccggagca gtgggtggac    540
taccgggccc tggcggggga cccctcggat aacatccccg ggtgaaggg catcggggag    600
aagaccgccc agaggctcat ccgcgagtgg gggagcctgg aaaacctctt ccagcacctg    660
gaccaggtga agccctcctt gcgggagaag ctccaggcgg gcatggaggc cctggcctt     720
tcccggaagc tttcccaggt gcacactgac ctgcccctgg aggtggactt cgggaggcgc    780
cgcacaccca acctggaggg tctgcgggct tttttggagc ggttggagtt tggaagcctc    840
ctccacgagt tcggcctcct ggaggggccg aaggcggcag aggaggcccc tggcccctc    900
cggaaggggc ttttttgggc ttttcctttt cccgtcccga gcccatgtgg gccgagcttc    960
tggccctggc tggggcgtgg gagggcgcc tccatcgggc acaagacccc cttaggggcc   1020
tgagggacct taagggggtg cggggaatcc tggccaagga cctggcggtt ttggccctgc   1080
gggagggcct ggacctcttc ccagaggacg accccatgct cctggcctac cttctggacc   1140
cctccaacac caccccctgag ggggtggccc ggcgttacgg gggggagtgg acggaggatg   1200
cgggggagag ggccctcctg gccgagcgcc tcttccagac cctaaaggag cgccttaagg   1260
gagaagaacg cctgctttgg ctttacgagg aggtggagaa gccgctttcc cgggtgttgg   1320
cccggatgga ggccacgggg gtccggctgg acgtggccta cctccaggcc ctctccctgg   1380
aggtggagc ggaggtgcgc cagctggagg aggaggtctt ccgcctggcc ggccaccctt   1440
tcaacctcaa ctcccgcgac cagctggagc gggtgctctt tgacgagctg ggcctgcctg   1500
```

-continued

```
ccatcggcaa gacggagaag acggggaaac gctccaccag cgctgccgtg ctggaggccc      1560
tgcgagaggc ccaccccatc gtggaccgca tcctgcagta ccgggagctc accaagctca      1620
agaacaccta catagacccc ctgcccgccc tggtccaccc caagaccggc cggctccaca      1680
cccgcttcaa ccagacggcc accgccacgg gcaggctttc agctccgac cccaacctgc       1740 agaacatccc cgtgcgcacc cctctgggcc agcgcatccg ccgagccttc gtggccgagg      1800
agggctgggt gctggtggtc ttggactaca gccagattga gcttcgggtc ctggcccacc      1860
tctccgggga cgagaacctg atccgggtct tcaggaggg gagggacatc acacccaga       1920 ccgccagctg gatgttcggc gttcccccg aagggtaga ccctctgatg cgccgggcgg        1980
ccaagaccat caacttcggg gtgctctacg gcatgtccgc ccaccgcctc tccggggagc     2040
tttccatccc ctacgaggag gcggtggcct agacggggaa acgctccacc agcgctgccg    2100
tgctggaggc cctgcgagag gcccaccccca tcgtggaccg catcctgcag taccgggagc   2160
tcaccaagct caagaacacc tacatagacc ccctgcccgc cctggtccac cccaagaccg    2220
gccggctcca cacccgcttc aaccagacgg ccaccgccac gggcaggctt ccagctccg      2280 accccaacct gcagaacatc cccgtgcgca cccctctggg ccagcgcatc cgccgagcct    2340
tcgtggccga ggagggctgg gtgctggtgg tcttggacta cagccagatt gagcttcggg    2400
tcctggccca cctctccggg gacgagaacc tgatccgggt cttcaggag gggagggaca    2460 tccacaccca gaccgccagc tggatgttcg gcgttccccc gaaggggta gaccctctga     2520 tgcgccgggc ggccaagacc atcaacttcg gggtgctcta cggcatgtcc gcccaccgcc    2580
tctccgggga gctttccatc ccctacgagg aggcggtggc cttcattgag cgctacttcc    2640
agagctaccc caaggtgcgg gcctggatt aggggaccct cgaggaggc cgccggcggg     2700 ggtatgtgga gaccctcttc ggccgccggc gctatgtgcc cgacctcaac gcccgggtga    2760
agagcgtgcg cgaggcggcg gagcgcatgg ccttcaacat gccggtccag gcaccgccg    2820 ccgacctcat gaagctggcc atggtgcggc ttttcccccg gcttcaggaa ctggggcga    2880 ggatgctttt gcaggtgcac gacgagctgg tcctcgaggc ccccaaggac cgggcggaga   2940
gggtagccgc tttggccaag gaggtcatgg aggggggtctg gcccctgcag gtgcccctgg  3000
aggtggaggt gggcctgggg gaggactggc tctccgccaa ggagtag                 3047
```

<210> SEQ ID NO 8
<211> LENGTH: 831
<212> TYPE: PRT
<213> ORGANISM: Thermus flavus

<400> SEQUENCE: 8

```
Met Ala Met Leu Pro Leu Phe Glu Pro Lys Gly Arg Val Leu Leu Val
1               5                   10                  15

Asp Gly His His Leu Ala Tyr Arg Thr Phe Phe Ala Leu Lys Gly Leu
            20                  25                  30

Thr Thr Ser Arg Gly Glu Pro Val Gln Ala Val Tyr Gly Phe Ala Lys
        35                  40                  45

Ser Leu Leu Lys Ala Leu Lys Glu Asp Gly Asp Val Val Val Val
    50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95

Leu Ile Lys Glu Leu Val Asp Leu Leu Gly Leu Val Arg Leu Glu Val
```

```
                100             105              110
Pro Gly Phe Glu Ala Asp Asp Val Leu Ala Thr Leu Ala Lys Arg Ala
            115                 120             125
Glu Lys Glu Gly Tyr Glu Val Arg Ile Leu Thr Ala Asp Arg Asp Leu
            130             135                 140
Tyr Gln Leu Leu Ser Glu Arg Ile Ala Ile Leu His Pro Glu Gly Tyr
145                 150                 155                 160
Leu Ile Thr Pro Ala Trp Leu Tyr Glu Lys Tyr Gly Leu Arg Pro Glu
                165                 170             175
Gln Trp Val Asp Tyr Arg Ala Leu Ala Gly Asp Pro Ser Asp Asn Ile
                180             185                 190
Pro Gly Val Lys Gly Ile Gly Glu Lys Thr Ala Gln Arg Leu Ile Arg
                195             200             205
Glu Trp Gly Ser Leu Glu Asn Leu Phe Gln His Leu Asp Gln Val Lys
            210             215             220
Pro Ser Leu Arg Glu Lys Leu Gln Ala Gly Met Glu Ala Leu Ala Leu
225             230                 235                 240
Ser Arg Lys Leu Ser Gln Val His Thr Asp Leu Pro Leu Glu Val Asp
                245             250                 255
Phe Gly Arg Arg Arg Thr Pro Asn Leu Glu Gly Leu Arg Ala Phe Leu
                260             265             270
Glu Arg Leu Glu Phe Gly Ser Leu His Glu Phe Gly Leu Leu Glu
            275             280             285
Gly Pro Lys Ala Ala Glu Glu Ala Pro Trp Pro Pro Glu Gly Ala
            290             295             300
Phe Leu Gly Phe Ser Phe Ser Arg Pro Glu Pro Met Trp Ala Glu Leu
305             310             315                 320
Leu Ala Leu Ala Gly Ala Trp Glu Gly Arg Leu His Arg Ala Gln Asp
                325             330                 335
Pro Leu Arg Gly Leu Arg Asp Leu Lys Gly Val Arg Gly Ile Leu Ala
            340             345             350
Lys Asp Leu Ala Val Leu Ala Leu Arg Glu Gly Leu Asp Leu Phe Pro
            355             360             365
Glu Asp Asp Pro Met Leu Leu Ala Tyr Leu Leu Asp Pro Ser Asn Thr
370             375             380
Thr Pro Glu Gly Val Ala Arg Arg Tyr Gly Gly Glu Trp Thr Glu Asp
385             390             395             400
Ala Gly Glu Arg Ala Leu Leu Ala Glu Arg Leu Phe Gln Thr Leu Lys
                405             410             415
Glu Arg Leu Lys Gly Glu Glu Arg Leu Leu Trp Leu Tyr Glu Glu Val
            420             425             430
Glu Lys Pro Leu Ser Arg Val Leu Ala Arg Met Glu Ala Thr Gly Val
        435             440             445
Arg Leu Asp Val Ala Tyr Leu Gln Ala Leu Ser Leu Glu Val Glu Ala
        450             455             460
Glu Val Arg Gln Leu Glu Glu Val Phe Arg Leu Ala Gly His Pro
465             470             475             480
Phe Asn Leu Asn Ser Arg Asp Gln Leu Glu Arg Val Leu Phe Asp Glu
            485             490             495
Leu Gly Leu Pro Ala Ile Gly Lys Thr Glu Lys Thr Gly Lys Arg Ser
            500             505             510
Thr Ser Ala Ala Val Leu Glu Ala Leu Arg Glu Ala His Pro Ile Val
            515             520             525
```

```
Asp Arg Ile Leu Gln Tyr Arg Glu Leu Thr Lys Leu Lys Asn Thr Tyr
        530                 535                 540

Ile Asp Pro Leu Pro Ala Leu Val His Pro Lys Thr Gly Arg Leu His
545                 550                 555                 560

Thr Arg Phe Asn Gln Thr Ala Thr Ala Thr Gly Arg Leu Ser Ser Ser
                565                 570                 575

Asp Pro Asn Leu Gln Asn Ile Pro Val Arg Thr Pro Leu Gly Gln Arg
            580                 585                 590

Ile Arg Arg Ala Phe Val Ala Glu Glu Gly Trp Val Leu Val Val Leu
        595                 600                 605

Asp Tyr Ser Gln Ile Glu Leu Arg Val Leu Ala His Leu Ser Gly Asp
    610                 615                 620

Glu Asn Leu Ile Arg Val Phe Gln Gly Arg Asp Ile His Thr Gln
625                 630                 635                 640

Thr Ala Ser Trp Met Phe Gly Val Ser Pro Glu Gly Val Asp Pro Leu
                645                 650                 655

Met Arg Arg Ala Ala Lys Thr Ile Asn Phe Gly Val Leu Tyr Gly Met
            660                 665                 670

Ser Ala His Arg Leu Ser Gly Glu Leu Ser Ile Pro Tyr Glu Glu Ala
        675                 680                 685

Val Ala Phe Ile Glu Arg Tyr Phe Gln Ser Tyr Pro Lys Val Arg Ala
    690                 695                 700

Trp Ile Glu Gly Thr Leu Glu Glu Gly Arg Arg Arg Gly Tyr Val Glu
705                 710                 715                 720

Thr Leu Phe Gly Arg Arg Arg Tyr Val Pro Asp Leu Asn Ala Arg Val
                725                 730                 735

Lys Ser Val Arg Glu Ala Ala Glu Arg Met Ala Phe Asn Met Pro Val
            740                 745                 750

Gln Gly Thr Ala Ala Asp Leu Met Lys Leu Ala Met Val Arg Leu Phe
        755                 760                 765

Pro Arg Leu Gln Glu Leu Gly Ala Arg Met Leu Leu Gln Val His Asp
    770                 775                 780

Glu Leu Val Leu Glu Ala Pro Lys Asp Arg Ala Glu Arg Val Ala Ala
785                 790                 795                 800

Leu Ala Lys Glu Val Met Glu Gly Val Trp Pro Leu Gln Val Pro Leu
                805                 810                 815

Glu Val Glu Val Gly Leu Gly Glu Asp Trp Leu Ser Ala Lys Glu
            820                 825                 830

<210> SEQ ID NO 9
<211> LENGTH: 2502
<212> TYPE: DNA
<213> ORGANISM: Thermus filiformis

<400> SEQUENCE: 9
atgaccccac ttttttgacct ggaggaaccc cccaagcggg tgcttctggt ggacggccac      60
cacctggcct accgcacctt ctatgccctg agcctcacca cctcccgggg ggagccggtg     120
cagatggtct acggcttcgc ccggagcctc tcaaggcct tgaaggagga cggacaggcg     180
gtggtcgtgg tctttgacgc caaggccccc tccttccgcc acgaggccta cgaggcctac     240
aaggcgggcc gggcccccac cccggaggac ttccccccgcc agctcgcctt ggtcaagcgg     300
ctggtggacc ttctgggcct ggtccgcctc gaggccccgg ggtacgaggc ggacgacgtc     360
ctgggcaccc tggccaagaa ggccgaaagg gaggggatgg aggtgcgcat cctcacggga     420
gaccgggact tcttccagct cctctccgag aaggtctcgg tcctcctgcc ggacgggacc     480
```

```
ctggtcaccc caaaggacgt ccaggagaag tacggggtgc ccccggagcg ctgggtggac      540
ttccgcgccc tcacggggga ccgctcggac aacatccccg gggtggcggg gatagggag       600 aagaccgccc ttcgactcct cgcagagtgg gggagcgtgg aaaacctcct gaagaacctg      660
gaccgggtaa agccggactc gctccggcgc aagatagagg cgcacctcga ggacctccac      720
ctctccttag acctggcccg catccgcacc gacctccccc tggaggtgga ctttaaggcc      780
ctgcgccgca ggaccccga cctggagggc ctgagggcct ttttggagga gctggagttc       840
ggaagcctcc tccacgagtt cggcctcctg gaggggaga gccccggga ggaggccccc        900 tggcccccgc ccgaagggc cttcgtgggc ttcctccttt cccgcaagga gcccatgtgg       960
gcggagcttc tggccctggc ggcggcctcg gagggccggg tccaccgggc aacaagcccg     1020
gttgaggccc tggccgacct caaggaggcc cgggggttcc tggccaagga cctggccgtt     1080
ttggccctgc ggggaggggt ggccctggac cccacggacg acccctcct ggtggcctac      1140 ctcctggacc cggccaacac ccaccccgag ggggtggccc ggcgctacgg gggcgagttc     1200
acggaggacg cagcggagag ggccctcctc tccgagaggc tcttccagaa cctctttccc     1260
cggctttccg agaagctcct ctggctctac caggaggtgg agcggcccct ctcccgggtc     1320
ttggcccaca tggaggcccg gggggtgagg ctggacgtcc cccttctgga ggccctctcc     1380
tttgagctgg agaaggagat ggagcgcctg gaggggagg tcttccgttt ggccggccac      1440
cccttcaacc tcaactcccg cgaccagctg gaaagggtcc tctttgacga gctgggcctc     1500
accccggtgg gccggacgga gaagacgggc aagcgctcca ccgcccaggg ggccctggag     1560
gccctccggg gggcccaccc catcgtggag ctcatcctcc agtaccggga gctttccaag     1620
ctcaaaagca cctacctgga ccccctgccc cggctcgtcc acccgcggac gggccggctc     1680
cacacccgct caaccagac ggccacggcc acgggaaggc tttccagctc cgaccccaac      1740
ctgcagaaca tccccgtgcg caccccttg gggcagcgca tccgcaaggc cttcgtggcc      1800
gaggaggggt ggctccttt ggcggcggac tactcccaga ttgagctccg ggtcctggcc      1860
cacctctcgg gggacgagaa cctgaagcgg gtcttccggg aggggaagga catccatacc     1920
gagaccgccg cctggatgtt cggcttagac cccgctctgg tggatccaaa gatgcgccgg     1980
gcggccaaga cggtcaactt cggcgtcctc tacgggatgt ccgcccacag gctctcccag     2040
gagctcggca tagactacaa ggaggcggag gcctttattg agcgctactt ccagagcttc     2100
cccaaggtgc gggcctggat agaaaggacc ctggaggagg ccggacgcg gggctacgtg     2160 gagaccctgt tcggcaggag gcgctatgtg cccgacctgg cctcccgggt ccgctcggtg     2220
cgggaggcgg cggagcggat ggccttcaac atgcccgtgc agggcaccgc cgccgacctg     2280
atgaagatcg ccatggtcaa gctcttcccc aggctaaagc ccctgggggc ccacctcctc     2340
ctccaagtgc acgacgagct ggtcctggag gtgcccgagg accgggccga ggaggccaag     2400
gccctggtca aggaggtcat ggagaacgcc taccccctgg acgtgccct cgaggtggag      2460 gtgggcgtgg gtcgggactg gctggaggcg aagcaggatt ga                       2502
```

<210> SEQ ID NO 10
<211> LENGTH: 833
<212> TYPE: PRT
<213> ORGANISM: Thermus filiformis

<400> SEQUENCE: 10

Met Thr Pro Leu Phe Asp Leu Glu Glu Pro Pro Lys Arg Val Leu Leu
1               5                   10                  15

```
Val Asp Gly His His Leu Ala Tyr Arg Thr Phe Tyr Ala Leu Ser Leu
            20                  25                  30

Thr Thr Ser Arg Gly Glu Pro Val Gln Met Val Tyr Gly Phe Ala Arg
        35                  40                  45

Ser Leu Leu Lys Ala Leu Lys Glu Asp Gly Gln Ala Val Val Val Val
 50                  55                  60

Phe Asp Ala Lys Ala Pro Ser Phe Arg His Glu Ala Tyr Glu Ala Tyr
 65                  70                  75                  80

Lys Ala Gly Arg Ala Pro Thr Pro Glu Asp Phe Pro Arg Gln Leu Ala
                85                  90                  95

Leu Val Lys Arg Leu Val Asp Leu Leu Gly Leu Val Arg Leu Glu Ala
            100                 105                 110

Pro Gly Tyr Glu Ala Asp Asp Val Leu Gly Thr Leu Ala Lys Lys Ala
            115                 120                 125

Glu Arg Glu Gly Met Glu Val Arg Ile Leu Thr Gly Asp Arg Asp Phe
            130                 135                 140

Phe Gln Leu Leu Ser Glu Lys Val Ser Val Leu Leu Pro Asp Gly Thr
145                 150                 155                 160

Leu Val Thr Pro Lys Asp Val Gln Glu Lys Tyr Gly Val Pro Pro Glu
                165                 170                 175

Arg Trp Val Asp Phe Arg Ala Leu Thr Gly Asp Arg Ser Asp Asn Ile
            180                 185                 190

Pro Gly Val Ala Gly Ile Gly Glu Lys Thr Ala Leu Arg Leu Leu Ala
            195                 200                 205

Glu Trp Gly Ser Val Glu Asn Leu Leu Lys Asn Leu Asp Arg Val Lys
            210                 215                 220

Pro Asp Ser Leu Arg Arg Lys Ile Glu Ala His Leu Glu Asp Leu His
225                 230                 235                 240

Leu Ser Leu Asp Leu Ala Arg Ile Arg Thr Asp Leu Pro Leu Glu Val
                245                 250                 255

Asp Phe Lys Ala Leu Arg Arg Arg Thr Pro Asp Leu Glu Gly Leu Arg
            260                 265                 270

Ala Phe Leu Glu Glu Leu Glu Phe Gly Ser Leu Leu His Glu Phe Gly
            275                 280                 285

Leu Leu Gly Gly Glu Lys Pro Arg Glu Glu Ala Pro Trp Pro Pro Pro
290                 295                 300

Glu Gly Ala Phe Val Gly Phe Leu Leu Ser Arg Lys Glu Pro Met Trp
305                 310                 315                 320

Ala Glu Leu Leu Ala Leu Ala Ala Ser Glu Gly Arg Val His Arg
                325                 330                 335

Ala Thr Ser Pro Val Glu Ala Leu Ala Asp Leu Lys Glu Ala Arg Gly
            340                 345                 350

Phe Leu Ala Lys Asp Leu Ala Val Leu Ala Leu Arg Glu Gly Val Ala
            355                 360                 365

Leu Asp Pro Thr Asp Pro Leu Leu Val Ala Tyr Leu Leu Asp Pro
370                 375                 380

Ala Asn Thr His Pro Glu Gly Val Ala Arg Arg Tyr Gly Gly Glu Phe
385                 390                 395                 400

Thr Glu Asp Ala Ala Glu Arg Ala Leu Leu Ser Glu Arg Leu Phe Gln
            405                 410                 415

Asn Leu Phe Pro Arg Leu Ser Glu Lys Leu Leu Trp Leu Tyr Gln Glu
            420                 425                 430

Val Glu Arg Pro Leu Ser Arg Val Leu Ala His Met Glu Ala Arg Gly
            435                 440                 445
```

```
Val Arg Leu Asp Val Pro Leu Leu Glu Ala Leu Ser Phe Glu Leu Glu
        450                 455                 460

Lys Glu Met Glu Arg Leu Glu Gly Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Thr Pro Val Gly Arg Thr Glu Lys Thr Gly Lys Arg
                500                 505                 510

Ser Thr Ala Gln Gly Ala Leu Glu Ala Leu Arg Gly Ala His Pro Ile
            515                 520                 525

Val Glu Leu Ile Leu Gln Tyr Arg Glu Leu Ser Lys Leu Lys Ser Thr
        530                 535                 540

Tyr Leu Asp Pro Leu Pro Arg Leu Val His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Lys Ala Phe Val Ala Glu Glu Gly Trp Leu Leu Ala
        595                 600                 605

Ala Asp Tyr Ser Gln Ile Glu Leu Arg Val Leu Ala His Leu Ser Gly
610                 615                 620

Asp Glu Asn Leu Lys Arg Val Phe Arg Glu Gly Lys Asp Ile His Thr
625                 630                 635                 640

Glu Thr Ala Ala Trp Met Phe Gly Leu Asp Pro Ala Leu Val Asp Pro
                645                 650                 655

Lys Met Arg Arg Ala Ala Lys Thr Val Asn Phe Gly Val Leu Tyr Gly
                660                 665                 670

Met Ser Ala His Arg Leu Ser Gln Glu Leu Gly Ile Asp Tyr Lys Glu
            675                 680                 685

Ala Glu Ala Phe Ile Glu Arg Tyr Phe Gln Ser Phe Pro Lys Val Arg
        690                 695                 700

Ala Trp Ile Glu Arg Thr Leu Glu Glu Gly Arg Thr Arg Gly Tyr Val
705                 710                 715                 720

Glu Thr Leu Phe Gly Arg Arg Arg Tyr Val Pro Asp Leu Ala Ser Arg
                725                 730                 735

Val Arg Ser Val Arg Glu Ala Ala Glu Arg Met Ala Phe Asn Met Pro
                740                 745                 750

Val Gln Gly Thr Ala Ala Asp Leu Met Lys Ile Ala Met Val Lys Leu
            755                 760                 765

Phe Pro Arg Leu Lys Pro Leu Gly Ala His Leu Leu Leu Gln Val His
        770                 775                 780

Asp Glu Leu Val Leu Glu Val Pro Glu Asp Arg Ala Glu Glu Ala Lys
785                 790                 795                 800

Ala Leu Val Lys Glu Val Met Glu Asn Ala Tyr Pro Leu Asp Val Pro
                805                 810                 815

Leu Glu Val Glu Val Gly Val Gly Arg Asp Trp Leu Glu Ala Lys Gln
            820                 825                 830

Asp

<210> SEQ ID NO 11
<211> LENGTH: 2505
<212> TYPE: DNA
<213> ORGANISM: Thermus thermophilus
```

<400> SEQUENCE: 11

```
atggaggcga tgcttccgct ctttgaaccc aaaggccggg tcctcctggt ggacggccac        60
cacctggcct accgcacctt cttcgccctg aagggcctca ccacgagccg ggcgaaccg       120
gtgcaggcgg tctacggctt cgccaagagc ctcctcaagg ccctgaagga ggacgggtac      180
aaggccgtct tcgtggtctt tgacgccaag ccccctcct tccgccacga ggcctacgag       240
gcctacaagg cggggagggc cccgaccccc gaggacttcc cccggcagct cgccctcatc      300
aaggagctgg tggacctcct ggggtttacc cgcctcgagg tccccggcta cgaggcggac      360
gacgttctcg ccaccctggc caagaaggcg aaaaggagg ggtacgaggt gcgcatcctc       420
accgccgacc gcgacctcta ccaactcgtc tccgaccgcg tcgccgtcct ccaccccgag      480
ggccacctca tcaccccgga gtggctttgg agaagtacg gcctcaggcc ggagcagtgg       540
gtggacttcc gcgccctcgt gggggacccc tccgacaacc tccccggggt caagggcatc      600
ggggagaaga ccgccctcaa gctcctcaag gagtggggaa gcctggaaaa cctcctcaag      660
aacctggacc gggtaaagcc agaaaacgtc cgggagaaga tcaaggccca cctggaagac      720
ctcaggctct ccttggagct ctcccgggtg cgcaccgacc tcccccctgga ggtgacctc     780
gcccaggggc gggagcccga ccgggagggg cttagggcct tcctggagag ctggagttc      840
ggcagcctcc tccacgagtt cggcctcctg gaggcccccg ccccctggag ggaggccccc    900
tggcccccgc cggaaggggc cttcgtgggc ttcgtcctct cccgccccga gcccatgtgg     960
gcggagctta agccctggc cgcctgcagg acggccggg tgcaccgggc agcagacccc      1020
ttggcggggc taaggacct caaggaggtc cggggcctcc tcgccaagga cctcgccgtc     1080
ttggcctcga gggaggggct agacctcgtg cccgggacg accccatgct cctcgcctac     1140
ctcctggacc cctccaacac caccccgag ggggtggcgc ggcgctacgg ggggagtgg      1200
acggaggacg ccgcccaccg ggccctcctc tcggagaggc tccatcggaa cctccttaag    1260
cgcctcgagg gggaggagaa gctcctttgg ctctaccacg aggtggaaaa gccctctcc    1320
cgggtcctgg cccacatgga ggccaccggg gtacggcggg acgtggccta ccttcaggcc    1380
ctttccctgg agcttgcgga ggagatccgc cgcctcgagg aggaggtctt ccgcttggcg     1440
ggccaccct tcaacctcaa ctccccgggac cagctggaaa gggtgctctt tgacgagctt     1500
aggcttcccg ccttgggaa gacgcaaaag acaggcaagc gctccaccag cgccgcggtg     1560
ctggaggccc tacgggaggc ccacccccatc gtggagaaga tcctccagca ccggagctc    1620
accaagctca agaacaccta cgtggacccc ctcccaagcc tcgtccaccc gaggacgggc     1680
cgcctccaca cccgcttcaa ccagacggcc acgccacgg ggaggcttag tagctccgac     1740
cccaacctgc agaacatccc cgtccgcacc ccttgggcc agaggatccg ccgggccttc     1800
gtggccgagg cggttgggc gttggtggcc ctggactata gccagataga gctccgcgtc     1860
ctcgcccacc tctccgggga cgaaaacctg atcagggtct tccaggaggg aaggacatc     1920
cacacccaga ccgcaagctg gatgttcggc gtccccccgg aggccgtgga cccctgatg    1980
cgccgggcgg ccaagacggt gaacttcggc gtcctctacg catgtccgc ccataggctc     2040
tcccaggagc ttgccatccc ctacgaggag gcggtggcct ttatagagcg ctacttccaa    2100
agcttccccca aggtgcgggc ctggatagaa aagaccctgg aggagggag gaagcggggc     2160
tacgtggaaa ccctcttcgg aagaaggcgc tacgtgcccg acctcaacgc ccgggtgaag    2220
agcgtcagga ggccgcgga gcgcatggcc ttcaacatgc ccgtccaggg caccgccgcc     2280
gacctcatga agctcgccat ggtgaagctc ttccccccgcc tccgggagat gggggcccgc    2340
```

```
atgctcctcc aggtccacga cgagctcctc ctggaggccc cccaagcgcg ggccgaggag    2400
gtggcggctt tggccaagga ggccatggag aaggcctatc ccctcgccgt gcccctggag    2460
gtggaggtgg ggatggggga ggactggctt tccgccaagg gttag                   2505
```

<210> SEQ ID NO 12
<211> LENGTH: 834
<212> TYPE: PRT
<213> ORGANISM: Thermus thermophilus

<400> SEQUENCE: 12

```
Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu Ala Pro Ala Pro Leu Glu Glu Ala Pro Trp Pro Pro Pro
    290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350
```

Leu Leu Ala Lys Asp Leu Ala Val Leu Ala Ser Arg Glu Gly Leu Asp
        355                 360                 365
Leu Val Pro Gly Asp Pro Met Leu Leu Ala Tyr Leu Leu Asp Pro
        370                 375                 380
Ser Asn Thr Thr Pro Glu Gly Val Ala Arg Arg Tyr Gly Gly Glu Trp
385                 390                 395                 400
Thr Glu Asp Ala Ala His Arg Ala Leu Leu Ser Glu Arg Leu His Arg
                405                 410                 415
Asn Leu Leu Lys Arg Leu Glu Gly Glu Lys Leu Leu Trp Leu Tyr
            420                 425                 430
His Glu Val Glu Lys Pro Leu Ser Arg Val Leu Ala His Met Glu Ala
        435                 440                 445
Thr Gly Val Arg Arg Asp Val Ala Tyr Leu Gln Ala Leu Ser Leu Glu
        450                 455                 460
Leu Ala Glu Glu Ile Arg Arg Leu Glu Glu Val Phe Arg Leu Ala
465                 470                 475                 480
Gly His Pro Phe Asn Leu Asn Ser Arg Asp Gln Leu Glu Arg Val Leu
                485                 490                 495
Phe Asp Glu Leu Arg Leu Pro Ala Leu Gly Lys Thr Gln Lys Thr Gly
            500                 505                 510
Lys Arg Ser Thr Ser Ala Ala Val Leu Glu Ala Leu Arg Glu Ala His
        515                 520                 525
Pro Ile Val Glu Lys Ile Leu Gln His Arg Glu Leu Thr Lys Leu Lys
        530                 535                 540
Asn Thr Tyr Val Asp Pro Leu Pro Ser Leu Val His Pro Arg Thr Gly
545                 550                 555                 560
Arg Leu His Thr Arg Phe Asn Gln Thr Ala Thr Ala Thr Gly Arg Leu
                565                 570                 575
Ser Ser Ser Asp Pro Asn Leu Gln Asn Ile Pro Val Arg Thr Pro Leu
            580                 585                 590
Gly Gln Arg Ile Arg Arg Ala Phe Val Ala Glu Ala Gly Trp Ala Leu
        595                 600                 605
Val Ala Leu Asp Tyr Ser Gln Ile Glu Leu Arg Val Leu Ala His Leu
        610                 615                 620
Ser Gly Asp Glu Asn Leu Ile Arg Val Phe Gln Glu Gly Lys Asp Ile
625                 630                 635                 640
His Thr Gln Thr Ala Ser Trp Met Phe Gly Val Pro Pro Glu Ala Val
                645                 650                 655
Asp Pro Leu Met Arg Arg Ala Ala Lys Thr Val Asn Phe Gly Val Leu
            660                 665                 670
Tyr Gly Met Ser Ala His Arg Leu Ser Gln Glu Leu Ala Ile Pro Tyr
        675                 680                 685
Glu Glu Ala Val Ala Phe Ile Glu Arg Tyr Phe Gln Ser Phe Pro Lys
        690                 695                 700
Val Arg Ala Trp Ile Glu Lys Thr Leu Glu Glu Gly Arg Lys Arg Gly
705                 710                 715                 720
Tyr Val Glu Thr Leu Phe Gly Arg Arg Arg Tyr Val Pro Asp Leu Asn
                725                 730                 735
Ala Arg Val Lys Ser Val Arg Glu Ala Ala Glu Arg Met Ala Phe Asn
            740                 745                 750
Met Pro Val Gln Gly Thr Ala Ala Asp Leu Met Lys Leu Ala Met Val
        755                 760                 765
Lys Leu Phe Pro Arg Leu Arg Glu Met Gly Ala Arg Met Leu Leu Gln

```
                770                 775                 780
Val His Asp Glu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly

<210> SEQ ID NO 13
<211> LENGTH: 166
<212> TYPE: PRT
<213> ORGANISM: Thermus flavus

<400> SEQUENCE: 13

Glu Leu Arg Val Leu Ala His Leu Ser Gly Asp Glu Asn Leu Ile Arg
1               5                   10                  15

Val Phe Gln Glu Gly Arg Asp Ile His Thr Gln Thr Ala Ser Trp Met
            20                  25                  30

Phe Gly Val Ser Pro Glu Gly Val Asp Pro Leu Met Arg Arg Ala Ala
        35                  40                  45

Lys Thr Ile Asn Phe Gly Val Leu Tyr Gly Met Ser Ala His Arg Leu
    50                  55                  60

Ser Gly Glu Leu Ser Ile Pro Tyr Glu Glu Ala Val Ala Phe Ile Glu
65                  70                  75                  80

Arg Tyr Phe Gln Ser Tyr Pro Lys Val Arg Ala Trp Ile Glu Gly Thr
                85                  90                  95

Leu Glu Glu Gly Arg Arg Arg Gly Tyr Val Glu Thr Leu Phe Gly Arg
            100                 105                 110

Arg Arg Tyr Val Pro Asp Leu Asn Ala Arg Val Lys Ser Val Arg Glu
        115                 120                 125

Ala Ala Glu Arg Met Ala Phe Asn Met Pro Val Gln Gly Thr Ala Ala
    130                 135                 140

Asp Leu Met Lys Leu Ala Met Val Arg Leu Phe Pro Arg Leu Gln Glu
145                 150                 155                 160

Leu Gly Ala Arg Met Leu
                165

<210> SEQ ID NO 14
<211> LENGTH: 166
<212> TYPE: PRT
<213> ORGANISM: Thermus filiformis

<400> SEQUENCE: 14

Glu Leu Arg Val Leu Ala His Leu Ser Gly Asp Glu Asn Leu Lys Arg
1               5                   10                  15

Val Phe Arg Glu Gly Lys Asp Ile His Thr Glu Thr Ala Ala Trp Met
            20                  25                  30

Phe Gly Leu Asp Pro Ala Leu Val Asp Pro Lys Met Arg Arg Ala Ala
        35                  40                  45

Lys Thr Val Asn Phe Gly Val Leu Tyr Gly Met Ser Ala His Arg Leu
    50                  55                  60

Ser Gln Glu Leu Gly Ile Asp Tyr Lys Glu Ala Ala Phe Ile Glu
65                  70                  75                  80

Arg Tyr Phe Gln Ser Phe Pro Lys Val Arg Ala Trp Ile Glu Arg Thr
                85                  90                  95
```

```
Leu Glu Glu Gly Arg Thr Arg Gly Tyr Val Glu Thr Leu Phe Gly Arg
                100                 105                 110

Arg Arg Tyr Val Pro Asp Leu Ala Ser Arg Val Arg Ser Val Arg Glu
            115                 120                 125

Ala Ala Glu Arg Met Ala Phe Asn Met Pro Val Gln Gly Thr Ala Ala
        130                 135                 140

Asp Leu Met Lys Ile Ala Met Val Lys Leu Phe Pro Arg Leu Lys Pro
145                 150                 155                 160

Leu Gly Ala His Leu Leu
                165

<210> SEQ ID NO 15
<211> LENGTH: 166
<212> TYPE: PRT
<213> ORGANISM: Thermus thermophilus

<400> SEQUENCE: 15

Glu Leu Arg Val Leu Ala His Leu Ser Gly Asp Glu Asn Leu Ile Arg
1               5                   10                  15

Val Phe Gln Glu Gly Lys Asp Ile His Thr Gln Thr Ala Ser Trp Met
            20                  25                  30

Phe Gly Val Pro Pro Glu Ala Val Asp Pro Leu Met Arg Arg Ala Ala
        35                  40                  45

Lys Thr Val Asn Phe Gly Val Leu Tyr Gly Met Ser Ala His Arg Leu
 50                 55                  60

Ser Gln Glu Leu Ala Ile Pro Tyr Glu Glu Ala Val Ala Phe Ile Glu
65                  70                  75                  80

Arg Tyr Phe Gln Ser Phe Pro Lys Val Arg Ala Trp Ile Glu Lys Thr
                85                  90                  95

Leu Glu Glu Gly Arg Lys Arg Gly Tyr Val Glu Thr Leu Phe Gly Arg
                100                 105                 110

Arg Arg Tyr Val Pro Asp Leu Asn Ala Arg Val Lys Ser Val Arg Glu
            115                 120                 125

Ala Ala Glu Arg Met Ala Phe Asn Met Pro Val Gln Gly Thr Ala Ala
        130                 135                 140

Asp Leu Met Lys Leu Ala Met Val Lys Leu Phe Pro Arg Leu Arg Glu
145                 150                 155                 160

Met Gly Ala Arg Met Leu
                165

<210> SEQ ID NO 16
<211> LENGTH: 166
<212> TYPE: PRT
<213> ORGANISM: Thermus aquaticus

<400> SEQUENCE: 16

Glu Leu Arg Val Leu Ala His Leu Ser Gly Asp Glu Asn Leu Ile Arg
1               5                   10                  15

Val Phe Gln Glu Gly Arg Asp Ile His Thr Glu Thr Ala Ser Trp Met
            20                  25                  30

Phe Gly Val Pro Arg Glu Ala Val Asp Pro Leu Met Arg Arg Ala Ala
        35                  40                  45

Lys Thr Ile Asn Phe Gly Val Leu Tyr Gly Met Ser Ala His Arg Leu
 50                 55                  60

Ser Gln Glu Leu Ala Ile Pro Tyr Glu Glu Ala Gln Ala Phe Ile Glu
65                  70                  75                  80

Arg Tyr Phe Gln Ser Phe Pro Lys Val Arg Ala Trp Ile Glu Lys Thr
```

```
                     85                  90                  95
Leu Glu Glu Gly Arg Arg Gly Tyr Val Glu Thr Leu Phe Gly Arg
                100                 105                 110

Arg Arg Tyr Val Pro Asp Leu Glu Ala Arg Val Lys Ser Val Arg Glu
                115                 120                 125

Ala Ala Glu Arg Met Ala Phe Asn Met Pro Val Gln Gly Thr Ala Ala
            130                 135                 140

Asp Leu Met Lys Leu Ala Met Val Lys Leu Phe Pro Arg Leu Glu Glu
145                 150                 155                 160

Met Gly Ala Arg Met Leu
                165

<210> SEQ ID NO 17
<211> LENGTH: 166
<212> TYPE: PRT
<213> ORGANISM: Thermus eggertssonii

<400> SEQUENCE: 17

Glu Leu Arg Val Leu Ala His Leu Ser Gly Asp Glu Asn Leu Ile Arg
1               5                   10                  15

Val Phe Gln Glu Gly Arg Asp Ile His Thr Gln Thr Ala Ser Trp Met
                20                  25                  30

Phe Gly Leu Pro Ala Glu Ala Ile Asp Pro Leu Arg Arg Arg Ala Ala
            35                  40                  45

Lys Thr Ile Asn Phe Gly Val Leu Tyr Gly Met Ser Ala His Arg Leu
        50                  55                  60

Ser Gln Glu Leu Gly Ile Pro Tyr Glu Glu Ala Val Ala Phe Ile Asp
65                  70                  75                  80

Arg Tyr Phe Gln Ser Tyr Pro Lys Val Lys Ala Trp Ile Glu Arg Thr
                85                  90                  95

Leu Glu Glu Gly Arg Gln Arg Gly Tyr Val Glu Thr Leu Phe Gly Arg
                100                 105                 110

Arg Arg Tyr Val Pro Asp Leu Asn Ala Arg Val Lys Ser Val Arg Glu
                115                 120                 125

Ala Ala Glu Arg Met Ala Phe Asn Met Pro Val Gln Gly Thr Ala Ala
            130                 135                 140

Val Leu Met Lys Leu Ala Met Val Arg Leu Phe Pro Arg Leu Pro Glu
145                 150                 155                 160

Val Gly Ala Arg Met Leu
                165

<210> SEQ ID NO 18
<211> LENGTH: 166
<212> TYPE: PRT
<213> ORGANISM: Thermus eggertssonii

<400> SEQUENCE: 18

Glu Leu Arg Val Leu Ala His Leu Ser Gly Asp Glu Asn Leu Ile Gln
1               5                   10                  15

Val Phe Gln Glu Gly Arg Asp Ile His Thr Gln Thr Ala Ser Trp Met
                20                  25                  30

Phe Gly Leu Pro Ala Glu Ala Ile Asp Pro Leu Met Arg Arg Ala Ala
            35                  40                  45

Lys Thr Ile Asn Phe Gly Val Leu Tyr Gly Met Ser Ala His Arg Leu
        50                  55                  60

Ser Gln Glu Leu Ser Ile Pro Tyr Glu Glu Ala Val Ala Phe Ile Asp
65                  70                  75                  80
```

```
Arg Tyr Phe Gln Ser Tyr Pro Lys Val Lys Ala Trp Ile Glu Arg Thr
                85                  90                  95

Leu Glu Glu Gly Arg Gln Arg Gly Tyr Val Glu Thr Leu Phe Gly Arg
            100                 105                 110

Arg Arg Tyr Val Pro Asp Leu Asn Ala Arg Val Lys Ser Val Arg Glu
        115                 120                 125

Ala Ala Glu Arg Met Ala Phe Asn Met Pro Val Gln Gly Thr Ala Ala
    130                 135                 140

Asp Leu Met Lys Leu Ala Met Val Arg Leu Phe Pro Arg Leu Pro Glu
145                 150                 155                 160

Val Gly Ala Arg Met Leu
                165

<210> SEQ ID NO 19
<211> LENGTH: 166
<212> TYPE: PRT
<213> ORGANISM: Thermus eggertssonii

<400> SEQUENCE: 19

Glu Leu Arg Val Leu Ala His Leu Ser Gly Asp Glu Asn Leu Ile Gln
1               5                   10                  15

Val Phe Gln Glu Gly Arg Asp Ile His Thr Gln Thr Ala Ser Trp Met
            20                  25                  30

Phe Gly Leu Pro Ala Glu Ala Ile Asp Pro Leu Met Arg Arg Ala Ala
        35                  40                  45

Lys Thr Ile Asn Phe Gly Val Leu Tyr Gly Met Ser Ala His Arg Leu
    50                  55                  60

Ser Gln Glu Leu Ser Ile Pro Tyr Glu Glu Ala Val Ala Phe Ile Asp
65                  70                  75                  80

Arg Tyr Phe Gln Ser Tyr Pro Lys Val Lys Ala Trp Ile Glu Arg Thr
                85                  90                  95

Leu Glu Glu Gly Arg Gln Arg Gly Tyr Val Glu Thr Leu Phe Gly Arg
            100                 105                 110

Arg Arg Tyr Val Pro Asp Leu Asn Ala Arg Val Lys Ser Val Arg Glu
        115                 120                 125

Ala Ala Glu Arg Met Ala Phe Asn Met Pro Val Gln Gly Thr Ala Ala
    130                 135                 140

Asp Leu Met Lys Leu Ala Met Val Arg Leu Phe Pro Arg Leu Pro Glu
145                 150                 155                 160

Val Gly Ala Arg Met Leu
                165

<210> SEQ ID NO 20
<211> LENGTH: 166
<212> TYPE: PRT
<213> ORGANISM: Thermus eggertssonii

<400> SEQUENCE: 20

Glu Leu Arg Val Leu Ala His Leu Ser Gly Asp Glu Asn Leu Ile Gln
1               5                   10                  15

Val Phe Gln Glu Gly Arg Asp Ile His Thr Gln Thr Ala Ser Trp Met
            20                  25                  30

Phe Gly Leu Pro Ala Glu Ala Ile Asp Pro Leu Met Arg Arg Ala Ala
        35                  40                  45

Lys Thr Ile Asn Phe Gly Val Leu Tyr Gly Met Ser Ala His Arg Leu
    50                  55                  60
```

```
Ser Gln Glu Leu Ser Ile Pro Tyr Glu Glu Ala Val Ala Phe Ile Asp
 65                  70                  75                  80

Arg Tyr Phe Gln Ser Tyr Pro Lys Val Lys Ala Trp Ile Glu Arg Thr
                 85                  90                  95

Leu Glu Glu Gly Arg Gln Arg Gly Tyr Val Glu Thr Leu Phe Gly Arg
             100                 105                 110

Arg Arg Tyr Val Pro Asp Leu Asn Ala Arg Val Lys Ser Val Arg Glu
         115                 120                 125

Ala Ala Glu Arg Met Ala Phe Asn Met Pro Val Gln Gly Thr Ala Ala
     130                 135                 140

Asp Leu Met Lys Leu Ala Met Val Arg Leu Phe Pro Arg Leu Pro Glu
145                 150                 155                 160

Val Gly Ala Arg Met Leu
                165

<210> SEQ ID NO 21
<211> LENGTH: 166
<212> TYPE: PRT
<213> ORGANISM: Thermus eggertssonii

<400> SEQUENCE: 21

Glu Leu Arg Val Leu Ala His Leu Ser Gly Asp Glu Asn Leu Ile Gln
1               5                  10                  15

Val Phe Gln Glu Gly Arg Asp Ile His Thr Gln Thr Ala Ser Trp Met
                 20                  25                  30

Phe Gly Leu Pro Ala Glu Ala Ile Asn Pro Leu Met Arg Arg Ala Ala
             35                  40                  45

Lys Thr Ile Asn Phe Gly Val Leu Tyr Gly Met Ser Ala His Arg Leu
 50                  55                  60

Ser Gln Glu Leu Ser Ile Pro Tyr Glu Glu Ala Val Ala Phe Ile Asp
 65                  70                  75                  80

Arg Tyr Phe Gln Ser Tyr Pro Lys Val Lys Ala Trp Ile Glu Arg Thr
                 85                  90                  95

Leu Glu Glu Gly Arg Gln Arg Gly Tyr Val Glu Thr Leu Phe Gly Arg
             100                 105                 110

Arg Arg Tyr Val Pro Asp Leu Asn Ala Arg Val Lys Ser Val Arg Glu
         115                 120                 125

Ala Ala Glu Arg Met Ala Phe Asn Met Pro Val Gln Gly Thr Ala Ala
     130                 135                 140

Asp Leu Met Lys Leu Ala Met Val Arg Leu Phe Pro Arg Leu Pro Glu
145                 150                 155                 160

Val Gly Ala Arg Met Leu
                165

<210> SEQ ID NO 22
<211> LENGTH: 166
<212> TYPE: PRT
<213> ORGANISM: Thermus eggertssonii

<400> SEQUENCE: 22

Glu Leu Arg Val Leu Ala His Leu Ser Gly Asp Glu Asn Leu Ile Gln
1               5                  10                  15

Val Phe Gln Glu Gly Arg Asp Ile His Thr Gln Thr Ala Ser Trp Met
                 20                  25                  30

Phe Gly Leu Pro Ala Glu Ala Ile Asn Pro Leu Met Arg Arg Ala Ala
             35                  40                  45

Lys Thr Ile Asn Phe Gly Val Leu Tyr Gly Met Ser Ala His Arg Leu
```

```
                50                  55                  60

Ser Gln Glu Leu Ser Ile Pro Tyr Glu Ala Val Ala Phe Ile Asp
65                  70                  75                  80

Arg Tyr Phe Gln Ser Tyr Pro Lys Val Lys Ala Trp Ile Glu Arg Thr
                85                  90                  95

Leu Glu Glu Gly Arg Gln Arg Gly Tyr Val Glu Thr Leu Phe Gly Arg
                100                 105                 110

Arg Arg Tyr Val Pro Asp Leu Asn Ala Arg Val Lys Ser Val Arg Glu
                115                 120                 125

Ala Ala Glu Arg Met Ala Phe Asn Met Pro Val Gln Gly Thr Ala Ala
                130                 135                 140

Asp Leu Met Lys Leu Ala Met Val Arg Leu Phe Pro Arg Leu Pro Glu
145                 150                 155                 160

Val Gly Ala Arg Met Leu
                165

<210> SEQ ID NO 23
<211> LENGTH: 166
<212> TYPE: PRT
<213> ORGANISM: Thermus eggertssonii

<400> SEQUENCE: 23

Glu Leu Arg Val Leu Ala His Leu Ser Gly Asp Glu Asn Leu Ile Gln
1               5                   10                  15

Val Phe Gln Glu Gly Arg Asp Ile His Thr Gln Thr Ala Ser Trp Met
                20                  25                  30

Phe Gly Leu Pro Ala Glu Ala Ile Asn Pro Leu Met Arg Arg Ala Ala
                35                  40                  45

Lys Thr Ile Asn Phe Gly Val Leu Tyr Gly Met Ser Ala His Arg Leu
50                  55                  60

Ser Gln Glu Leu Ser Ile Pro Tyr Glu Ala Val Ala Phe Ile Asp
65                  70                  75                  80

Arg Tyr Phe Gln Ser Tyr Pro Lys Val Lys Ala Trp Ile Glu Arg Thr
                85                  90                  95

Leu Glu Glu Gly Arg Gln Arg Gly Tyr Val Glu Thr Leu Phe Gly Arg
                100                 105                 110

Arg Arg Tyr Val Pro Asp Leu Asn Ala Arg Val Lys Ser Val Arg Glu
                115                 120                 125

Ala Ala Glu Arg Met Ala Phe Asn Met Pro Val Gln Gly Thr Ala Ala
                130                 135                 140

Asp Leu Met Lys Leu Ala Met Val Arg Leu Phe Pro Arg Leu Pro Glu
145                 150                 155                 160

Val Gly Ala Arg Met Leu
                165

<210> SEQ ID NO 24
<211> LENGTH: 423
<212> TYPE: DNA
<213> ORGANISM: Thermus eggertssonii

<400> SEQUENCE: 24
acgggcccca ctcctacggg aggcagcagt taggaatctt ccgcaatggg cgcaagcctg      60
acggagcgac gccgcttgga ggaggaagcc cttcgggtg taaactcctg aactggggac     120
gaaagccccg atgaggggga tgacggtacc caggtaatag cgccggccaa ctccgtgcca    180
gcagccgcgg taatacggag ggcgcgagcg ttacccggat ttactgggcg taaagggcgt    240
```

```
gtaggcggct tggggcgtcc catgtgaaag accacggctc aaccgtgggg gagcgtggga    300
tacgctcagg ctagacggcg ggaggggtg gtggaattcc cggagtagcg gtgaaatgcg    360
cagacaccgg gaggaacgcc gatagcgaag gcagccacct ggctcgttcg tgacgatgag    420
gcg                                                                 423

<210> SEQ ID NO 25
<211> LENGTH: 424
<212> TYPE: DNA
<213> ORGANISM: Thermus eggertssonii

<400> SEQUENCE: 25
acgggcccca ctcctacggg aggcagcagt taggaatctt ccgcaatggg cgcaagcctg     60
acggaacgac gccgcttgga ggaggaaagc cttcggggtg taaactcctg aactggggac    120
gaaagccctg atgaggggga tgacggtacc caggtaatag cgccggccaa ctccgtgcca    180
gcagccgcgg taatacgag ggcgcgagcg ttacccggat ttactgggcg taaagggcgt    240
gtaggcggtc tggggcgtcc catgtgaaag accacggctc aaccgtgggg gagcgtggga    300
tacgctcagg ctagacggcg ggagagggtg gtggaattcc cggagtagcg gtgaaatgcg    360
cagataccgg gaggaacgcc gatggcgaag gcagccacct ggctcgttcg tgcccgctga    420
ggcg                                                                424

<210> SEQ ID NO 26
<211> LENGTH: 423
<212> TYPE: DNA
<213> ORGANISM: Thermus eggertssonii

<400> SEQUENCE: 26
acgggcccca ctcctacggg aggcagcagt taggaatctt ccgcaatggg cgcaagcctg     60
acggagcgac gccgcttgga ggaggaagcc cttcggggtg taaactcctg aactggggac    120
gaaagccctg atgaggggga tgacggtacc caggtaatag cgccggccaa ctccgtgcca    180
gcagccgcgg taatacgag ggcgcgagcg ttacccggat ttactgggcg taaagggcgt    240
gtaggcggtc tggggcgtcc catgtgaaag accacggctc aaccgtgggg gagcgtggga    300
tacgctcagg ctagacggcg ggagagggtg gtggaattcc cggagtagcg gtgaaatgcg    360
cagataccgg gaggaacgcc gatggcgaag gcagccacct ggctcgttcg tgacgctgag    420
gcg                                                                 423

<210> SEQ ID NO 27
<211> LENGTH: 423
<212> TYPE: DNA
<213> ORGANISM: Thermus eggertssonii

<400> SEQUENCE: 27
acgggcccca ctcctacggg aggcagcagt taggaatctt ccgcaatggg cgcaagcctg     60
acggagcgac gccgcttgga ggaggaagcc cttcggggtg taaactcctg aactggggac    120
gaaagccctg atgaggggga tgacggtacc caggtaatag cgccggccaa ctccgtgcca    180
gcagccgcgg taatacgag ggcgcgagcg ttacccggat ttactgggcg taaagggcgt    240
gtaggcggtc tggggcgtcc catgtgaaag accacggctc aaccgtgggg gagcgtggga    300
tacgctcagg ctagacggcg ggagagggtg gtggaattcc cggagtagcg gtgaaatgcg    360
cagataccgg gaggaacgcc gatggcgaag gcagccacct ggctcgttcg tgacgctgag    420
gcg                                                                 423
```

```
<210> SEQ ID NO 28
<211> LENGTH: 423
<212> TYPE: DNA
<213> ORGANISM: Thermus aquaticus

<400> SEQUENCE: 28
acgggcccca ctcctacggg aggcagcagt taggaatctt ccgcaatggg cgcaagcctg      60
acggagcgac gccgcttgga ggaggaagcc cttcggggtg taaactcctg aacccgggac     120 gaaaccccg atgaggggac tgacggtacc ggggtaatag cgccggccaa ctccgtgcca     180
gcagccgcgg taatacgag ggcgcgagcg ttacccggat ttactgggcg taaagggcgt     240
gtaggcggct tggggcgtcc catgtgaaag gccacggctc aaccgtggag gagcgtggga     300
tacgctcagg ctagcggtg ggagagggtg gtggaattcc cggagtagcg gtgaaatgcg     360
cagataccgg gaggaacgcc gatggcgaag gcagccacct ggtccactcg tgacgctgag     420
gcg                                                                   423

<210> SEQ ID NO 29
<211> LENGTH: 423
<212> TYPE: DNA
<213> ORGANISM: Thermus thermophilus

<400> SEQUENCE: 29
acgggcccca ctcctacggg aggcagcagt taggaatctt ccgcaatggg cgcaagcctg      60
acggagcgac gccgcttgga ggaagaagcc cttcggggtg taaactcctg aacccgggac     120 gaaaccccg acgaggggac tgacggtacc ggggtaatag cgccggccaa ctccgtgcca     180
gcagccgcgg taatacgag ggcgcgagcg ttacccggat tcactgggcg taaagggcgt     240
gtaggcggcc tggggcgtcc catgtgaaag accacggctc aaccgtgggg gagcgtggga     300
tacgctcagg ctagcggtg ggagagggtg gtggaattcc cggagtagcg gtgaaatgcg     360
cagataccgg gaggaacgcc gatggcgaag gcagccacct ggtccacccg tgacgctgag     420
gcg                                                                   423

<210> SEQ ID NO 30
<211> LENGTH: 423
<212> TYPE: DNA
<213> ORGANISM: Thermus brockianus

<400> SEQUENCE: 30
acgggcccca ctcctacggg aggcagcagt taggaatctt ccgcaatggg cgcaagcctg      60
acggagcgac gccgcttgga ggaggaagcc cttcggggtg taaactcctg aactggggac     120
gaaagccccg atgaggggga tgacggtacc caggtaatag cgccggccaa ctccgtgcca     180
gcagccgcgg taatacgag ggcgcgagcg ttacccggat ttactgggcg taaagggcgt     240
gtaggcggct tggggcgtcc catgtgaaag accacggctc aaccgtgggg gagcgtggga     300
tacgctcagg ctagacggcg ggaggggtg gtggaattcc cggagtagcg gtgaaatgcg     360
cagataccgg gaggaacgcc gatagcgaag gcagccacct ggctcgttcg tgacgctgag     420
gcg                                                                   423

<210> SEQ ID NO 31
<211> LENGTH: 423
<212> TYPE: DNA
<213> ORGANISM: Thermus ignitarrae

<400> SEQUENCE: 31
```

-continued

```
acgggcccca ctcctacggg aggcagcagt taggaatctt ccgcaatgga cggaagtctg      60
acggagcgac gccgcttgga ggaggaagcc cttcggggtg taaactcctg aactggggac     120
gaaagccctg atgaggggga tgacggtacc caggtaatag cgccggccaa ctccgtgcca     180
gcagccgcgg taatacggag ggcgcgagcg ttacccggat ttactgggcg taaagggcgt     240
gtaggcggtc tggggcgtcc catgtgaaag accacggctc aaccgtgggg gagcgtggga     300
tacgctcagg ctagcggcg ggaggggtg gtggaattcc cggagtagcg gtgaaatgcg      360
cagataccgg gaggaacgcc gatggcgaag gcagccacct ggctcgttcg tgacgctgag     420
gcg                                                                   423

<210> SEQ ID NO 32
<211> LENGTH: 423
<212> TYPE: DNA
<213> ORGANISM: Thermus antranikianus

<400> SEQUENCE: 32
acgggcccca ctcctacggg aggcagcagt taggaatctt ccgcaatggg cggaagcctg      60
acggagcgac gccgcttgga ggaggaagcc cttcggggtg taaactcctg aactggggac     120
gaaagccccg ataggggga tgacggtacc caggtaatag cgccggccaa ctccgtgcca      180
gcagccgcgg taatacggag ggcgcgagcg ttacccggat ttactgggcg taaagggcgt     240
gtaggcggct tggggcgtcc catgtgaaag accacggctc aaccgtgggg gagcgtggga     300
tacgctcaag ctagggggtg ggagagggtg gtggaattcc cggagtagcg gtgaaatgcg     360
cagataccgg gaggaacgcc gatggcgaag gcagccacct ggtccacttc tgacgctgag     420
gcg                                                                   423

<210> SEQ ID NO 33
<211> LENGTH: 423
<212> TYPE: DNA
<213> ORGANISM: Thermus scotoductus

<400> SEQUENCE: 33
acgggcccca ctcctacggg aggcagcagt taggaatctt ccgcaatgga cggaagtctg      60
acggagcgac gccgcttgga ggaggaagcc cttcggggtg taaactcctg aactggggac     120
gaaagccctg tgtaggggga tgacggtacc caggtaatag cgccggccaa ctccgtgcca     180
gcagccgcgg taatacggag ggcgcgagcg ttacccggat ttactgggcg taaagggcgt     240
gtaggcggcc tggggcgtcc catgtgaaag gccacggctc aaccgtggag gagcgtggga     300
tacgctcagg ctagggggtg ggagagggtg gtggaattcc cggagtagcg gtgaaatgcg     360
cagataccgg gaggaacgcc gatggcgaag gcagccacct ggtccacttc tgacgctgag     420
gcg                                                                   423

<210> SEQ ID NO 34
<211> LENGTH: 423
<212> TYPE: DNA
<213> ORGANISM: Thermus oshimai

<400> SEQUENCE: 34
acgggcccca ctcctacggg aggcagcagt taggaatctt ccgcaatggg cgaaagcctg      60
acggagcgac gccgcttgcg ggacgaagcc cctcggggtg taaaccgctg aacctgggac     120
gaaaaccccc acaaggggac tgacggtacc agggtaatag cgccggccaa ctccgtgcca     180
gcagccgcgg taatacggag ggcgcaagcg ttacccggat tcactgggcg taaagggcgt     240
```

```
gtaggcggcc cggggcgtcc ggcgttaaag cccacggctc aaccgtggaa ccgcgccgga   300
tacgcccggg ctagacggcg ggagagggtg gtggaattcc cggagtagcg gtgaaatgcg   360
cagataccgg gaggaacgcc aatggcgaag gcagccacct ggcccgcccg tgacgctgag   420
gcg                                                                 423
```

<210> SEQ ID NO 35
<211> LENGTH: 22
<212> TYPE: DNA
<213> ORGANISM: Artificial
<220> FEATURE:
<223> OTHER INFORMATION: Example
<220> FEATURE:
<221> NAME/KEY: misc_feature
<222> LOCATION: (9)..(9)
<223> OTHER INFORMATION: n is a, c, g, t or u
<220> FEATURE:
<221> NAME/KEY: misc_feature
<222> LOCATION: (21)..(21)
<223> OTHER INFORMATION: n is a, c, g, t or u

<400> SEQUENCE: 35

```
tcgaattcnc cyaaytgrcc nt                                             22
```

<210> SEQ ID NO 36
<211> LENGTH: 26
<212> TYPE: DNA
<213> ORGANISM: Artificial
<220> FEATURE:
<223> OTHER INFORMATION: Example

<400> SEQUENCE: 36

```
gccgccgact actcccarat hgarht                                         26
```

<210> SEQ ID NO 37
<211> LENGTH: 27
<212> TYPE: DNA
<213> ORGANISM: Artificial
<220> FEATURE:
<223> OTHER INFORMATION: Example
<220> FEATURE:
<221> NAME/KEY: misc_feature
<222> LOCATION: (25)..(25)
<223> OTHER INFORMATION: n is a, c, g, t or u

<400> SEQUENCE: 37

```
gccctcgaac accatctcrt crtgnac                                        27
```

<210> SEQ ID NO 38
<211> LENGTH: 35
<212> TYPE: DNA
<213> ORGANISM: Artificial
<220> FEATURE:
<223> OTHER INFORMATION: Example
<220> FEATURE:
<221> NAME/KEY: misc_feature
<222> LOCATION: (21)..(30)
<223> OTHER INFORMATION: n is a, c, g, t or u

<400> SEQUENCE: 38

```
ggccacgcgt cgactagtac nnnnnnnnnn gatat                               35
```

<210> SEQ ID NO 39
<211> LENGTH: 35
<212> TYPE: DNA
<213> ORGANISM: Artificial
<220> FEATURE:
<223> OTHER INFORMATION: Example
<220> FEATURE:

-continued

```
<221> NAME/KEY: misc_feature
<222> LOCATION: (21)..(30)
<223> OTHER INFORMATION: n is a, c, g, t or u

<400> SEQUENCE: 39
ggccacgcgt cgactagtac nnnnnnnnnn acgcc                              35

<210> SEQ ID NO 40
<211> LENGTH: 20
<212> TYPE: DNA
<213> ORGANISM: Artificial
<220> FEATURE:
<223> OTHER INFORMATION: Example

<400> SEQUENCE: 40
ggccacgcgt cgactagtac                                              20

<210> SEQ ID NO 41
<211> LENGTH: 24
<212> TYPE: DNA
<213> ORGANISM: Artificial
<220> FEATURE:
<223> OTHER INFORMATION: Primer

<400> SEQUENCE: 41
agcggataac aatttcacac agga                                         24

<210> SEQ ID NO 42
<211> LENGTH: 21
<212> TYPE: DNA
<213> ORGANISM: Artificial
<220> FEATURE:
<223> OTHER INFORMATION: Primer R805

<400> SEQUENCE: 42
gactacccgg gtatctaatc c                                            21

<210> SEQ ID NO 43
<211> LENGTH: 2505
<212> TYPE: DNA
<213> ORGANISM: Thermus eggertssonii

<400> SEQUENCE: 43
atgggccgtg gtatgctgcc gctgtttgaa ccgaaaggcc gtgtgctgct ggttgatggc    60
caccatctgg cctatcgtaa cttttttgcg ctgaaaggcc tgaccacgag ccgtggtgaa   120
ccggtgcagg gcgtgtatgg ctttgcgaaa agcctgctga aagcgctgaa agaggatggc   180
gacgttgtta ttgtggtgtt tgatgcgaaa gcgccgtttt ttcgtcatga agcgtacgaa   240
gcgtataaag cgggccgtgc gccgaccccg gaagattttc gcgtcagct ggccctgatt    300 aaagagctgg ttgatctgct gggcctggaa cgtctggaag tgccgggctt tgaagcggat   360
gatgtgctgg ccaccctggc caaacaggcg gaacgtgaag ctatgaagt gcgtattctg    420 accgcggatc gtgacctgtt tcagctgctg agcgatcgta ttgcggtgct gcatccggaa   480
ggccatctga ttacgccggg ctggctgtgg aacgttatg gcctgaaacc ggaacagtgg   540
gtggattttc gtgcgctggc cggcgatccg agcgataaca ttccgggcgt gaaaggcatt   600
ggcgaaaaaa ccgcgctgaa actgctgaaa gaatggggca gcctggaaaa tctgctgaaa   660
aacctggatc atgtgaaacc gccgagcgtg cgtgaaaaaa ttctggccca tctggatgat   720
ctgcgtctgt ctcaggagct gtctcgcgtt cgtaccgatc tgccgctgaa agtggatttt   780
aaaaaacgtc gtgaaccgga tcgtgaaggc ctgaaagcgt ttctggaacg cctggaattt   840
```

-continued

```
ggcagcctgc tgcatgaatt tggcctgctg gaaagcccgc tgccggcgga agaggcgccg    900
tggccgccac cggaaggtgc gtttctgggc tatcgtctga gccgtccgga accgatgtgg    960
gcggagctgc tggccctggc cgcgagcgcg aaaggtcgtg tgtatcgtgc ggaagaaccg   1020
tatgcgcgcg tgcgtggcct gaaagaagtg cgcggcctgc tggctaaaga cctggccgtg   1080
ctggccctgc gtgaaggtct ggatctgccg ccgaccgatg atccgatgct gctggcctat   1140
ctgctggacc cgagcaacac caccccggaa ggtgtggcgc gtcgttatgg cggcgaatgg   1200
accgaagaag cgggcgaacg cgcggttctg agcgaacgtc tgtatgaaaa cctgctgggc   1260
cgtctgcgtg gcgaagaaaa actgctgtgg ctgtatgaag aagtggaaaa accgctgagc   1320
cgtgtgctgg cccatatgga agcgaccggc gtgcgtctgg atgtggcgta tctgaaagcc   1380
ctgagcctgg aagtggcgga agaaatgcgt cgtctggaag aagaagtgtt tcgtctggcc   1440
ggccatccgt ttaacctgaa cagccgtgat cagctggaac gtgtgctgtt tgatgagctg   1500
ggcctgccgc cgattggcaa aaccgaaaaa accggcaaac gtagcaccag cgcggcggtt   1560
ctggaagcgc tgcgtgaagc gcatccgatt gtggaaaaaa tcctgcaata tcgtgagctg   1620
gccaaactga aggcaccta tattgatccg ctgccggccc tggtgcatcc gaaaaccggc   1680
cgtctgcata cccgttttaa ccagaccgcg accgcgaccg tcgtctgag cagcagcgat   1740
ccgaacctgc aaaacattcc ggtgcgtacc ccgctgggcc agcgtattcg tcgtgcgttt   1800
gtggccgaag aaggctatct gctggttgcg ctggattata gccagattga gctgcgtgtt   1860
ctggcccacc tgagcggcga tgaaaatctg attcaggtgt tcaggaagg ccgcgatatt   1920
catacccaga ccgcgagctg gatgtttggc ctgccggccg aagcgatcga tccgctgatg   1980
cgtcgtgcgg cgaaaaccat taactttggc gtgctgtatg gcatgagcgc gcatcgcctg   2040
agccaggagc tgagcattcc gtacgaagaa gcggtggcgt ttattgatcg ttatttccag   2100
agctacccga agtgaaagc gtggattgaa cgtaccctgg aagaaggccg tcagcgcggc   2160
tatgtggaaa ccctgtttgg ccgtcgtcgt tatgtgccgg atctgaacgc gcgtgtgaaa   2220
agcgttcgtg aagcggcgga acgtatggcg tttaacatgc cggttcaggg caccgcggcg   2280
gatctgatga aactggcaat ggtgcgtctg tttccgcgtc tgccggaagt gggtgcgcgt   2340
atgctgctgc aagtgcatga tgagctgctg ctggaagccc cgaaagaacg tgcggaagcg   2400
gcggcagccc tggccaaaga agtgatgaa ggcgtttggc cgctggccgt gccgctggaa   2460
gttgaagtgg gcattggtga agattggctg agcgccaaag gctaa               2505
```

<210> SEQ ID NO 44
<211> LENGTH: 834
<212> TYPE: PRT
<213> ORGANISM: Thermus eggertssonii

<400> SEQUENCE: 44

```
Met Gly Arg Gly Met Leu Pro Leu Phe Glu Pro Lys Gly Arg Val Leu
1               5                   10                  15

Leu Val Asp Gly His His Leu Ala Tyr Arg Asn Phe Phe Ala Leu Lys
            20                  25                  30

Gly Leu Thr Thr Ser Arg Gly Glu Pro Val Gln Gly Val Tyr Gly Phe
        35                  40                  45

Ala Lys Ser Leu Leu Lys Ala Leu Lys Glu Asp Gly Asp Val Val Ile
    50                  55                  60

Val Val Phe Asp Ala Lys Ala Pro Phe Phe Arg His Glu Ala Tyr Glu
65                  70                  75                  80

Ala Tyr Lys Ala Gly Arg Ala Pro Thr Pro Glu Asp Phe Pro Arg Gln
```

-continued

```
                    85                  90                  95
Leu Ala Leu Ile Lys Glu Leu Val Asp Leu Leu Gly Leu Glu Arg Leu
                100                 105                 110
Glu Val Pro Gly Phe Glu Ala Asp Val Leu Ala Thr Leu Ala Lys
            115                 120                 125
Gln Ala Glu Arg Glu Gly Tyr Glu Val Arg Ile Leu Thr Ala Asp Arg
        130                 135                 140
Asp Leu Phe Gln Leu Leu Ser Asp Arg Ile Ala Val Leu His Pro Glu
145                 150                 155                 160
Gly His Leu Ile Thr Pro Gly Trp Leu Trp Glu Arg Tyr Gly Leu Lys
                165                 170                 175
Pro Glu Gln Trp Val Asp Phe Arg Ala Leu Ala Gly Asp Pro Ser Asp
            180                 185                 190
Asn Ile Pro Gly Val Lys Gly Ile Gly Glu Lys Thr Ala Leu Lys Leu
        195                 200                 205
Leu Lys Glu Trp Gly Ser Leu Glu Asn Leu Leu Lys Asn Leu Asp His
        210                 215                 220
Val Lys Pro Pro Ser Val Arg Glu Lys Ile Leu Ala His Leu Asp Asp
225                 230                 235                 240
Leu Arg Leu Ser Gln Glu Leu Ser Arg Val Arg Thr Asp Leu Pro Leu
                245                 250                 255
Lys Val Asp Phe Lys Lys Arg Glu Pro Asp Arg Glu Gly Leu Lys
            260                 265                 270
Ala Phe Leu Glu Arg Leu Glu Phe Gly Ser Leu Leu His Glu Phe Gly
        275                 280                 285
Leu Leu Glu Ser Pro Leu Pro Ala Glu Ala Pro Trp Pro Pro
        290                 295                 300
Glu Gly Ala Phe Leu Gly Tyr Arg Leu Ser Arg Pro Glu Pro Met Trp
305                 310                 315                 320
Ala Glu Leu Leu Ala Leu Ala Ala Ser Ala Lys Gly Arg Val Tyr Arg
                325                 330                 335
Ala Glu Glu Pro Tyr Gly Ala Leu Arg Gly Leu Lys Glu Val Arg Gly
            340                 345                 350
Leu Leu Ala Lys Asp Leu Ala Val Leu Ala Leu Arg Glu Gly Leu Asp
        355                 360                 365
Leu Pro Pro Thr Asp Asp Pro Met Leu Leu Ala Tyr Leu Leu Asp Pro
        370                 375                 380
Ser Asn Thr Thr Pro Glu Gly Val Ala Arg Arg Tyr Gly Gly Glu Trp
385                 390                 395                 400
Thr Glu Glu Ala Gly Glu Arg Ala Val Leu Ser Glu Arg Leu Tyr Glu
                405                 410                 415
Asn Leu Leu Gly Arg Leu Arg Gly Glu Glu Lys Leu Leu Trp Leu Tyr
            420                 425                 430
Glu Glu Val Glu Lys Pro Leu Ser Arg Val Leu Ala His Met Glu Ala
        435                 440                 445
Thr Gly Val Arg Leu Asp Val Ala Tyr Leu Lys Ala Leu Ser Leu Glu
        450                 455                 460
Val Ala Glu Glu Met Arg Arg Leu Glu Glu Val Phe Arg Leu Ala
465                 470                 475                 480
Gly His Pro Phe Asn Leu Asn Ser Arg Asp Gln Leu Glu Arg Val Leu
                485                 490                 495
Phe Asp Glu Leu Gly Leu Pro Pro Ile Gly Lys Thr Glu Lys Thr Gly
            500                 505                 510
```

-continued

```
Lys Arg Ser Thr Ser Ala Ala Val Leu Glu Ala Leu Arg Glu Ala His
            515                 520                 525

Pro Ile Val Glu Lys Ile Leu Gln Tyr Arg Glu Leu Ala Lys Leu Lys
        530                 535                 540

Gly Thr Tyr Ile Asp Pro Leu Pro Ala Leu Val His Pro Lys Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Gly Tyr Leu Leu
        595                 600                 605

Val Ala Leu Asp Tyr Ser Gln Ile Glu Leu Arg Val Leu Ala His Leu
610                 615                 620

Ser Gly Asp Glu Asn Leu Ile Gln Val Phe Gln Glu Gly Arg Asp Ile
625                 630                 635                 640

His Thr Gln Thr Ala Ser Trp Met Phe Gly Leu Pro Ala Glu Ala Ile
                645                 650                 655

Asp Pro Leu Met Arg Arg Ala Ala Lys Thr Ile Asn Phe Gly Val Leu
            660                 665                 670

Tyr Gly Met Ser Ala His Arg Leu Ser Gln Glu Leu Ser Ile Pro Tyr
        675                 680                 685

Glu Glu Ala Val Ala Phe Ile Asp Arg Tyr Phe Gln Ser Tyr Pro Lys
690                 695                 700

Val Lys Ala Trp Ile Glu Arg Thr Leu Glu Glu Gly Arg Gln Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Arg Leu Phe Pro Arg Leu Pro Glu Val Gly Ala Arg Met Leu Leu Gln
770                 775                 780

Val His Asp Glu Leu Leu Leu Glu Ala Pro Lys Glu Arg Ala Glu Ala
785                 790                 795                 800

Ala Ala Ala Leu Ala Lys Glu Val Met Glu Gly Val Trp Pro Leu Ala
                805                 810                 815

Val Pro Leu Glu Val Glu Val Gly Ile Gly Glu Asp Trp Leu Ser Ala
            820                 825                 830

Lys Gly
```

— # *THERMUS EGERTSSONII* DNA POLYMERASES

CROSS-REFERENCE TO RELATED APPLICATIONS

The present application is a National Phase Application of International Application No. PCT/EP2007/060724, filed Oct. 9, 2007, which claims priority to European Patent Application No. 06021140.6 filed Oct. 9, 2006, which applications are incorporated herein fully by this reference.

FIELD OF THE INVENTION

The present invention relates to thermostable DNA polymerases derived from *Thermus eggertssonii*, means for producing and isolating the same, and uses thereof.

BACKGROUND

Thermophilic bacteria (referred to herein as "thermophiles") are capable of growth at elevated temperatures. Unlike mesophiles, which grow best at temperatures in the range of 25-40° C., or psychrophilic bacteria, which grow best from 15-20° C., thermophiles grow best at temperatures greater than 50° C. Indeed, some thermophiles grow best at 65-75° C., while hyperthermophiles grow best at temperatures up to 130° C. (Black, Microbiology Principles and Applications, 2d edition, Prentice Hall, New Jersey, 145-146, 1991, herein incorporated by reference).

Thermophiles may be aerobic or anaerobic, and are found in a wide variety of genera and species, including the phototrophic bacteria (e.g., the purple bacteria, green bacteria, and cyanobacteria), eubacteria (e.g., *Baccillus, Clostridium, Thiobacillus, Desulfotomaculum, Thermus*, lactic acid bacteria, *actinomycetes, spirochetes*, and numerous other genera), and the archaebacteria (e.g., *Pyrococcus, Thermococcus, Thermoplasma, Thermotoga, Sulfolobus*, and the methanogens). Accordingly, the environments in which thermophiles are normally found vary greatly, although all of these areas are associated with high temperatures.

Thermophiles, like other bacteria, contain five types of DNA polymerases, termed polymerase I, II, III, IV, and V. Given the nature of thermophile habitats, these enzymes typically exhibit thermostability, and are generally referred to as thermostable DNA polymerases. DNA polymerase I ("Pol I") is the most abundant polymerase and is generally responsible for certain types of DNA repair, including a repair-like reaction that permits the joining of Okazaki fragments during DNA replication. Pol I is essential for the repair of DNA damage induced by UV irradiation and radiomimetic drugs. DNA polymerase II is thought to play a role in repairing DNA damage that induces the SOS response. In mutants that lack both Pol I and DNA polymerase III, DNA polymerase II repairs UV-induced lesions. DNA polymerase III is a multi-subunit replicase.

Thermostable DNA polymerases have proven very useful in a number of applications in molecular biology. One such application is the polymerase chain reaction (PCR). The PCR process is described, for example, in U.S. Pat. Nos. 4,683,195 and 4,683,202, the disclosures of which are incorporated herein by reference. In a PCR reaction, primers, template, and nucleoside triphosphates are combined in appropriate buffer with a DNA polymerase, for the basic steps of thermal denaturation of target DNA, hybridization of primers to template with cooling of the reaction mixture, and primer extension to produce extension products complementary to template sequences. Thermal denaturation is repeated, primers are annealed to extension products with cooling of the reaction mixture, and previously produced extension products serve as templates for subsequent primer extension reactions. This cycle is repeated a number of times, resulting in an exponential amplification of the desired nucleic acid sequence. Use of a thermostable DNA polymerase provides for repeated heating/cooling cycles without loss of enzyme activity.

A number of applications, for example long range PCR, are hindered by the error rates of Pol I proteins currently available (e.g., Taq DNA Pol I). In addition to decreased error rates, a number of applications would benefit from the use of DNA Pol I exhibiting improved sequence discrimination activity, primer mismatch tolerance, and increased thermostability. For example, a DNA Pol I that tolerates primer mismatches would be useful in PCR methods involving the use of degenerative primers.

SUMMARY OF INVENTION

The present invention stems in part from the isolation and characterization of a novel DNA Pol I from the eubacteria *T. eggertssonii* (Teg). As disclosed herein, the Teg DNA Pol I has significantly superior characteristics as compared to DNA Pol I proteins in the prior art.

In one aspect, the invention provides Teg DNA Pol I proteins, including functional Teg DNA Pol I fragments, and variants of Teg DNA Pol I. The Teg DNA Pol I proteins provided also include Pol L fusion proteins and Pol I chimeric proteins. Amino acid sequences of full-length Teg DNA Pol I from various strains of *T. eggertssonii* are exemplified. A codon optimized *T. eggertssonii* is provided.

In one embodiment, the invention provides a Teg DNA Pol I comprising an amino acid sequence having greater than 95%, more preferably at least about 96%, more preferably at least about 97%, more preferably at least about 98% identity to an amino acid sequence selected from the group consisting of SEQ ID NO: 6, 17, 18, 19, 20, 21, 22 and 23.

A codon optimized *T. eggertssonii* is provided (amino acid sequence SEQ ID NO. 44).

In a preferred embodiment the invention provides a Teg DNA Pol I comprising an amino acid sequence having grater than 95%, more preferably at least about 96%, more preferably at least about 97%, more preferably at least about 98% identity to the amino acid sequence of SEQ ID NO. 6. Also chimeras of the codon optimized *T. eggertssonii* are provided (amino acid sequence SEQ ID NO. 44).

In one embodiment, the invention provides a Teg DNA Pol I comprising an amino acid sequence selected from the group consisting of SEQ ID NO: 6, 17, 18, 19, 20, 21, 22 and 23. In one embodiment the codon optimized version is preferred (SEQ ID NO. 44).

In one embodiment the invention provides a Teg DNA Pol I comprising an amino acid sequence according to SEQ ID NO. 6. A codon optimized *T. eggertssonii* is provided (amino acid sequence SEQ ID NO. 44).

Teg DNA Pol I proteins of the invention have a number of highly desirable characteristics. For example, in one embodiment, the invention provides a Teg DNA Pol I having 5'-3' exonuclease activity. In one embodiment, the invention provides a Teg DNA Pol I having higher fidelity than Taq DNA Pol I. In one embodiment, the invention provides a Teg DNA Pol I that is capable of more efficiently extending mismatched primers than Taq DNA Pol I.

In a preferred embodiment, the Teg DNA Pol I comprises a 5'-3'-exonuclease domain, an internal 3'-5'-exonuclease domain (structural domain without inherent nuclease activity) and a polymerase domain. In one embodiment, the polymerase domain of Teg DNA Pol I further comprises a palm subdomain which comprises an amino acid sequence having at least about 80%, more preferably at least about 85%, more preferably at least about 90%, more preferably at least about 95%, more preferably at least about 98% identity to the amino acid sequence set forth by residues 434-448, 556-615, 751-830 of SEQ ID NO: 6.

In a preferred embodiment, the polymerase domain of Teg DNA Pol I further comprises a palm subdomain which comprises an amino acid sequence having at least about 80%, more preferably at least about 85%; more preferably at least about 90%, more preferably at least about 95%, more preferably at least about 98% identity to the amino acid sequence set forth by residues 438-452, 560-619, 755-834 of SEQ ID NO: 44.

In an especially preferred embodiment, the palm subdomain comprises the amino acid sequence set forth by residues 434-448, 556-615, 751-830 of SEQ ID NO: 6.

In a particularly preferred embodiment, the palm subdomain comprises the amino acid sequence set forth by residues 438-452, 560-619, 755-834 of SEQ ID NO: 44.

In one embodiment, the polymerase domain of Teg DNA Pol I comprises a thumb subdomain which comprises an amino acid sequence having at least about 80%, more preferably at least about 85%, more preferably at least about 90%, more preferably at least about 95%, more preferably at least about 98% identity to the amino acid sequence set forth by residues 449-555 of SEQ ID NO: 6.

In a preferred embodiment, the polymerase domain of Teg DNA Pol I comprises a thumb subdomain which comprises an amino acid sequence having at least about 80%, more preferably at least about 85%, more preferably at least about 90%, more preferably at least about 95%, more preferably at least about 98% identity to the amino acid sequence set forth by residues 453-559 of SEQ ID NO: 44.

In an especially preferred embodiment, the thumb subdomain comprises the amino acid sequence set forth by residues 449-555 of SEQ ID NO: 6.

In an especially preferred embodiment, the thumb subdomain comprises the amino acid sequence set forth by residues 453-559 of SEQ ID NO: 44.

In one embodiment, the polymerase domain of Teg DNA Pol I comprises a finger subdomain which comprises an amino acid sequence having at least about 80%, more preferably at least about 85%, more preferably at least about 90%, more preferably at least about 95%, more preferably at least about 98% identity to the amino acid sequence set forth by residues 616-750 of SEQ ID NO: 6.

In one embodiment, the polymerase domain of Teg DNA Pol I comprises a finger subdomain which comprises an amino acid sequence having at least about 80%, more preferably at least about 85%, more preferably at least about 90%, more preferably at least about 95%, more preferably at least about 98% identity to the amino acid sequence set forth by residues 620-754 of SEQ ID NO: 44.

In an especially preferred embodiment, the finger subdomain comprises the amino acid sequence set forth by residues 616-750 of SEQ ID NO: 6.

In an especially preferred embodiment, the finger subdomain comprises the amino acid sequence set forth by residues 620-754 of SEQ ID NO: 44.

Teg DNA Pol I proteins of the invention also include functional fragments of full length Teg DNA Pol I proteins. In one embodiment, the invention provides a Teg DNA Pol I comprising a functional fragment of a full length Teg DNA Pol I. In one embodiment, die Teg DNA Pol I consists essentially of a functional fragment of a full length Teg DNA Pol I. In a preferred embodiment, the Teg DNA Pol I comprises a fragment of an amino acid sequence selected from the group consisting of SEQ ID NO: 6 and preferably SEQ ID NO. 44.

In a preferred embodiment, the Teg DNA Pol I comprises a 5'-3' exonuclease domain of the amino acid sequence set forth by residues 1-288 of SEQ ID NO: 6, a 3'-5' exonuclease domain of the amino acid sequence set forth by residues 296-433 of SEQ ID NO: 6 and a polymerase domain of the amino acid sequence set forth by residues 289-830 of SEQ ID NO: 6. In one embodiment, the Teg DNA Pol I consists essentially of a 5'-3' exonuclease, a 3'-5' exonuclease domain and a polymerase domain.

In a preferred embodiment, the Teg DNA Pol I comprises a 5'-3' exonuclease domain of the amino acid sequence set forth by residues 5-292 of SEQ ID NO: 44, a 3'-5' exonuclease domain of the amino acid sequence set forth by residues 300-437 of SEQ ID NO: 44 and a polymerase domain of the amino acid sequence set forth by residues 293-834 of SEQ ID NO: 44. In one embodiment, the Teg DNA Pol I consists essentially of a 5'-3' exonuclease, a 3'-5' exonuclease domain and a polymerase domain.

In one embodiment, the polymerase domain of Teg DNA Pol I comprises a palm subdomain. In a preferred embodiment, the palm subdomain comprises an amino acid sequence having at least about 80%, more preferably at least about 85%, more preferably at least about 90%, more preferably at least about 95%, more preferably at least about 98% identity to the amino acid sequence set forth by residues 434-448, 556-615 and 751-830 of SEQ ID NO: 6. In an especially preferred embodiment, the palm subdomain comprises the amino acid sequence set forth by residues 434-448, 556-615 and 751-830 of SEQ ID NO: 6.

In one embodiment, the polymerase domain of Teg DNA Pol I comprises a palm subdomain. In a preferred embodiment, the palm subdomain comprises an amino acid sequence having at least about 80%, more preferably at least about 85%, more preferably at least about 90%, more preferably at least about 95%, more preferably at least about 98% identity to the amino acid sequence set forth by residues 438-452, 560-619 and 755-834 of SEQ ID NO: 44. In an especially preferred embodiment, the palm subdomain comprises the amino acid sequence set forth by residues 438-452, 560-619 and 755-834 of SEQ ID NO: 44.

In one embodiment, the polymerase domain of Teg DNA Pol I comprises a thumb subdomain. In a preferred embodiment, the thumb region comprises an amino acid sequence having at least about 80%, more preferably at least about 85%, more preferably at least about 90%, more preferably at least about 95%, more preferably at least about 98% identity to the amino acid sequence set forth by residues 449-650 of SEQ ID NO: 6. In an especially preferred embodiment, the thumb subdomain comprises the amino acid sequence set forth by residues 449-650 of SEQ ID NO: 6.

In one embodiment, the polymerase domain of Teg DNA Pol I comprises a thumb subdomain. In a preferred embodiment, the thumb region comprises an amino acid sequence having at least about 80%, more preferably at least about 85%, more preferably at least about 90%, more preferably at least about 95%, more preferably at least about 98% identity to the amino acid sequence set forth by residues 453-654 of SEQ ID NO: 44. In an especially preferred embodiment, the thumb subdomain comprises the amino acid sequence set forth by residues 453-654 of SEQ ID NO: 44.

In one embodiment, the polymerase domain of Teg DNA Pol I comprises a finger subdomain. In a preferred embodiment, the finger subdomain comprises an amino acid sequence having at least about 80%, more preferably at least about 85%, more preferably at least about 90%, more preferably at least about 95%, more preferably at least about 98% identity to the amino acid sequence set forth by residues 616-750 of SEQ ID NO:6. In an especially preferred embodiment, the finger subdomain comprises the amino acid sequence set forth by residues 616-750 of SEQ ID NO: 6.

In one embodiment, the polymerase domain of Teg DNA Pol I comprises a finger subdomain. In a preferred embodiment, the finger subdomain comprises an amino acid sequence having at least about 80%, more preferably at least about 85%, more preferably at least about 90%, more preferably at least about 95%, more preferably at least about 98% identity to the amino acid sequence set forth by residues 620-754 of SEQ ID NO: 44. In all especially preferred embodiment, the finger subdomain comprises the amino acid sequence set forth by residues 620-754 of SEQ ID NO: 44

In one embodiment, the Teg DNA Pol I is a truncated DNA Pol I essentially lacking the N-terminal 5'-3'-exonulease domain comprising the amino acid sequence set forth by residues 1-288 of SEQ ID NO:6, wherein the DNA Pol I lacks 5'-3' exonuclease activity. The truncated variant Teg DNA Pol I lacking exonuclease activity comprises essentially the amino acid sequence set forth by the residues 289 to 830 of SEQ ID NO: 6.

In one embodiment, the Teg DNA Pol I is a truncated DNA Pol I essentially lacking the N-terminal 5'-3'-exonuclease domain comprising the amino acid sequence set forth by residues 5-292 of SEQ ID NO: 44, wherein the DNA Pol I lacks 5'-3' exonuclease activity. The truncated variant Teg DNA Pol I lacking exonuclease activity comprises essentially the amino acid sequence set forth by the residues 293 to 834 of SEQ ID NO: 44.

In one embodiment, the variant Teg DNA polymerase I comprises an amino acid sequence having a substitution at position 679 of SEQ ID NO: 6 replacing the glutamic acid residue by a positively charged amino acid such as lysine or arginine. Analysis of the three dimensional structure of Taq DNA polymerase I bound to a DNA substrate has shown that the negative charge of the glutamic acid at the corresponding position (681) in the Taq DNA polymerase sequence (SEQ ID NO:2) contacts the negatively-charged phosphate backbone of the priming strand in the DNA substrate. That contact creates an electrostatic repulsion effect limiting the extension rate and processivity of the polymerase. Mutant variants carrying a lysine instead of glutamic acid at the position have shown faster extension rates and better processivity. Variant Teg DNA polymerases with those features are desirable for various applications, such as fast PCR, DNA sequencing, amplification of long target sequences.

In one embodiment, the variant Teg DNA polymerase I comprises an amino acid sequence having a substitution at position 683 of SEQ ID NO: 44 replacing the glutamic acid residue by a positively charged amino acid such as lysine or arginine. Analysis of the three dimensional structure of Taq DNA polymerase I bound to a DNA substrate has shown that the negative charge of the glutamic acid at the corresponding position (681) in the Taq DNA polymerase sequence (SEQ ID NO:2) contacts the negatively-charged phosphate backbone of the priming strand in the DNA substrate. That contact creates an electrostatic repulsion effect limiting the extension rate and processivity of the polymerase. Mutant variants carrying a lysine instead of glutamic acid at the position have shown faster extension rates and better processivity. Variant Teg DNA polymerases with those features are desirable for various applications, such as fast PCR, DNA sequencing, amplification of long target sequences.

Teg DNA Pol I proteins of the invention also include variants of Teg DNA Pol I proteins which have desirable properties. Included among Pol I variants are functional fragments of full length Pol I variants.

In one embodiment, a variant Teg DNA polymerase I comprises an amino acid sequence having single or combined substitutions at the positions 612-613 of SEQ ID NO:6. In one embodiment, a variant Teg DNA polymerase I comprises an amino acid sequence having single or combined substitutions at the positions 616-617 of SEQ ID NO:44. Random mutagenis experiments performed on Taq and E. coli DNA polymerase I have shown that the amino acid residues at the corresponding positions in their sequences control discrimination between rNTPs and dNTPs as polymerization substrate. They also control discrimination between RNA- or DNA-primed DNA templates, templates with base mismatches at the 3'-terminus of the primer and perfectly annealed primers and between labeled and non-labelled dNTP substrates. Based on the nature of the substitution(s) at these positions, a number of variant Teg DNA Pol I can be provided with useful features for different applications. Variants with increased discrimination against the extension of mismatched primers are useful for allel-specific PCR. Variants with increased affinity for labeled ddNTP substrates are useful for fluorescent DNA sequencing and real-time PCR.

In one embodiment, the invention provides a variant Teg DNA Pol I having reduced 5'-3' exonuclease activity. In a preferred embodiment, the glycine residue of the Teg Pol I variant corresponding to position 43 of SEQ ID NO: 6 is mutated to either aspartate or glutamate. In a further preferred embodiment, the glycine residue of the Teg Pol I variant corresponding to position 47 of SEQ ID NO: 44 is mutated to either aspartate or glutamate.

In one embodiment, the invention provides a variant Teg DNA Pol I having substituted the C-terminal glycine residue at position 830 of SEQ ID NO: 6 by a glutamic acid residue. In a preferred embodiment, the invention provides a variant Teg DNA Pol I having substituted the C-terminal glycine residue at position 834 of SEQ ID NO: 44 by a glutamic acid residue. Three dimensional structure of other *Thermus* DNA polymerases I having a C-terminal glutamic acid residue show that the beta carboxylic group of that residue is involved in stabilizing and coordinating a critical magnesium ion in the polymerase active site. Providing that additional carboxylic group reduces the effective magnesium concentration at which the variant Teg DNA polymerase I can carry out processive DNA synthesis. The ability to work at lower magnesium concentration is critical in polymerase chain reactions (PCR), because elevated magnesium concentrations have a negative impact on the specificity of DNA amplification PCR.

In another embodiment of the invention, the variant of Teg DNA Pol I is based on the knowledge that a single residue in DNA polymerases of *Thermus aquaticus* DNA polymerase I family is critical for distinguishing between deoxy- and dideoxyribonucleotides (Taber, S., Richardson, C. C., Proc. Natl. Acad. Sci. USA, 1995, Jul. 3, 92 (14): 6339-43, A single residue and DNA polymerase of the *Escherichia coli* DNA polymerase I family is critical for distinguishing between deoxy- and dideoxyriboncleotides) In a preferred embodiment, the Pol I variant comprises an amino acid sequence having a substitution residue in place of a wildtype phenylalanine in a position corresponding to position 665 of SEQ ID NO: 6. In a preferred embodiment, the substitution residue is a tyrosine. In a preferred embodiment, the Pol I variant comprises an amino acid sequence having a substitution residue in place of a wildtype phenylalanine in a position corresponding to position 669 of SEQ ID NO: 44. In a preferred embodiment, the substitution residue is a tyrosine.

In one embodiment, the variant Teg DNA Pol I has 4 additional amino acid residues Met, Pro, Arg/Lys and Gly at the N-terminus of the amino acid sequence set forth in SEQ ID NO: 6. In one embodiment, the variant Teg DNA Pol I has 4 additional amino acid residues Met, Pro, Arg/Lys and Gly at the N-terminus of the amino acid sequence set forth in SEQ ID NO: 44. Based on the deciphered three dimensional structure of Taq DNA polymerase bound to DNA substrate these three additional N-terminal residues are a part of the DNA-binding site in the N-terminal nuclease domain. In the absence of the additional N-terminal amino acids the Teg DNA polymerase has a weakened binding affinity and strength towards its DNA substrate. Teg DNA Pol I variants with strengthened DNA substrate binding properties have better processivity and a faster extension rate than Teg DNA Pol I with the wild type sequence set forth in SEQ ID NO: 6. Improved processivity and faster extension rates are important functional features of thermostable DNA polymerases used to perform the polymerase chain reaction (PCR) application. They allow for amplification of longer target sequences with higher sensitivity requiring less DNA template in the sample. The additional proline residue in position 2 of the variant Teg DNA Pol I in this embodiment stabilizes the recombinant polymerase against N-terminal degradation by endogenous cytoplasmic proteinases of the *E. coli* host cells according to die rules of stabilizing N-terminal amino acid residues in *E. coli* well established in the prior art.

Teg DNA Pol I proteins of the invention also include DNA Pol I fusion proteins that comprise a Teg DNA Pol I protein fused to a non-Teg DNA Pol I protein moiety. In one embodiment, a DNA Pol I fusion protein comprises an exonuclease domain of a Teg DNA Pol I protein of the invention. In one embodiment, a DNA Pol I fusion protein comprises a polymerase domain of a Teg DNA Pol I protein of the invention. DNA Pol I fusion proteins of the invention may include moieties that, for example, provide for purification, or contribute to the altered thermostability or altered catalytic activity of a DNA Pol I fusion protein as compared to a Teg DNA Pol I protein.

Teg DNA Pol I proteins of the invention also include DNA Pol I chimeric proteins that comprise a Teg DNA Pol I protein fused to one or more domains of another polymerase.

In one aspect the invention provides Teg DNA Pol I nucleic acids encoding Teg DNA Pol I proteins of the invention. The Teg DNA Pol I nucleic acids include nucleic acids encoding DNA Pol I fusion proteins and DNA Pol I chimeric proteins of the invention. In a preferred embodiment, the present invention provides Teg DNA Pol I nucleic acids encoding Pol I proteins, which comprise a nucleotide sequence having at least about 95%, more preferably at least about 96%, more preferably at least about 97%, more preferably at least about 98%, most preferably at least about 99% identity to a nucleotide sequence selected from the group consisting of SEQ ID NO: 5. In a preferred embodiment, the present invention provides Teg DNA Pol I nucleic acids encoding Pol I proteins, which comprise a nucleotide sequence having at least about 95%, more preferably at least about 96%, more preferably at least about 97%, more preferably at least about 98%, most preferably at least about 99% identity to a nucleotide sequence selected from the group consisting of SEQ ID NO: 43.

In an especially preferred embodiment, the invention provides Teg DNA Pol I nucleic acids encoding Teg DNA Pol I proteins, which comprise a nucleotide sequence selected from the group consisting of SEQ ID NO: 5. In an especially preferred embodiment, the invention provides Teg DNA Pol I nucleic acids encoding Teg DNA Pol I proteins, which comprise a nucleotide sequence selected from the group consisting of SEQ ID NO: 43.

Also provided herein are vectors for the replication and expression of Teg DNA Pol I nucleic acids. In one embodiment, the invention provides Teg DNA Pol I expression vectors for the expression of Teg DNA Pol I proteins in cells.

Also provided herein are methods for transforming host cells with vectors of the invention, as well as host cells so transformed. Host cells include procaryotic and eucaryotic cells. In a preferred embodiment, the host cell is an *E. coli* host cell.

In one aspect, the invention provides methods for producing and/or isolating a Teg DNA Pol I of the invention. In one embodiment, methods comprise purifying a naturally occurring Teg DNA Pol I from the *eubacterium T. eggertssonii*. In another embodiment, the methods comprise producing a Teg DNA Pol I by recombinant means and isolating the Pol I. In a preferred embodiment, the methods comprise transforming bacteria with a Teg DNA Pol I expression vector and isolating Pol I protein from transformed bacteria.

In one aspect, the invention provides compositions and methods for nucleic acid amplification. The compositions comprise one or more Teg Pol I proteins of the invention. The methods comprise subjecting a DNA molecule to an amplification reaction in all amplification reaction mixture comprising a Teg Pol I protein of the invention.

In a preferred embodiment, the nucleic acid molecule used in the amplification method is DNA. In a preferred embodiment, the DNA molecule is double stranded. In other embodiments, the DNA molecule is single stranded. In a preferred embodiment, the double stranded DNA molecule is a linear DNA molecule. In other embodiments, the DNA molecule is non-linear, for example circular or supercoiled DNA.

In a preferred embodiment, the amplification method is a thermocycling amplification method useful for amplifying a nucleic acid molecule, preferably DNA, which is preferably double stranded, by a temperature-cycled mode. In a preferred embodiment, the method involves subjecting the nucleic acid molecule to a thermocycling amplification reaction in a thermocycling amplification reaction mixture. The thermocycling amplification reaction mixture comprises a Teg DNA Pol I protein of the invention.

In a preferred embodiment, the amplification method is a PCR method. In one embodiment, the method is a degenerate PCR method. In one embodiment, the method is a real-time PCR method.

In one embodiment, the invention provides reaction mixtures for nucleic acid amplification, which mixtures comprise a Teg DNA Pol I protein of the invention. Preferred reaction mixtures of the invention are useful for DNA amplification. In a preferred embodiment, the reaction mixture is a thermocycling reaction mixture useful for thermocycling amplification reactions. Amplification reaction mixtures may include additional reagents, such as, but not limited to, dNTPs, primers, buffer, and/or stabilizers.

In one embodiment, the invention provides reaction mixtures for amplifying nucleic acids using degenerate primers in PCR, which are useful for the amplification of homologous sequence targets containing nucleotide polymorphisms. The reaction mixtures comprise a Teg DNA Pol I protein of the invention. Reaction mixtures for PCR with degenerate primers may include additional reagents such as, but not limited to, dNTPs, degenerate primers, buffer, and/or stabilizers.

In a preferred embodiment, the reaction mixture comprises a Teg DNA Pol I protein of the invention, wherein the Teg DNA Pol I is present in the reaction mixture at a concentration of not less than 120 pg/µL, more preferably not less than 140 pg/µL, more preferably not less than 160 pg/µL, more preferably not less than 180 pg/µL, more preferably not less than 200 pg/µL, more preferably not less than 400 pg/µL, more preferably not less than 600 pg/µL.

In a preferred embodiment, the reaction mixture comprises a zwitterionic buffer. In a preferred embodiment, the zwitterionic buffer has a pH between about pH 7.5-8.9. In a preferred embodiment, the buffer comprises a combination of an organic zwitterionic acid and an organic zwitterionic base, potassium ions, and magnesium ions.

In an especially preferred embodiment, the reaction mixture comprises 30 mM Bicine, 59 mM Tris, 50 mM KCl, 2 mM magnesium acetate.

In one embodiment, the invention provides reaction mixtures for amplifying nucleic acids, which are useful in PCR reactions with real time product detection. The real-time reaction mixtures comprise a Teg DNA Pol I of the invention. The real-time PCR reaction mixtures may include other reagents, including, but not limited to, dNTPs, fluorescent probes, primers, buffer, stabilizers, nucleic acid-binding dye(s) and/or passive reference dye(s).

In a preferred embodiment, the reaction mixture comprises a Teg DNA Pol I, wherein the thermostable Teg Polymerase I is present in the reaction mixture at a concentration of not less than 120 pg/µL, more preferably not less than 140 pg/µL, more preferably not less than 160 pg/µL, more preferably not less than 180 pg/µL, more preferably not less than 200 pg/µL, more preferably not less than 400 pg/µL, more preferably not less than 600 pg/µL.

In a preferred embodiment, the reaction mixture comprises a zwitterionic buffer. In a preferred embodiment, the zwitterionic buffer has a pH between about pH 7.5-8.9. In a preferred embodiment, the buffer comprises a combination of an organic zwitterionic acid and a organic zwitterionic base, potassium ions, and magnesium ions.

In an especially preferred embodiment, the reaction mixture comprises a buffer comprising 40 mM Bicine, 90 mM Tris, 40 mM KCl, 4 mM magnesium acetate, and 100 mM sorbitol.

In another preferred embodiment, the reaction mixture comprises a buffer comprising 25 in M Taps, 0.05 mg/mL Anti-freeze Protein I, 10.3 mM Tris, 50 mM KCl, 5 mM magnesium acetate, 100 mM sorbitol, and 0.2 mg/mL BSA.

In one aspect, the invention provides nucleic acid amplification reaction tubes, which comprise a Teg DNA Pol I in a nucleic acid amplification reaction mixture disclosed herein.

In a preferred embodiment, the amplification reaction tubes are thermocycling amplification reaction tubes, which comprise a Teg DNA Pol I in a thermocycling amplification reaction mixture disclosed herein.

In a preferred embodiment, the thermocycling amplification reaction tubes are PCR reaction tubes, which comprise a Teg DNA polymerase I in a PCR reaction mixture disclosed herein.

In a preferred embodiment, the PCR reaction tubes are degenerative PCR reaction tubes, which comprise a Teg DNA Pol I in a degenerative PCR reaction mixture disclosed herein.

In another preferred embodiment, the PCR reaction tubes are real-time PCR reaction tubes, which comprise a Teg DNA Pol I in a real-time PCR reaction mixture disclosed herein.

In one aspect, the invention provides a nucleic acid amplification kit useful for amplifying nucleic acid, preferably DNA, which is preferably double stranded, which kit comprises a Teg DNA Pol I disclosed herein. In a preferred embodiment, the amplification kit comprises an amplification reaction mixture disclosed herein.

In a preferred embodiment, the amplification kit is a thermocycling amplification kit useful for amplifying nucleic acids, preferably DNA, which is preferably double stranded, by a temperature-cycled mode. The thermocycling amplification kit comprises a Teg DNA Pol I disclosed herein. Preferably, the thermocycling amplification kit comprises a thermocycling amplification reaction mixture disclosed herein.

In a preferred embodiment, the thermocycling amplify cation kit is a PCR kit for amplifying nucleic acids, preferably DNA, which is preferably double-stranded, by PCR. The PCR kit comprises a Teg DNA Pol I disclosed herein. Preferably the PCR kit comprises a PCR reaction mixture disclosed herein.

In a preferred embodiment, the PCR kit is a degenerative PCR kit, preferably comprising a degenerative PCR reaction mixture disclosed herein.

In another preferred embodiment, the PCR kit is a real-time PCR kit, preferably comprising a real-time PCR reaction mixture disclosed herein.

In a preferred embodiment, a nucleic acid amplification kit provided herein comprises a nucleic acid amplification reaction mixture, which amplification reaction mixture comprises an amount of a Teg DNA Pol I such that the reaction mixture can be combined with template DNA, primer(s) and/or probe(s) hybridizable thereto, and optionally appropriately diluted to produce a charged reaction mixture, wherein the thermostable DNA Pol I is capable of amplifying the DNA template by extending the hybridized primer(s).

BRIEF DESCRIPTION OF THE DRAWINGS

FIG. 1 provides enzyme allele frequencies for different loci within all genetic *Thermus lineages* (species) isolated from the environmental samples.

FIG. 2 provides the genetic diversity within *Thermus* genetic lineages (species).

FIG. 4a provides the percentage of positive phenotypic tests for the strains of all *Thermus* specific lineages (species) found. The association of the isolated *Thermus* strains with distinct genetic lineages (species) was done based on the results of the MLEE analysis using the enzyme allele frequencies of *Thermus* specific reference strains as markers.

FIG. 4b provides the percentage of more positive phenotypic tests strains of all *Thermus* specific lineages (species) found.

FIG. 5 provides the ratio of thiosulfate oxidation within various *Thermus* genetic lineages (species).

FIG. 6 provides the NCBI database accession numbers for reference sequences used for alignments discussed in this invention.

FIGS. 7a and 7b provides a nucleic acid sequence alignment comparison for the 16S rRNA genes of *T. aquaticus* (Taq), *T. brockianus* (Thr), *T. flavis* (Tfl), *T. filiformis* (Tfi), *T. thermophilus* (Tth), *T. antiranikainus, T. igniterrae, T. oshimai, T. scotoductus*, and 4 strains of *T. eggertssonii* (Teg).

FIG. 8 represents a phylogenetic dendrogram based on 16S rRNA gene fragment alignments shown in FIG. 7.

FIG. 9 provides an amino acid sequence alignment comparison for a conserved region between the active site motifs A and C of type-I DNA polymerase (PolA) of *T. aquaticus* (Taq), *T. flavus* (Tfl), *T. filiformis* (Tfi), *T. thermophilus* (Tth), and seven strains of *T. eggertssonii* (Teg).

FIGS. 11a and 11b provide an amino acid sequence alignment comparison of Type-I DNA polymerase from *T. aquaticus* (Taq), *T. brockianus* (Tbr), *T. flavus* (Tfl), *T. filiformis* (Tfi), *T. thermophilus* (Tth), and *T. eggertssonii* (Teg).

FIG. 25 provides real-time PCR amplification comparison between Teg, Taq, and Thr.

FIG. 30 provides a table with sequences disclosed herein.

DETAILED DESCRIPTION

Figure 3:
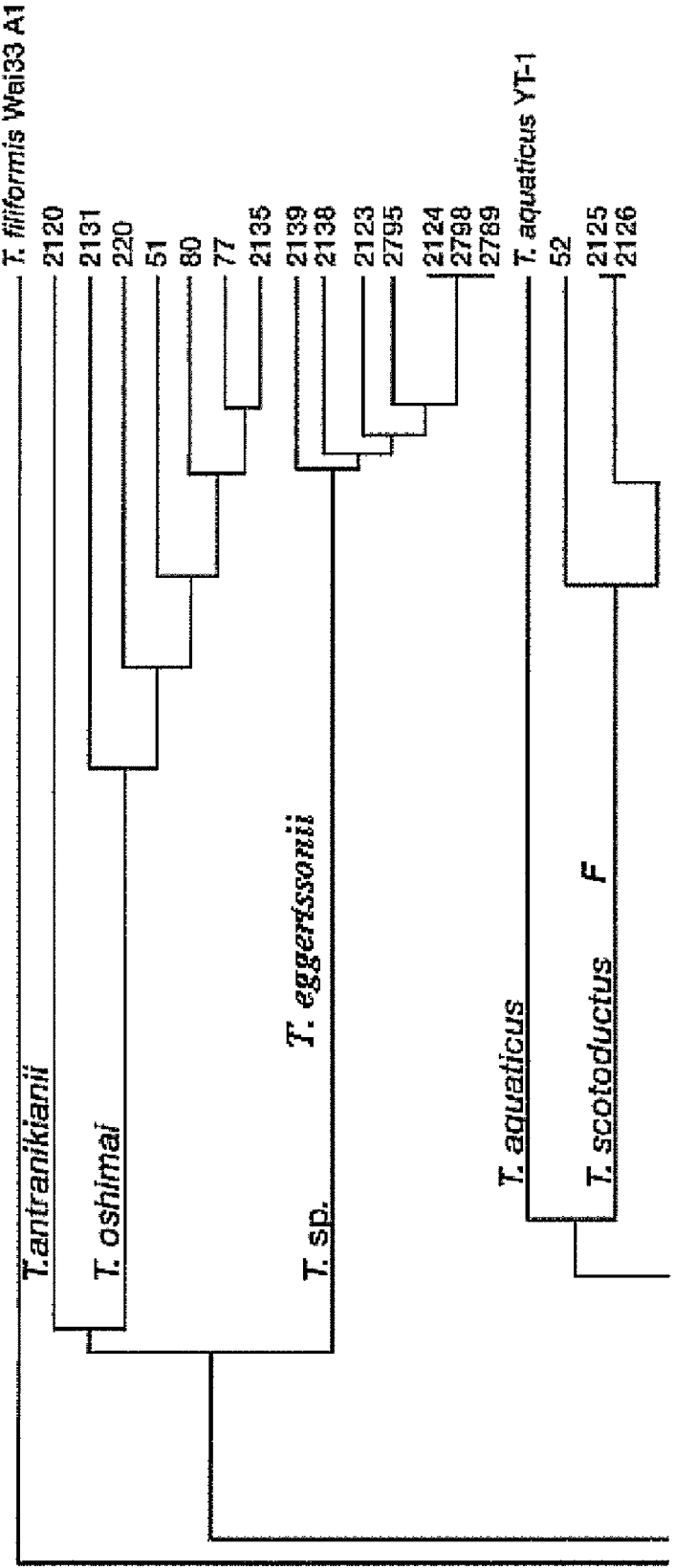
FIG. 3 provides a phylogenetic tree (MLEE analysis).

Teg DNA Pol I Nucleic Acids and Teg DNA Pol I Proteins

In one aspect, the invention provides Teg DNA Pol I proteins. The Teg DNA polymerases of the present invention provide suitable and in some cases superior enzymes for use in the PCR. As demonstrated herein, Teg DNA polymerase offers significant advantages over other commonly-used DNA polymerase I enzymes including, faster extension rate, and higher fidelity. Higher fidelity enzymes are essential for amplifying correct products and avoiding introduction of mutations, which can result in misdiagnosis and/or expression errors. In addition, faster extension rates are critical to reduce the time required for PCR thermal protocols, thus increasing laboratory efficiency and reducing overhead costs.

The invention relates to an isolated and purified thermophilic polymerase, wherein the DNA polymerase has an in-vitro primer extension rate that is >35 bases/second and at least 5 bases/second faster relative to the primer extension rate of a DNA polymerase comprising amino acid sequences SEQ ID NO: 2 or 4, when measured under identical conditions in a DNA replication assay using primed single strand M13mp18 DNA and an incubation temperature of 60° C.

In a further preferred embodiment the invention relates to DNA polymerase, wherein the polymerase has a lower frequency of dim mis-incorporation versus incorporation of the correct dCTP in a position opposite a G on a DNA template strand relative to the frequency of dTTP mis-incorporation of a DNA polymerase comprising amino acid sequence SEQ ID NO: 2 under conditions wherein a) the DNA template is present at a 10 fold excess, over the polymerase to be measured b) the reaction is performed under isothermal conditions (at 60° C.), c) the buffer contains 30 mM Bicine, 59 mM Tris, 50 mM Kcl and 2 mM magnesium acetate and d) the pH is 8.7.

In a further preferred embodiment the DNA polymerase of the invention has a lower frequency of dGTP mis-incorporation versus incorporation of the correct dCTP in a position opposite a G on the DNA template strand relative to the frequency of dGTP mis-incorporation of a DNA polymerase comprising amino acid sequence SEQ ID NO: 2 under conditions wherein a) the enzyme to be measured is present at a 10 fold excess, b) the reaction is performed under isothermal conditions, c) the buffer contains 30 mM Bicine, 59 mM Tris, 50 mM KCl and 2 mM magnesium acetate and d) the pH is 8.7.

In one embodiment the DNA polymerase has at least one intrinsic exonuclease activity, wherein the DNA polymerase has an intrinsic 5'-3' exonuclease activity.

In a further embodiment the DNA polymerase has an increased efficiency for extending primers with a mismatched T base opposite a G base in the template strand relative to a DNA polymerase comprising the amino acid sequence SEQ ID NO: 2.

In a preferred embodiment the DNA polymerase comprises an amino acid sequence selected from the group consisting of SEQ ID NO: 6, 17, 18, 19, 20, 21, 22 and 23. In a preferred embodiment the DNA polymerase comprises an amino acid sequence selected from the group consisting of SEQ ID NO: 44.

The invention also relates to a nucleic acid sequence encoding the amino acid sequence of the purified DNA polymerase according to the invention as well as a chimeric polymerase, wherein the chimeric polymerase comprises the complete or partial amino acid sequence of SEQ ID NO: 6. The invention preferably relates to a nucleic acid sequence encoding the amino acid sequence of the purified DNA polymerase according to the invention as well as a chimeric polymerase, wherein the chimeric polymerase comprises the complete or partial amino acid sequence of SEQ ID NO: 44.

In a preferred embodiment the invention relates to a nucleic acid sequence encoding the amino acid sequence of the purified chimeric polymerase according to SEQ ID NO. 6. In a preferred embodiment the invention relates to a nucleic acid sequence encoding the amino acid sequence of the purified chimeric polymerase according to SEQ ID NO. 44.

The invention also relates to a vector comprising any complete or partial nucleic acid sequence of SEQ ID NO: 5. The invention also relates to a vector comprising any complete or partial nucleic acid sequence of SEQ ID NO: 43. In a preferred embodiment it relates to a vector comprising the nucleic acid sequence according to SEQ ID NO. 5, wherein nucleotides may be aligned in such a way that the expressed protein retains its original activity. In a particularly preferred embodiment the vector contains a nucleic acid according to SEQ ID NO. 5. The same may be accomplished with SEQ ID NO. 43.

The invention also relates to a vector according to claim 10, wherein the vector comprises 1) a promoter element operable linked to an isolated nucleic acid encoding a DNA polymerase fully or partially comprising any one of the amino acid sequences SEQ ID NO: 6, 44, or 17-23, 2) ribosome binding site, 3) a selectable metabolic marker gene, 4) a origin of replication functional in a host cells and optionally 5) 3'-nontranslated sequence elements enhancing the translation of the nucleic acid sequence transcript encoding the DNA polymerase.

The invention relates to a nucleic acid replication kit comprising a) a thermophilic DNA polymerase I according to to the invention, optionally b) a reaction buffer, and c) optionally nucleotides.

In a preferred embodiment it relates to a nucleic acid replication kit according to claim 12, wherein the kit is selected from the group of a DNA sequencing kit and a DNA amplification kit and comprises a polymerase according to the invention.

Herein we disclose a number of nucleic acid and protein sequences which are listed below in FIG. 30.

A number of Teg DNA Pol I proteins of the invention are "derived from" the eubacteria *Thermus eggertssonii*. As used herein, a gene "of" or "derived from" a particular bacterial genus or species does not mean directly of or directly derived from a particular bacterial genus or species. Rather, the phrases refer to correspondence of the particular gene to an endogenous gene of the particular bacterial genus or species.

A Teg DNA Pol I protein is a "functional" polymerase. Functional refers to polymerase activity, which can be characterized by the rate (speed) at which a DNA polymerase is extending the 3'-terminus of a primer annealed to a single-stranded DNA template strand in 3'-5' direction, which is, e.g., the primer extension rate. In a preferred embodiment, a Teg DNA polymerase I of the invention is characterized by its ability to extend the primer 3'-terminus at a rate at least 5 bases/seconds faster than that of Taq DNA polymerase I under identical primer extension assay conditions. In specific embodiments, Teg DNA polymerases of the invention perform at extension rates equal or greater than 35 bases/second, more preferably greater than 40 bases/second, more preferably greater than 60 bases/second, more preferably greater than 70 bases/second, and most preferably greater than 80 bases/second nucleotides per second. The extension rates of type I DNA polymerases compared are measured at 60° C. in 20 µl reactions comprising 30 mM Bicine, 59 mM Tris (pH 8.7), 50 mM KCl, 2 mM magnesium acetate, 250 µmol dATP, 250 µmol dCTP, 250 µmol dGTP, 250 µmol dTTP, 375 ng (0.15 µmol) ssM13mp18 DNA (new England Biolabs, catalog if N4040S) and 3 pmol of M13 Reverse Sequencing Primer (SEQ ID NO: 41, New England Biolabs, catalog #S1233S) with 1 unit of the respective DNA polymerase I. The length of newly synthesized primer extension products in the reactions is determined in 30 seconds time intervals over a total time period of 5 minutes. The size (length) of the primer extensions product is measured by comparing their electrophoretic mobility in a 1% TEAE-buffered agarose gel against a double-stranded reference DNA molecule (M13mp18 RF I DNA, New England Biolabs, catalog #N4018S), which has the same size as the full-length primer extension products.)

The Teg DNA Pol I proteins of the invention are "thermostable" polymerases. Thermostable refers to a polymerase that is resistant to irreversible inactivation by temperatures higher than 80° C. DNA polymerases synthesize the formation of a DNA molecule complementary to a single-stranded DNA template by extending a primer in the 5' to 34 direction. A thermostable DNA polymerase is not necessarily totally resistant to heat inactivation, and, thus, heat treatment may reduce its DNA polymerase activity to some extent. Thermostable DNA polymerases are typically isolated from thermophilic bacteria, of which Teg is an example. In a preferred embodiment, a Teg DNA Pol I of the invention is as thermostable as Taq DNA Polymerase I and more thermostable than Thr DNA Polymerase I.

In a preferred embodiment, a Teg DNA polymerase of the invention demonstrates comparable or more preferably higher "fidelity" in comparison to Taq DNA polymerase I. As used herein, "fidelity", "DNA polymerase fidelity" and "polymerase fidelity" refers to the ability of a polymerase to discriminate against the incorporation of a "wrong" nucleotide at the 3'-terminus of the priming strand. A "wrong" nucleotide refers to a nucleotide with a base that can not engage in Watson/Crick-type hydrogen bonding with the opposing base in the template strand. Thermodynamic restrictions for conformational changes in the polymerase active site provide the underlying mechanism for "wrong base discrimination. The conformational restrictions are imposed by DNA helix distortions of a "Non-Watson-Crick" base pair. In the prior art, fidelity is often confused with the reverse numeric value of the error rate. The error rate of polymerase represents a complex parameter, which depends on the outcome of three different processes that all occur simultaneously during replication: incorporation of a mismatched base, excision of a mismatched base (e.g. exonuclease proof-reading) or extension of a mismatched base. Fidelity controls only the outcome of the first process. It takes the concerted action of mismatched base incorporation and mismatch extension to permanently fix a polymerase copy error in the replication product. Each of the 12 possible base mismatch combinations has specific helix distortion characteristics. Therefore, the synthesis fidelity of a given polymerase comprises the average of 12 individual mismatch base pair fidelities. A G/T base pair causes the lowest distortion in a DNA double helix compared to a standard Watson/Crick base pair. A G/G base pair is so distorted that it is almost impossible for a DNA polymerase to incorporate it into the helix of a nascent DNA chain during replication. Therefore discriminations against G/T base pair or a G/G base pair mark the lowest and highest fidelity extremes, respectively, among a panel of 12 theoretically possible mismatch base pairs. The generic fidelity of a DNA polymerase can be expressed as the average of the two extreme base pair fidelities. For many PCR-based applications, 3'-5' exonuclease-containing polymerases are used. This 3'-5' nuclease activity offers a proof reading function to correct for errors. Although fidelity can be estimated by competition between matched and mismatched dNTPs, a much more convenient approach is to measure kinetics of insertion for wrong and right dNTPs in separate reactions (Echols and Goodman, "Fidelity Mechanisms in DNA Replication," Annual Review of Biochemistry, 60:477-511, 1991, herein incorporated by reference). The ratio Kcat(w)/Km(w) to Kcat(r)/Km(r), where r represents the incorporation of the right nucleotide and w represents the incorporation of the wrong nucleotide, measures the misinsertion efficiency, f(ins). Fidelity of the enzyme is the reciprocal value of the f(ins).

$K_{CAT}$-maximum $$f_{ins} = \frac{K_{catw}/K_{mw}}{K_{catr}/K_{mr}}$$

$$\text{Fidelity} = \frac{1}{f_{ins}}$$

number of moles of substrate converted to a product per unit time per mole of enzyme $K_{CAT}/K_M$—Efficiency of converting a enzyme nucleotide complex into a product Km—substrate concentration when $V_{max}^{1/2}$ Teg DNA Pol I proteins of the invention comprises distinctive "domains". As used herein, "domain" refers to an element of overall structure that is self-stabilizing and often folds independently of the rest of the protein chain. Many domains are not unique to the protein products of one gene or one gene family but instead appear in a variety of proteins. Domains often are named and singled out because they figure prominently in the biological function of the protein to which they belong.

Many Teg DNA Pol I proteins of the invention comprise at least three distinctive domains, particularly, an N-terminal 5'-3' domain, an internal 3'-5'-exonuclease domain (without nuclease activity) and a polymerase domain. The polymerase domain typically resides in the C-terminal two-thirds of the protein and is responsible for both DNA-dependent and RNA-dependent DNA polymerase activities of the protein. The N-terminal one-third portion contains the 5'-3'-exonuclease domain. The palm subdomain of the polymerase domain consists of the amino acid positions 434-448, 556-615, 751-830; the thumb subdomain of the polymerase domain includes amino acid positions 449-555, while the fingers subdomain of the polymerase domain is formed by the remaining amino acid positions from 616 to 750 of SEQ ID NO: 6. The palm subdomain of the polymerase domain consists of the amino acid positions 438-452, 560-619, 755-834; the thumb subdomain of the polymerase domain includes amino acid positions 453-559, while the fingers subdomain of the polymerase domain is formed by the remaining amino acid positions from 620 to 754 of SEQ ID NO: 44 if codon optimized.

Teg DNA Pol I proteins of the present invention may be shorter or longer than the amino acid sequences exemplified, or encoded by the nucleic acid sequences exemplified.

Fragments of Teg DNA Pol I proteins included in the invention preferably share at least one antigenic epitope with Teg DNA Pol I, have at least the indicated sequence identity to Teg DNA Pol I, and have a Teg DNA Pol I protein activity as further defined herein.

In addition, as is more fully outlined below, Teg DNA Pol I proteins can be made that are longer than those exemplified, for example, by die addition of epitope or purification tags, the addition of other fusion sequences, or the elucidation of additional coding and non-coding sequences.

The Teg DNA Pol I proteins and nucleic acids of the present invention are preferably recombinant. As used herein and further defined below, nucleic acid may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded and single stranded sequence. As will be appreciated by those in the art, the depiction of a single strand ("Watson") also defines the sequence of the other strand ("Crick"); thus the sequences depicted in the figures also include the complement of the sequence.

By the term recombinant nucleic acid herein is meant nucleic acid, originally formed in vitro, in general, by the manipulation of nucleic acid by endonucleases, in a form not normally found in nature. Thus an isolated Teg DNA Pol I nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a recombinant protein is a protein made using recombinant techniques, i.e. through the expression of a recombinant nucleic acid as depicted above. The protein may be isolated or purified away from some or all of the proteins and compounds with which it is normally associated, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a Teg DNA Pol I proteins from *T. eggertssonii* in a different organism or host cell. The protein may be made at a significantly higher concentration than is normally seen, through the use of a inducible promoter or high expression promoter, such that the protein is made at increased concentration levels. The protein may be in a form not normally found in nature, as in the addition of an epitope tag, or amino acid substitutions, insertions and deletions, as discussed below.

In one embodiment, the coding sequence of Teg DNA polymerase I is synthesized, in whole or in part, using chemical methods well known in the art (Caruthers et al., Nuc. Acids Res. Symp. Ser., 7:215-233, 1980; Crea and Horn, Nuc. Acids Res., 9:2331, 1980; Matteucci and Caruthers, Tetrahedron Lett., 21:719, 1980; and Chow and Kempe, Nuc. Acids Res., 9:2807-2817, 1981). In other embodiments of the present invention, the protein itself is produced using chemical methods to synthesize either a full-length Teg DNA polymerase I amino acid sequence or a portion thereof. For example, peptides can be synthesized by solid phase techniques, cleaved from the resin, and purified by preparative high performance liquid chromatography (Creighton, Proteins Structures and Molecular Principles, W H Freeman and Co, New York N.Y., 1983). In other embodiments of the present invention, the composition of the synthetic peptides is confirmed by amino acid analysis or sequencing (Creighton, supra).

Direct peptide synthesis can be performed using various solid-phase techniques (Roberge et al., Science 269:202-204, 1995) and automated synthesis may be achieved, for example, using ABI 431A Peptide Synthesizer (Perkin Elmer) in accordance with the instructions provided by the manufacturer. Additionally, the amino acid sequence of Teg DNA polymerase I, or any part thereof, may be altered during direct synthesis and/or combined using chemical methods with other sequences to produce a variant polypeptide.

A number of naturally occurring Teg DNA Pol I proteins and nucleic acids are exemplified herein. These have been obtained from a number of strains of *Thermus eggertssonii*. Other Teg DNA Pol I proteins and nucleic acids of the invention may be identified in several ways. For example, a Teg DNA Pol I may be identified by its percent sequence identity to a Teg DNA Pol I exemplified herein, or by the percent identity of its encoding nucleic acid to a Teg DNA Pol I nucleic acid exemplified herein.

In one embodiment, the invention provides a Teg DNA Pol I protein having greater than 95%, more preferably at least about 96%, more preferably at least about 97%, more preferably at least about 98%, more preferably at least about 99% identity to a Teg DNA Pol I protein exemplified herein.

In another embodiment, the invention provides a Teg DNA Pol I protein that is encoded by a nucleic acid sequence having at least about 95%, more preferably at least about 96%, more preferably at least about 97%, more preferably at least about 98%, more preferably at least about 99% identity to a Teg DNA Pol I nucleic acid exemplified herein.

As is known in the art, a number of different programs can be used to identify whether a protein or nucleic acid has sequence identity or similarity to a known sequence. For a detailed discussion, see D. Mount, Bioimformatics, Cold Spring Harbor Press, Cold Spring Harbor, N.Y., 2001, ISBN 0-87969-608-7. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, PNAS USA 85:2444 (1988), by computerized implementations of these algorithms (GAP, BESIFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection. Preferably, percent identity is calculated by FastDLB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351-360 (1987); the method is similar to that described by Higgins & Sharp CABIOS 5:151-153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403-410, (1990) and Karlin et al., PNAS USA 90:5873-5787 (1993). A particularly useful BLAST program is the WU-BLAST-2 program which was obtained from Altschul et al., Methods in Enzymology, 266: 460-480 (1996)]. Wu-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389-3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits. A percent amino acid sequence identity value is determined by the number of matching identical residues divided by the total number of residues of the longer sequence in the aligned region. The longer sequence is the one having the most actual residues in the aligned region (gaps introduced by WU-Blast-2 to maximize the alignment score are ignored).

The alignment may include the introduction of gaps in the sequences to be aligned. In addition, for sequences which contain either more or fewer amino acids than the protein sequences set forth in the figures, it is understood that in one embodiment, the percentage of sequence identity will be determined based on the number of identical amino acids in relation to the total number of amino acids. Thus, for example, the percent sequence identity of sequences shorter than those shown in the figures will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of 0, which obviates the need for a weighted scale or parameters as described below for sequence similarity calculations. Percent sequence identity can be calculated, for example, by dividing the number of matching identical residues by the total number of residues of the shorter sequence in the aligned region and multiplying by 100. The longer sequence is the one having the most actual residues in the aligned region.

In a similar manner, percent (%) nucleic acid sequence identity is defined as the percentage of nucleotide residues in a candidate sequence that are identical with the nucleotide residues in a Teg DNA Pol I nucleic acid exemplified herein. A preferred method utilizes the BLASTN module of WU-BLAST-2 set to the default parameters, with overlap span and overlap fraction set to 1 and 0.125, respectively.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

By "nucleic acid" or oligonucleotide or grammatical equivalents herein means at least two nucleotides covalently linked together. A nucleic acid of the present invention will generally contain phosphodiester bonds, although in some cases, as outlined herein, particularly with respect to antisense nucleic acids or probes, nucleic acid analogs are included that may have alternate backbones, comprising, for example, phosphoramide (Beaucage, et al, Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lettn., 805 (1984), Letsinger, et al., J. Am. Chem. Soc., 110:4470 (1988); and Pauwels, et al., Chiemica Scripta, 26:141 (1986)), phosphorothioate (Mag, et al., Nucleic Acids Res., 19:1437 (1991); and U.S. Pat. No. 5,644,048), phosphoroditlioate (Briu, et al., J. Am. Chem. Soc., 111:2321 (1989)), O-methylphosphoroawidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et at, Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al, Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanglui and P. Dan Cook. Nucleic acids containing one or more carbocyclic sugars, as well as "locked nucleic acids", are also included within the definition of nucleic acids (see Jenkins, et al., Chem. Soc. Rev., (1995) pp. 169-176). Several nucleic acid analogs are described in Rawls, C & F News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hlypoxathanine, isocytosine, isoguanine, etc.

With respect to nucleic acids that encode Teg DNA Pol I proteins, it will be appreciated by those in the art that due to the degeneracy of the genetic code, an extremely large number of nucleic acids may be made, all of which encode the proteins of the present invention. Thus, having identified a particular amino acid sequence, those skilled in the art could make any number of different nucleic acids, by simply modifying the sequence of one or more codons in a way which does not change the amino acid sequence of the protein.

In a preferred embodiment, the present invention provides Teg DNA Pol I nucleic acids encoding Pol I proteins, which comprise a nucleotide sequence having at least about 98%, most preferably at least about 99% identity to a nucleotide sequence selected from the group consisting of SEQ ID NO: 5. In a very preferred embodiment, the present invention provides Teg DNA Pol I nucleic acids encoding Pol I proteins, which comprise a nucleotide sequence having at least about 98%, most preferably at least about 99% identity to a nucleotide sequence selected from the group consisting of SEQ ID NO: 43.

In an especially preferred embodiment, the invention provides Teg DNA Pol I nucleic acids encoding Teg DNA Pol I proteins, which comprise a nucleotide sequence selected from the group consisting of SEQ ID NO: 5. In an especially preferred embodiment, the invention provides Teg DNA Pol I nucleic acids encoding Teg DNA Pol I proteins, which comprise a nucleotide sequence selected from the group consisting of SEQ ID NO: 43.

In one embodiment, the invention provides Teg DNA Pol I nucleic acids encoding Teg DNA Pol I protein fragments described herein.

In some embodiments, Pol I nucleic acids may be identified through hybridization studies. Thus, for example, nucleic acids which hybridize under high stringency conditions to a nucleotide sequence selected from the group consisting of SEQ ID NO: 5, preferably 43, or to those which encode an amino acid sequence selected from the group consisting of SEQ ID NO: 5, preferably 43, or complements thereof, or fragments thereof or their complements, are considered Teg DNA Pol I nucleic acids. High stringency conditions are known in the art; see for example Sambrook et al., Molecular Cloning, A Laboratory Manual, 3rd edition, 2001, Cold Spring Harbor Press, Cold Spring Harbor, N.Y.; and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

Once isolated from its natural source, e.g., contained within a plasmid or other vector or excised therefrom as a linear nucleic acid segment, the recombinant Pol I nucleic acids can be used as precursor nucleic acids to make modified or variant nucleic acids and proteins.

Using the nucleic acids of the present invention, a variety of expression vectors are made. The expression vectors may be either self-replicating extrachromosomal vectors or vectors which integrate into a host genome. Generally, these expression vectors include transcriptional and translational regulatory nucleic acid operably linked to a nucleic acid encoding a Teg DNA Pol I protein. The term control sequences, refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the Pol I protein; for example, transcriptional and translational regulatory nucleic acid sequences from *Bacillus* are preferably used to express protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

Pol I proteins of the present invention may be produced by culturing a host cell transformed with an expression vector containing a Pol I nucleic acid under the appropriate conditions to induce or cause expression of the protein. The conditions appropriate for Pol I protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melonagaster* cells, *Saccharomyces cerevisiae* and other yeasts, *E. coli, Bacillus subtilis*, SF9 cells, C129 cells, 293 cells, *Neurospora*, BHK, CHO, COS, and HeLa cells, fibroblasts, Schwanoma cell lines, immortalized mammalian myeloid and lymphoid cell lines such as Jurkat and BJAB cells.

In one embodiment, Pol I proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for Teg DNA Pol I into mRNA. A promoter will have a transcription initiating region, which is usually placed proximal to the 5' end of the coding sequence, and a TATA box, using a located 25-30 base pairs upstream of the transcription initiation site. The TATA box is thought to direct RNA polymerase H to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, Pol I proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of Pol I into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the alt. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is called the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the Pol I protein in bacteria. The signal sequence typically encodes a signal peptide comprised of hydrophobic amino acids which direct the secretion of the protein from the cell, as is well known in the art. The protein is either secreted into the growth media (grain-positive bacteria) or into the periplasmic space, located between the idler and outer membrane of the cell (grain-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris,* and *Streptococcus lividans*, among others.

The bacterial expression vectors are transformed into bacterial host cells using techniques well known in the art, such as calcium chloride treatment, electroporation, and others.

In some embodiments, Pol I proteins are produced in insect cells. Expression vectors for the transformation of insect cells, and in particular, baculovirus-based expression vectors, are well known in the art.

In one embodiment, a Pol I protein is produced in yeast cells. Yeast expression systems are well known in the art, and include expression vectors for *Saccharomyces cerevisiae, Candida alans* and *C. maltosa, Hansenula polymorpha, Kluyveromyces fragilis* and *K. lactis, Picllia guillerimondii* and *P. pastoris, Schizosaccharomyces pombe,* and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, FHs4, LEU2, TRP1, and ALG7, which confers resistance to tunicamycin; the neomycin phosphotransferase gene, which confers resistance to G418; and the CUP1 gene, which allows yeast to grow in the presence of copper ions.

In a preferred embodiment, a Teg DNA polymerase I is "purified" or "isolated". As used herein, the purifying or isolating a DNA Pol I refers the removal of contaminants from a sample. DNA Pol I proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, chromatography, and chromatofocusing. For example, the Pol I protein may be purified using a standard anti-Teg DNA Pol I antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the Teg DNA Pol I protein. In some instances no purification will be necessary.

In a preferred embodiment, recombinant Teg DNA Pol I is expressed in mesophilic bacterial host cells and is purified by the removal of host cell proteins through heat treatment at temperatures between 70 to 80° C.; the percent of recombinant Teg DNA polymerase I is thereby increased in the sample. An isolated polypeptide refers to a polypeptide of the invention that (1) has been separated from at least about 50% of polynucleotide, lipid, carbohydrate, or other material with which it is naturally found when isolated from a source cell, (2) is not linked (by covalent or noncovalent interaction) to all or a portion of a polypeptide to which the isolated polypeptide is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

DNA Pol I Variants

In a preferred embodiment, the present invention provides Pol I protein variants. These variants fall into one or more of three classes: substitutional, insertional and deletional variants. These variants ordinarily are prepared by site specific mutagenesis of nucleotides in the DNA encoding a Pol I protein, using cassette or PCR mutagenesis or other techniques well known in the art, to produce DNA encoding the variant, and thereafter expressing the DNA in recombinant cell culture as outlined above. However, variant protein fragments may also be prepared by in vitro synthesis using established techniques. Amino acid sequence variants are characterized by the predetermined nature of the variation, a feature that sets them apart from naturally occurring allelic or interspecies Pol I proteins. In one embodiment, variants exhibit the same qualitative biological activity as the naturally occurring analogue. In a preferred embodiment, variants which have modified characteristics are provided, as will be more fully outlined below.

Which the site or region for introducing an amino acid sequence variation is predetermined, the mutation per se need not be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence are well known, for example, M13 primer mutagenesis and PCR mutagenesis. Screening of the mutants may be done using assays that measure Pol I activity, as described herein.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the Pol I protein are desired, substitutions are generally made in accordance with the following chart:

CHART I

| Original Residue | Exemplary Substitutions |
| --- | --- |
| Ala | Ser, Gly, Pro |
| Arg | Lys |
| Asn | Gln, His |
| Asp | Glu |
| Cys | Ser, Thr, Met |
| Gln | Asn, Ser, Thr, Glu, Asp |
| Glu | Asp |
| Gly | Pro, Ala, Ser, Thr |
| His | Asn, Gln, Tyr |
| Ile | Leu, Val, Ala, Met, Cys, Phe |
| Leu | Ile, Val, Ala, Met, Cys, Phe |
| Lys | Arg, Gln, Glu |
| Met | Leu, Ile, Val, Phe, Tyr, Ala |
| Phe | Met, Leu, Tyr, Trp, Ile, Val |
| Ser | Thr, Pro, Asn, Gln, Gly |
| Thr | Ser, Asn, Gln, Pro, Gly |
| Trp | Tyr, Phe, His |
| Tyr | Trp, Phe, His |
| Val | Ile, Leu, Phe, Ala, Met |

Substantial changes in function or immunological identity are made by selecting substitutions that are less conservative than those shown in Chart 1. For example, substitutions may be made which more significantly affect: die structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalaniyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

In one embodiment, variants that exhibit the same qualitative biological activity as the naturally-occurring analogue are provided.

In a preferred embodiment, the invention provides Pol I variants that exhibit an increased Pol I bioactivity as compared to the activity of a Pol I protein comprising an amino acid sequence selected from the group consisting of SEQ ID NOs: 2, 4, 6, 8, 10 and 12.

In another preferred embodiment, the invention provides Pol I variants that exhibit a decreased Pol I bioactivity as compared to the activity of a Pol I protein comprising an amino acid sequence selected from the group consisting of SEQ ID NOs: 2, 4, 6, 8, 10 and 12.

In preferred embodiments, Teg DNA Pol I can be altered by a variety of means to enhance, reduce or eliminate catalytic functions associated with any individual domain or combinations of domains. Suitable deletion and site-directed mutagenesis procedures are well known in the art.

In one embodiment, the invention provides a variant Teg DNA Pol I having reduced 5'-3' exonuclease activity. In a preferred embodiment, the glycine residue of the Teg Pol I variant corresponding to position 43 of SEQ ID NO. 6 is mutated to either aspartate or glutamate.

In one embodiment, the invention provides a variant Teg DNA Pol I having reduced 5'-3' exonuclease activity. In a preferred embodiment, the glycine residue of the Teg Pol I variant corresponding to position 47 of SEQ ID NO. 44 is mutated to either aspartate or glutamate.

In one embodiment the variant Teg DNA Pol I comprises an amino acid sequence having a substitution at position 679 of SEQ ID NO: 6 replacing the glutamic acid residue there by a positively charged amino acid such as lysine or arginine. In one embodiment the variant Teg DNA Pol I comprises an amino acid sequence having a substitution at position 683 of SEQ ID NO: 44 replacing the glutamic acid residue there by a positively charged amino acid such as lysine or arginine. Analysis of the three dimensional structure of Taq DNA polymerase I bound to a DNA substrate provided in the art has shown that the negative charge of the glutamic acid at the corresponding position (681) in the Taq DNA polymerase sequence SEQ ID NO: 2 contacts the negatively-charged phosphate backbone of the priming strand in the DNA substrate. That contact creates an electrostatic repulsion effect limiting the extension rate and processivity of the polymerase. Mutant variants of Taq DNA Pol I known in the art carrying a lysine instead of glutamic acid at that position have shown faster extension rates and better processivity. Variant Teg DNA polymerases with those features are desirable for various applications, such as fast PCR, DNA sequencing, amplification of long target sequences.

In one embodiment the variant Teg DNA Pol L comprises an amino acid sequence having single or combined substitutions at the positions 612-613 of SEQ ID NO: 6. In one embodiment the variant Teg DNA Pol I comprises an amino acid sequence having single or combined substitutions at the positions 616-617 of SEQ ID NO: 44. Random mutagenis experiments performed on Taq and E. coli DNA polymerase I in prior art have shown that the amino acid residues at the corresponding positions in their sequences control discrimination between rNTPs and dNTPs as polymerization substrates. They also control discrimination between RNA- or DNA-primed DNA templates, templates with base mismatches at the 3'-terminus of the primer and perfectly annealed primers and between labeled and non-labelled dNTP substrates. Based on the nature of the substitution(s) at these positions, a number of variant Teg DNA POl I can be provided with useful features for different applications. Variants with increased discrimination against the extension of mismatched primers are useful for allele-specific PCR. Variants with increased affinity for labeled ddNTP substrates are useful for fluorescent DNA sequencing and real-time PCR.

In one embodiment, the invention provides a variant Teg DNA Pol I having a reduced discrimination against the incorporation of dideoxyribonucleotides. Such a variant is useful for DNA sequencing. In a preferred embodiment, the Pol I variant comprises an amino acid sequence having a substitution residue in place of a wildtype phenylalanine in a position corresponding to position 665 of SEQ ID NO: 6. In a preferred embodiment, the substitution residue is a tyrosine. It is preferred that the same mutation is in SEQ ID NO. 44.

In one embodiment the invention provides a variant Teg DNA Pol I having substituted the C-terminal glycine residue at position 830 of SEQ ID NO: 6 by a glutamic acid residue. In one preferred embodiment the invention provides a variant Teg DNA Pol I having substituted the C-terminal glycine residue at position 834 of SEQ ID NO. 44 by a glutamic acid residue. Three dimensional structure of other *Thermus* DNA polymerases I having a C-terminal glutamic acid residue show that the beta carboxylic group of that residue is involved in stabilizing and coordinating a critical magnesium ion in the polymerase active site. Providing that additional carboxylic group reduces the effective magnesium concentration at which the variant Teg DNA polymerase I can carry out processive DNA synthesis. The ability to work at lower magnesium concentration is critical in polymerase chain reactions (PCR), because elevated magnesium concentrations have a negative impact on the specificity of DNA amplification PCR.

In one embodiment, the variant Teg DNA Pol I has 4 additional amino acid residues Met, Pro, Arg/Lys and Gly at the N-terminus of the amino acid sequence set forth in SEQ ID NO: 6. In one preferred embodiment, the variant Teg DNA Pol I has 4 additional amino acid residues Met, Pro, Arg/Lys and Gly at the N-terminus of the amino acid sequence set forth in SEQ ID NO: 44. Based on the deciphered three dimensional structure of Taq DNA polymerase bound to DNA substrate these three additional N-terminal residues are a part of the DNA-binding site in the N-terminal nuclease domain. In the absence of the additional N-terminal amino acids the Teg DNA polymerase has a weakened binding affinity and strength towards its DNA substrate. Teg DNA Pol I variants with strengthened DNA substrate binding properties have better processivity and a faster extension rate that Teg DNA Pol I with the wild type sequence set forth in SEQ ID NO:6. Unproved processivity and faster extension rates are important functional features of thermostable dNA polymerases used to perform the polymerase chain reaction (PCR) application. They allow for amplification of longer target sequences with higher sensitivity requiring less DNA template in the sample. The additional praline residue in position 2 of the variant Teg DNA Pol I in this embodiment stabilizes the recombinant polymerase against N-terminal degradation by endogenous cytoplasmic proteinases of the *E. coli* host cells according to the rules stabilizing N-terminal amino acid residues in *E. coli* well established in the prior art.

In some embodiments of the invention, deletion of amino acids from the protein is accomplished either by deletion in the encoding genetic material, or by introduction of a translational stop codon by mutation or frame shift. In other embodiments, proteolytic treatment of the protein molecule is performed to remove portions of the protein. In still further embodiments, deletion mutants are constructed by restriction digesting the wild-type sequence and introducing a new start site by annealing an appropriately designed oligomer to the digested fragment encoding the desired activity.

In one embodiment the variant Teg DNA Pol I is a truncated DNA Pol I lacking an N-terminal 5'-3'-exonuclease domain, wherein the DNA Pol I lacks 5'-3'-exonuclease activity. The truncated variant Teg DNA Pol I lacking exonuclease activity comprises essentially the amino acid sequence set forth by the residues 289 to 830 of SEQ ID NO: 6. A further truncated version of Teg DNA Pol I lacking exonuclease activity comprises essentially the amino acid sequence set forth by the residues 293 to 834 of SEQ ID NO: 44.

Covalent modifications of Pol I polypeptides are included within the scope of this invention. One type of covalent modification includes reacting targeted amino acid residues of a Pol I polypeptide with an organic derivatizing agent that is capable of reacting with selected side chains or the N- or C-terminal residues of the polypeptide. Derivatization with bifunctional agents is useful, for instance, for crosslinking Pol I to a water-insoluble support matrix or surface for use in a method for purifying anti-Pol I antibodies, or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutaminyl and aspartyl residues, respectively, hydroxylation of proline and lysine, phosphorylation of hydroxyl groups of seryl or threonyl residues, methylation of the amino groups of lysine, arginine, and histidine side chains [T. E. Creighton, Proteins; Structure and Molecular Properties, W.H. Freeman & Co., San Francisco, pp. 79-86 (1983)], acetylation of the N-terminal amine, and amidation of any C-terminal carboxyl group.

Another type of covalent modification of DNA Pol I protein contemplated by the invention comprises linking the polypeptide to one of a variety of nonproteinaceous polymers, e.g., polyethylene glycol, polypropylene glycol, or polyoxyalkylenes, in the manner set forth in U.S. Pat. No. 4,640,835; 4,496,689; 4,301,144; 4,670,417; 4,791,192 or 4,179,337.

DNA Pol I Fusion Proteins and DNA Pol I Chimeric Proteins

In some embodiments of the invention, the domains of the Teg DNA polymerase I can be used to create a "fusion protein" As used herein, the term "fusion protein" refers to a chimeric protein containing the protein of interest joined to an exogenous protein fragment. The fusion partner may enhance solubility of recombinant chimeric protein as expressed in a host cell, may provide an affinity tag to allow purification of the recombinant fusion protein from the host cell or culture supernatant, or both. The fusion partner may introduce novel desired functionalities missing in the parent polymerase, such as 3'-5'-proof-reading exonuclease activity to correct base misincorporations or additional DNA binding sites to improve the binding strength and affinity for the DNA template. Suitable examples of such fusion partners in the first case are the internal 3'-5'-exonuclease domains of archaic proof-reading DNA polymerases. Examples of fusion partners for the latter case are small thermostable histone-like proteins from thermophilic archae such as Ssod7 or the multiple DNA-binding domains from the DNA topoisomerase from *Methanococcus janaschii*. If desired, the fusion protein may be removed from the protein of interest by a variety of enzymatic or chemical means known to the art.

In some embodiments of the invention, the Teg DNA Polymerase I can be used to create a "chimeric protein". As used herein, the terms "chimeric protein" and "chimerical protein" refer to a single protein molecule that comprises amino acid sequence portions derived from two or more parent proteins. As used herein the term "portion" when used in reference to a protein (as in "a portion of a given protein") refers to fragments of that protein. The fragments may range in size from three amino acid residues to the entire amino acid sequence minus one amino acid. These parent molecules may be similar proteins from genetically distinct origins, different proteins from a single organism, or dissimilar proteins from different organisms.

Pol I polypeptides of the present invention may also be modified in a way to form chimeric molecules comprising a Pol I polypeptide fused to another, heterologous polypeptide or amino acid sequence. In one embodiment, such a chimeric molecule comprises a fusion of a Pol I polypeptide with a tag polypeptide which provides an epitope to which all anti-tag antibody can selectively bind. In a preferred embodiment, such a tag is the "flag tag" described below. The epitope tag is generally placed at the amino- or carboxyl-terminus of the Pol I polypeptide. The presence of such epitope-tagged forms of polypeptide can be detected using an antibody against the tag. Also, provision of the epitope tag enables the Pol I polypeptide to be readily purified by affinity purification using an anti-tag antibody or another type of affinity matrix that binds to the epitope tag. In an alternative embodiment, the chimeric molecule may comprise a fusion of a Pol I polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci. USA, 87:6393-6397 (1990)].

Pol I proteins may also be made as fusion proteins, using techniques well known in the art. Thus, for example, for the creation of monoclonal antibodies, if the desired epitope is small, the Pol I protein may be fused to a carrier protein to form an immunogen. Alternatively, the Pol I protein may be made as a fusion protein to increase expression, or for other reasons. For example, when the Pol I protein is a peptide, the nucleic acid encoding the peptide may be linked to other nucleic acid for expression purposes. Similarly, Pol I proteins of the invention can be linked to protein labels, such as green fluorescent protein (GFP), red fluorescent protein (RFP), blue fluorescent protein (BFP), yellow fluorescent protein (YFP), etc.

In some embodiments, the Pol I nucleic acids, and/or proteins, and/or antibodies of the invention are labeled. By labeled herein is meant that a compound has at least one element, isotope or chemical compound attached to enable the detection of the compound. In general, labels fall into four classes: a) isotopic labels, which may be radioactive or heavy isotopes; b) immune labels, which may be antibodies or antigens; c) colored or fluorescent dyes; d) magnetic moieties. The labels may be incorporated into the compound at any position.

Nucleic Acid Replication

In one aspect, the invention provides methods for replicating a nucleic acid molecule, comprising subjecting the nucleic acid molecule to a replication reaction in a replication reaction mixture comprising a Teg DNA Polymerase I Nucleic acid replication is a process by which a template nucleic acid molecule is replicated in whole or in part. Thus, the product of a nucleic acid replication reaction can be completely or partially complementary to the template nucleic acid molecule it is replicating. Nucleic acid replication is done by extending a primer hybridized to the template nucleic acid in the 5'-3' direction, incorporating nucleotides complementary to the bases of the template nucleic acid at each position in the extension product. The primer may be, for example, a synthetic oligonucleotide that hybridizes to a region of a single stranded DNA template. The primer may also be, for example, a portion of a single stranded DNA template that is complementary to a second region of the single stranded DNA template and can self-prime. Included within the scope of nucleic acid replication reactions are isothermal replication reactions, sequencing reactions, amplification reactions, thermocycling amplification reactions, PCR, fast PCR, and long range PCR.

The nucleic acid replicated in a nucleic acid replication reaction is preferably DNA, and replication preferably involves the DNA-dependent DNA polymerase activity of a Teg DNA polymerase I.

In a preferred embodiment, a reaction mixture provided herein comprises a zwitterionic buffer. In a preferred embodiment, the zwitterionic buffer has a pH between about pH 7.5-8.9. In a preferred embodiment, the buffer comprises a combination of an organic zwitterionic acid and an organic zwitterionic base, potassium ions, and magnesium ions.

In a most preferred embodiment, a reaction mixture provided herein comprises 30 mM Bicine, 59 μM Tris, 50 mM KCl, 2 mM magnesium acetate.

In nucleic acid replication reactions herein, the temperature at which primer extension is done is preferably between about 60-72° C., more preferably between about 62-68° C.

In a preferred embodiment, the temperature at which primer annealing and primer extension are done in a thermocycling amplification reaction is between about 60-72° C., more preferably between about 62-68° C., more preferably between about 62-65° C., though the optimum temperature will be determined by primer length, base content, degree of primer complementarity to template, and other factors, as is well known in the art.

In a preferred embodiment, the temperature at which denaturation is done in a thermocycling amplification reaction is between about 90-95° C., more preferably between 92-94° C. Preferred thermocycling amplification methods include polymerase chain reactions involving from about 10 to about 100 cycles, more preferably from about 25 to about 50 cycles, and peak temperatures of from about 90° C. to about 95° C., more preferably 92-94° C.i Nucleic Acid Amplification In one aspect, the invention provides methods for amplifying a nucleic acid molecule, comprising subjecting the nucleic acid molecule to an amplification reaction in an amplification reaction mixture comprising a Teg DNA polymerase I disclosed herein. Preferably, the amplification reaction is done in an amplification reaction tube described herein.

Nucleic acid molecules may be amplified according to any of the literature-described manual or automated amplification methods. As used herein "amplification" refers to any in vitro method for increasing the number of copies of a desired nucleotide sequence. The nucleic acid amplified is preferably DNA, and amplification preferably involves the DNA-dependent DNA polymerase activity of a Teg DNA polymerase I. More preferably, DNA amplification involves a variant Teg DNA polymerase I with a Gly to Glu amino acid substitution at the C-terminus and 4 additional amino acids (Met, Pro, Arg, Gly) at the N-terminus.

In one embodiment, nucleic acid amplification results in the incorporation of nucleotides into a DNA molecule or primer, thereby forming a new DNA molecule complementary to a nucleic acid template. The formed DNA molecule and its template can be used as templates to synthesize additional DNA molecules. As used herein, one amplification reaction may consist of many rounds of DNA replication. DNA amplification reactions include, for example, polymerase chain reactions ("PCR"). One PCR reaction may consist of 10 to 100 "cycles" of denaturation and synthesis of a DNA molecule. Such methods include, but are not limited to, PCR (as described in U.S. Pat. Nos. 4,683,195 and 4,683,202, which are hereby incorporated by reference), Strand Displacement Amplification ("SDA") (as described in U.S. Pat. No. 5,455,166, which is hereby incorporated by reference), and Nucleic Acid Sequence-Based Amplification ("NASBA") (as described in U.S. Pat. No. 5,409,818, which is hereby incorporated by reference). For example, amplification may be achieved by a rolling circle replication system which may even use a helicase for enhanced efficiency in DNA melting with reduced heat (see Yuzhakou et al., Cell 86:877-886 (1996) and Mok et al., J. Biol. Chem. 262:16558-16565 (1987), which are hereby incorporated by reference).

In a preferred embodiment, the temperature at which denaturation is done in a thermocycling amplification reaction is between about 90° C. to greater than 95° C., more preferably between 92-94° C. Preferred thermocycling amplification methods include polymerase chain reactions involving from about 10 to about 100 cycles, more preferably from about 25 to about 50 cycles, and peak temperatures of from about 90° C. to greater than 95° C., more preferably 92-94° C.

In a preferred embodiment, a PCR reaction is done using a Teg DNA Polymerase I to produce, in exponential quantities relative to the number of reaction steps involved, at least one target nucleic acid sequence, given (a) that the ends of the target sequence are known in sufficient detail that oligonucleotide primers can be synthesized which will hybridize to them and (b) that a small amount of the target sequence is available to initiate the chain reaction. The product of the chain reaction will be a discrete nucleic acid duplex with termini corresponding to the ends of the specific primers employed.

Any source of nucleic acid, in purified or nonpurified form, can be utilized as the starting nucleic acid, if it contains or is thought to contain the target nucleic acid sequence desired. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction using the same or different primers may be so utilized. The nucleic acid amplified is preferably DNA. The target nucleic acid sequence to be amplified may be only a fraction of a larger molecule or can be present initially as a discrete molecule, so that the target sequence constitutes the entire nucleic acid. It is not necessary that the target sequence to be amplified be present initially in a pure form; it may be a minor fraction of a complex mixture, such as a portion of the β-globin gene contained in whole human DNA or a portion of nucleic acid sequence due to a particular microorganism which organism might constitute only a very minor fraction of a particular biological sample. The starting nucleic acid may contain more than one desired target nucleic acid sequence which may be the same or different. Therefore, the method is useful not only for producing large amounts of one target nucleic acid sequence, but also for amplifying simultaneously multiple target nucleic acid sequences located on the same or different nucleic acid molecules.

The nucleic acid(s) may be obtained from any source and include plasmids and cloned DNA or RNA, as well as DNA or RNA from any source, including bacteria, yeast, viruses, and higher organisms such as plants or animals. DNA or RNA may be extracted from, for example, blood or other fluid, or tissue material such as corionic villi or amniotic cells by a variety of techniques such as that described by Maniatis et al., Molecular Cloning: A Laboratory Manual, (New York: Cold Spring Harbor Laboratory) pp 280-281 (1982).

Any specific (i.e., target) nucleic acid sequence can be produced by the present methods. It is only necessary that a sufficient number of bases at both ends of the target sequence be known in sufficient detail so that two oligonucleotide primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater the specificity of the primers for the target nucleic acid sequence, and, thus, the greater the efficiency of the process. It will be understood that the word primer as used hereinafter may refer to more than one primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code can be used for each strand. One primer from this collection will be homologous with the end of the desired sequence to be amplified.

In some alternative embodiments, random primers, preferably hexamers, are used to amplify a template nucleic acid molecule. In such embodiments, the exact sequence amplified is not predetermined.

In addition, it will be appreciated by one of skill in the art that one-sided amplification using a single primer can be done.

Oligonucleotide primers may be prepared using any suitable method, such as, for example, the phosphotriester and phosphodiester methods or automated embodiments thereof. In one such automated embodiment diethylophosphoramidites are used as starting materials and may be synthesized as described by Beaucage et al., Tetrahedron Letters, 22:1859-1862 (1981), which is hereby incorporated by reference. One method for synthesizing oligonucleotides on a modified solid support is described in U.S. Pat. No. 4,458,006, which is hereby incorporated by reference. It is also possible to use a primer which has been isolated from a biological source (such as a restriction endonuclease digest).

Preferred primers have a length of from about 15-100, more preferably about 20-50, most preferably about 20-40 bases.

The target nucleic acid sequence is amplified by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable denaturing method including physical, chemical, or enzymatic means. One physical method of separating the strands of the nucleic acid involves heating the nucleic acid until it is completely (>99%) denatured. Typical heat denaturation may involve temperatures ranging from about 80° C. to 105° C., preferably about 90° C. to about 98° C., still more preferably 93° C. to 95° C., for times ranging from about 1 to 10 minutes. Strand separation may also be induced by an enzyme from the class of enzymes known as helicases or the enzyme RecA, which has helicase activity and is known to denature DNA. The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), and techniques for using RecA are reviewed in C. Radding, Ann. Rev. Genetics, 16:405-37 (1982), which is hereby incorporated by reference.

If the original nucleic acid containing the sequence to be amplified is single stranded, its complement is synthesized by adding oligonucleotide primers thereto. If an appropriate single primer is added, a primer extension product is synthesized in the presence of the primer, a Teg DNA polymerase I, and the four nucleotides described below. The product will be partially complementary to the single-stranded nucleic acid and will hybridize with the nucleic acid strand to form a duplex of unequal length strands that may then be separated into single strands, as described above, to produce two single separated complementary strands.

If the original nucleic acid constitutes the sequence to be amplified, the primer extension product(s) produced will be completely complementary to the strands of the original nucleic acid and will hybridize therewith to form a duplex of equal length strands to be separated into single-stranded molecules.

When the complementary strands of the nucleic acid are separated, whether the nucleic acid was originally double or single stranded, the strands are ready to be used as a template for the synthesis of additional nucleic acid strands. This synthesis can be performed using any suitable method. Generally, it occurs in a buffered aqueous solution. In some preferred embodiments, the buffer pH is about 7.5-8.9. Preferably, a molar excess (for cloned nucleic acid, usually about 1000:1 primer:template, and for genomic nucleic acid, usually about $10^6$:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

Nucleoside triphosphates, preferably dATP, dCTP, dGTP, diTP and/or dUTP are also added to the synthesis mixture in adequate amounts.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

New nucleic acid is synthesized on the single-stranded molecules. Additional polymerase, nucleotides, and primers may be added if necessary for the reaction to proceed under the conditions described above. Again, the synthesis will be initiated at one end of the oligonucleotide primers and will proceed along the single strands of the template to produce additional nucleic acids.

The steps of strand separation and extension product synthesis can be repeated as often as needed to produce the desired quantity of the specific nucleic acid sequence. The amount of the specific nucleic acid sequence produced will increase in an exponential fashion.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this manner, each of the two different specific sequences can be produced exponentially by the present process. Of course in instances where terminal sequences of different template nucleic acid sequences are the same, primer sequences will be identical to each other and complementary to the template terminal sequences.

Additionally, as mentioned above, in an alternative embodiment, random primers, preferably hexamers, are used to amplify a template nucleic acid molecule.

Additionally, one-sided amplification using a single primer may be done.

The present invention can be performed in a step-wise fashion where after each step new reagents are added, or simultaneously, wherein all reagents are added at the initial step, or partially step-wise and partially simultaneously, wherein fresh reagent is added after a given number of steps. Additional materials may be added as necessary, for example, stabilizers. After the appropriate length of time has passed to produce the desired amount of the specific nucleic acid sequence, the reaction may be halted by inactivating the enzymes in any known manner or separating the components of the reaction.

Thus, in amplifying a nucleic acid molecule according to the present invention, the nucleic acid molecule is contacted with a composition preferably comprising a thermostable Teg DNA polymerase I in an appropriate amplification reaction mixture.

In one embodiment, the invention provides methods of amplifying large nucleic acid molecules, by a technique commonly referred to as "long range PCR" (Barnes, W. M., Proc. Natl. Acad. Sci. USA, 91:2216-2220 (1994) ("Barnes"); Cheng, S. et. al., Proc. Natl. Acad. Sci. USA, 91:5695-5699 (1994), which are hereby incorporated by reference). In one method, useful for amplifying nucleic acid molecules larger than about 5-6 kilobases, the composition with which the target nucleic acid molecule is contacted comprises not only a Teg DNA polymerase I, but also comprises a low concentration of a second DNA polymerase (preferably thermostable repair type polymerase, or a polC α subunit) that exhibits 3'-5' exonuclease activity ("exo+" polymerases), at concentrations of about 0.0002-200 units per milliliter, preferably about 0.002-100 units/mL, more preferably about 0.002-20 units/mL, even more preferably about 0.002-2.0 units/mL, and most preferably at concentrations of about 0.40 units/mL. Preferred exo+polymerases for use in the present methods are *Thermotoga maritima* PolC, Pfu/DEEPVENT or Tli/NENT™ (Barnes; U.S. Pat. No. 5,436,149, which are hereby incorporated by reference); thermostable polymerases from *Thermotoga* species such as Tma Pol I (U.S. Pat. No. 5,512,462, which is hereby incorporated by reference); and certain thermostable polymerases and mutants thereof isolated from *Thermotoga neapolitana* such as Tne (3'exo+). The PolC product of *Thermus thermophilus* is also preferred. For a discussion of long range PCR, see for example, Davies et al., Methods Mol. Biol. 2002; 187: 51-5, expressly incorporated herein by reference.

Nucleic Acid Sequencing

In one aspect, the invention provides methods for sequencing a nucleic acid, preferably DNA, comprising subjecting the nucleic acid to a sequencing reaction in a sequencing reaction mixture comprising a Teg DNA Polymerase Preferably the Teg DNA polymerase I used lacks 3'-5' exonuclease activity capable of removing 31 terminal dideoxynucleotides in the sequencing reaction mixture.

Further, for sequencing it is preferred that the Teg variant according to the invention is applied. This Teg Pol I variant according to the invention comprises an amino acid sequence having a substitution residue in place of a wildtyp phenylalamine in a position corresponding to position 665 of SEQ ID NO. 6. In a preferred embodiment, the substitution residue is a tyrosine. It also preferred to have said substitution in SEQ ID NO. 43.

Nucleic acid molecules may be sequenced according to any of the literature-described manual or automated sequencing methods. Such methods include, but are not limited to, dideoxy sequencing methods ("Sanger sequencing"; Sanger, F., et al., J. Mol. Biol., 94:444-448 (1975); Sanger, F., et al., Proc. Natl. Acad. Sci. USA, 74:5463-5467 (1977); U.S. Pat. Nos. 4,962,022 and 5,498,523, which are hereby incorporated by reference), as well as by PCR based methods and more complex PCR-based nucleic acid fingerprinting techniques such as Random Amplified Polymorphic DNA ("RAPD") analysis (Williams, J. G. K., et al., Nucl. Acids Res., 18(22):6531-6535, (1990), which is hereby incorporated by reference), Arbitrarily Primed PCR ("AP-PCR") (Welsh, J., et al., Nucl. Acids Res., 18(24):7213-7218, (1990), which is hereby incorporated by reference), DNA Amplification Fingerprinting ("DAF") (Caetano-Anolles et al., Bio/Technology, 9:553-557, (1991), which is hereby incorporated by reference), microsatellite PCR or Directed Amplification of Minisatellite-region DNA ("DAMD") (Heath, D. D., et al., Nucl. Acids Res., 21(24): 5782-5785, (1993), which is hereby incorporated by reference), and Amplification Fragment Length Polymorphism ("AFLP") analysis (Vos, P., et al. Nucl. Acids Res., 23(21):4407-4414 (1995); Lin, J. J., et al., FOCUS, 17(2):66-70, (1995), which are hereby incorporated by reference).

Once the nucleic acid molecule to be sequenced is contacted with the Teg DNA Polymerase I in a sequencing reaction mixture, the sequencing reactions may proceed according to protocols disclosed above or others known in the art.

Kits

In one aspect, the invention provides kits for nucleic acid replication utilizing a Teg DNA polymerase I as disclosed herein. The kit according to the invention comprises at least comprise a DNA polymerase I according to the invention as disclosed herein.

In a preferred embodiment, the nucleic acid amplification kit includes buffers, nucleotides or buffers with nucleotides as described herein.

A nucleic acid sequencing kit according to the present invention comprises a Teg DNA polymerase I and preferably dideoxynucleotide triphosphates. The sequencing kit may further comprise additional reagents and compounds necessary for carrying out standard nucleic acid sequencing protocols, such as pyrophosphatase, agarose or polyacrylamide media for formulating sequencing gels, and other components necessary for detection of sequenced nucleic acids (See U.S. Pat. Nos. 4,962,020 and 5,498,523, which are directed to methods of DNA sequencing).

A nucleic acid amplification kit preferably comprises a Teg DNA polymerase I and dNTPs. The amplification kit may further comprise additional reagents and compounds necessary for carrying out standard nucleic acid amplification protocols (See U.S. Pat. Nos. 4,683,195 and 4,683,202, directed to methods of DNA amplification by PCR; incorporated herein by reference).

In additional preferred embodiments, the nucleic acid replication kits of the invention may further comprise a second DNA polymerase having 3'-5' exonuclease activity. Preferred are Pfu/DEEPVENT, Tli/VENT™, Tma, Tne(3'exo+), and mutants and derivatives thereof. Also preferred is PolC.

In one embodiment, the nucleic acid amplification kits may further comprise components needed to carry out PCR application using "degenerate primes". The term "degenerate primer" refer to primers which have a number of options at several positions in the sequence so as to allow annealing to and amplification of a variety of homologous sequences with base polymorphisms. i.e.:

(SEQ ID NO. 35)
5'-TCG AAT TCI CCY AAY TGR CCN T-3'

Y=pyrimidines C/T (degeneracy=2×)
R=purines=A/G (degeneracy=2×)
I=Inosine=C G/A/T
N=Nucleotide=C/G/A/T (degeneracy=4×)

There is evidence of highly conserved regions or motifs of amino acids that can be designed into degenerate primers; these regions may be conserved interspecies. Degenerate primers can then be used to fish out these sequences. Sequences amplified this way can then be sequenced to confirm that the sequence is correct. They can then be used as probes to fish out the gene of interest from a genomic library (prokaryotic) or a cDNA library (eukaryotic).

In one embodiment, die nucleic acid amplification kits may further comprise components needed to carry out "real-time PCR" applications. The term "real-time PCR" describes a system based on the detection and quantitation of a fluorescent signal. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed. A significant increase in fluorescence above the baseline value measured during the 3-15 cycles indicates the detection of accumulated PCR product. Components include, but are not limited to intercalation dyes, fluorescently labeled primers and probes, and derivatives of the same.

Kits of the present invention may include information pamphlets.

Vectors and Host Cells

The present invention provides vectors containing the polynucleotide molecules of the invention, as well as host cells transformed with such vectors. Any of the polynucleotide molecules of the invention can be contained in a vector, which generally includes a selectable marker and an origin of replication. The vectors further include suitable transcriptional and/or translational regulatory sequences, such as those derived from microbial or viral molecules. Examples of such regulatory sequences include transcriptional promoters, operators, or enhancers, mRNA ribosomal binding sites, and appropriate sequences. A promoter nucleotide sequence is operably linked to an encoding DNA sequence if the promoter nucleotide sequence directs the transcription of the encoding sequence.

Selection of suitable vectors for the cloning of molecules encoding the target polypeptides of the invention will depend upon the host cell in which the vector will be transformed, and, where applicable, the host cell from which the target polypeptide is to be expressed. Suitable host cells have been discussed above, but include prokaryotes, yeast, and other like organisms. Specific examples include bacteria of the genera *Escherichia, Bacillus* and *Salmonella*, as well as members of the genera *Pseudomonas, Streptomyces*, and *Staphylococcus*; yeast from the genera *Sacchoromyces, Pichia*, and *Kluveromyces*.

Teg DNA polymerase I of the present invention may be recombinantly joined sequences encoding heterologous proteins or peptides, to generate fusion protein constructs. Such heterologous proteins or peptides may be included to allow for example, enhanced purification, increased secretion, or increased stability. For example, a nucleic acid sequence encoding a signal peptide (secretory leader) may be fused in-frame to a Teg DNA Polymerase I sequence so that a Teg DNA polymerase I is translated as a fusion protein comprising the signal peptide.

Modification of a Teg DNA polymerase I encoding polynucleotide molecule of the invention to facilitate insertion into a particular vector, ease of use in a particular expression system or host (for example, by modifying restriction sites), and the like, are known and are contemplated for use in the invention. Genetic engineering methods for the production of Teg DNA Polymerase I polypeptides include the expression of the polynucleotide molecules in cell free expression systems, in cellular systems, in host cells, in tissues, and in animal models.

Antibodies

The novel polypeptides of the present invention, and segments thereof, may be used to raise polyclonal and monoclonal antibodies. Methods for the design and production of antibodies are known in the art, see for example, Antibodies: A Laboratory Manual, Harlow and Land (eds.), 1988 Cold Spring Harbor Laboratory Press, Cold Spring Harbor, New York; Monoclonal Antibodies, Hybridomnas: A New Dimension in Biological Analysis, Kennet et al (eds), 1980 Plenum Press, New York.

EXAMPLES

Example One

Identification of a Novel *Thermus* Species—*T. eggertssoii*—by Means of "Phenotypic Characterization, Multilocus Enzyme Electrophoresis" (MLEE) and 16S rRNA Phylogenetic Analysis of Environmental Isolates from Geothermal Sites in Iceland A total of 101 natural bacterial isolates were isolated from water and sediment samples in 8 separate geothermal regions in Iceland, including coastal areas (Snaefellsnes, Oxarijordur and Reykjanes) and both lowland (Hveragerdi) and highland regions (Hveravellir, Hrafntinnusker and Hagongur). These sites were variable in vegetation and in overall physicochemical properties covering a wide range of pH and temperature, different water activities and chemical composition. Three hours after sampling, samples were streaked on media R2A and 160 and incubated at 72° C. and 78° C. for 1-2 d (Skirnisdottir et al. 2000c) Reasoner and Geldreich 1985). Light yellow colonies were picked and purified by repeated streaking onto medium 160. Growth and characteristic tests were done in liquid medium 160 or on 160 agar plates at 72° C. After 1 day incubation on media 160 and R2A at 72 and 78° C., light yellow colonies, 2-3 mm in diameter appeared. The resulting colonies were further purified on medium 160.

Multilocus enzyme electrophoresis (MLEE) analysis was carried out first in order to associate the 101 *Thermus* spec. isolates with distinct genetic/taxonomic lineages. Therefore, this study included reference strains deposited in culture collections, which were isolated from different parts of the world. *Thermus aquaticus* strain YT-1 (type strain, DSM 625) isolated in Yellowstone National Park, U.S.A., *Thermus filiormis* strain Wai33 A.1 (type strain, DSM 4687, ATCC 43280) isolated in New Zealand, *Thermus thermophilus* strain HB8 (type strain, DSM 579, ATCC 27634; previous name was *Flavobacterium thermophilum*) isolated in Japan, *Thermus flavus* strain AT-62 (DSM 674, ATCC 33923) isolated in Japan, *Thermus brockianus* strain YS38 (type strain NCIMB 12676) isolated from hot springs in Yellowstone National Park, U.S.A., *Thermus* sp. Strain X-1 (ATCC 27978) isolated from manmade geothermal systems in U.S.A. and *Thermus scotoductus* strain SE-1 (type strain ATCC 51532) isolated from hot tap water in Iceland.

Multilocus enzyme electrophoresis (MLEE) is an electrophoretic technique used to map the distribution of different alleles of a number of enzymes in a given population. Genetic relationships are calculated from similarity in genotype on the basis of percentage of shared alleles. MLEE is an inexpensive technique capable of processing large numbers of samples at the same time. It is comparable with DNA: DNA hybridization in delineating species but as a taxonomic tool more appropriate for hierarchical classification as it is very sensitive at and below the species level. Cells for MLEE analysis were prepared by the following method.

After purification, isolates were grown overnight at 65° C. on medium 160 agar plates and harvested by scraping. The cells were suspended in TE buffer (10 mM Tris-HCl and 1 mM EDTA, pH 8.0) giving about 1 g in 5 ml and then disrupted in a French Press at 700 psi. The crude extract was centrifuged at 20000×g for 30 min at 4° C. and the supernatant collected and kept at −80° C. until use. Before use, the samples were spun again and the clear supernatant collected. The samples were run on 7.5% (w/v) polyacrylamide gels and after running the gels were assayed for alkaline phosphatase (AP), aspartate aminotransferase (AAT), esterase (EST) (non specific), glucose-6-phosphate isomerase (GPI), hexokinase (HK), isocitrate dehydrogenase (EDH), malate dehydrogenase (MDH), nucleoside phosphorylase (NP), superoxide dismutase (SOD) and an unspecific dehydrogenase (JDH). Demonstration of the enzyme stainings has been described elsewhere except 0.2 M Tris buffer (pH 8.0) was used here (Manchenko 1994; Petursdottir et al. 2000). Distinctive electromorphs of each enzyme, numbered in order of decreasing anodal mobility were equated with alleles at the corresponding structural gene locus. An absence of enzyme activity was attributed to a null allele. Distinctive combinations of alleles over the 10 enzyme loci (multilocus genotypes) were designated as electrophoretic types (ETs).

Genetic diversity and phylogenetic relationships among the 101 *Thermus* strains characterized by multilocus enzyme electrophoresis was analyzed by two computer software packages, ETDIV and ETCLUS, kindly provided by the author, Dr. T. S. Whittam. Genetic diversity at an enzyme locus among either ETs or isolates was calculated from the allele frequencies among ETs or isolates as $h=(1-\Sigma xi2)(n/n-1)$ where $xi$ is the frequency of the ith allele and n is the number of ETs or isolates. Mean genetic diversity (H) is the arithmetic average of h values over all loci. HS, the within group diversity was calculated as the mean of the diversity values obtained for the separate sampling sites (subpopulations). Total genetic diversity, HT is the diversity value calculated for the population as a whole. For a subdivided population the total diversity HT will be greater than the diversity within subpopulations. Nei's coefficient of genetic differentiation (Nei et al. 1983) GST, was then calculated as (HT-HS)/HT using the ETDIV software. This coefficient indicates how big proportion of the overall variation is due to differences between subsamples. A dendrogram based on the average linkage algorithm of all the isolates with the reference strains included was made (see figures). Distance was measured as the proportion of mismatched loci between pairs of ETs. Genetic distance between pairs of ETs was expressed as the proportion of enzyme loci at which dissimilar alleles occurred (mismatches) and clustering of ETs was performed from a matrix of genetic distances by the average linkage method (UPGMA) (Caugant et al. 1987; Petursdottir et al. 2000). The results of MLEE analysis are summarized in the Figures.

Table 1 Allele frequencies within *Thermus lineages* for different loci

Based on MLEE analysis of 101 Icelandic *Thermus* strains, 7 distinct and genetically highly divergent populations of *Thermus* were observed (see figures). Six of the lineages could be assigned to validly described *Thermus* species that have previously been found in Iceland, *T. brockianus, T. thermophilus, T. oshimai, T. scotoductus, T. antranikianii* and *T. igniterrae. T aquaticus* and *T. filiformis* seem to have no close relatives in Iceland. One lineage of 5 isolates apparently represents a new *Thermus* species.

The phenotypic and physiological analysis was carried out on a subset of the isolates from the MLEE analysis. The isolates chosen for this analysis were selected to represent a number of different clones of the same lineages and from different geographic regions.

Cell morphology was analyzed by phase-contrast microscopy in exponential growth phase after growth in medium 160. Colony morphology was determined on medium 160 agar plates after 18 h growth at 65° C. for all the strains. All strains were Gram-stained.

Growth was examined at temperatures 50, 65 and 78° C. on medium 160 plates. Growth was analyzed at pH 5.0, 6.0, 8.0, 8.7 and 9.5 on medium 160 agar plates and the pH was adjusted with HCl and NaOH.

Salt and ion tolerance was tested on medium 160 agar plates supplied with 0.5, 1 and 2% NaCl, 50 mM $MgSO_4$, 50 mM $CaSO_4$, 2 mM $CuSO_4$, 50 mM $Na_2SO_4$, 50 mM $Na_2SO_3$ and 50 mM $Na_2S_2O_3$. Growth in the presence of the chelating agent EDTA was analyzed on medium 160 agar plates supplemented with 2 and 5 mM EDTA.

Utilization of single carbon sources was tested on minimal medium agar plates containing 0.2-0.4% organic compound as described before (Kristjansson et al. 1994; Petursdottir et al. 1996). Growth was examined on the following single carbon sources: acetate, arabinose, arginine, asparagine, aspartate, casein, citrate, formic acid, fructose, galactose, glutamate, glutamine, glucose, glycerol, histidine, alpha-ketoglutaric acid, lactose, leucine, lysine, malate, maltose, ornithine, proline, pyruvate, raffinose, rhamnose, serine, sorbitol, succinate, sucrose, starch, tartrate, tireonine, valine, and xylose.

The susceptibility to antibiotics was tested on medium 160 plates. Oxoid 6 mm disks with ampicillin (10 µg), bacitracin (10 U), chloramphenicol (30 µg), gentamicin (10 µg), nalidixic acid (30 µg), penicillin-G (10 U), rifampicin (2 µg), streptomycin (10 µg), tetracyclin (30 µg) and vancomycin (30 µg) were used. The diameter of the inhibition zone was measured and scored sensitive according to Oxoid standard values. Growth was examined in all the above tests after 1, 3 and 5 day incubation.

Nitrate reduction was tested with 2 and 5 day old cultures as described before with the modification of using microtiter plates (Smibert et al. 1994). Cell morphology was analyzed by phase-contrast microscopy in exponential growth phase in medium 160.

Colony morphology was determined on medium 160 agar plates after 18 h growth. The colonies of the new *Thermus* spec. lineage had a distinctive spreading colonial morphology and had a paler yellow pigmentation than many other *Thermus* species sampled from the same habitats.

Single rods were seen by phase-contrast microscopy. The cells were of variable sizes, between 2 and 4 µm long and 0.6-0.8 µm in diameter.

The optimum growth temperature for colonies of the new *Thermus* spec. lineage on plates was at about 70° C. The maximum growth temperature on plates was at about 84° C. and the lowest growth temperature was at 40° C. However, in liquid maximum growth temperature was at 82° C. and no growth occurred below 42° C. All strains of the new *Thermus* spec. had a pH range of growth from about 4.9 to 9.8, with a wide pH optimum range.

Results of salt tolerance testing and carbonsource utilization are shown in FIGS. 4a and 4b. All strains of the new *Thermus* spec. lineage grew in 0.5 and 1% NaCl but not at 2% salt concentration. Out of the 36 different compounds tested as single carbon sources, all new *Thermus* spec. strains were able to utilize acetate, arabinose, arginine, formic acid, galactose, glutamine, glucose, glycerol, proline, pyruvate, sorbitol, sucrose, starch and xylan remazol brilliant blue. One strain of the new *Thermus* spec. lineage, IT-2795, was also able to utilize histidine and leucine.

All of the new *Thermus* spec. strains tested resistant to rifampicin and nalidixic acid, but strain IT-2795 was also resistant to gentamicin (see FIG. 4b).

Presence of catalase activity was tested with 3% (v/v) hydrogen peroxide solution and oxidase activity was determined by the oxidation of 1% (w/v) tetramethyl-p-phenylenediaamine at room temperature (Smibert and Krieg 1994). All strains were Grain-negative and did not produce spores. All strains of the new *Thermus* spec. were positive for oxidase, catalase and nitrate reduction. As the most distinctive phenotypic characteristic, none of the five new *Thermus* spec. strains was capable of thiosulfate oxidation, while the majority of strains from *T. brockianus, T. thermophilus, T. ignitterae, T. scotoducttus, T. oshimai* isolated from the same habitates tested positive for thiosulfate oxidation (see FIG. 5).

Strains for the phylogenetic studies were selected on the basis of the UPGMA clustering obtained by the MLEE analysis. The phylogenetic position of a few representatives of each lineage was determined by using the 16S rRNA gene as the phylogenetic marker by partial sequencing. The following strains were analyzed: 165, 220, 346, 2101, 2103, 2120, 2123, 2121, 2126, 2127, 2133, 2135, 2789, 2791, 2795, and 6230. DNA was isolated with a Dynabeads DNA Direct Kit (Dynal) according to the manufacturer. By using DyNAzyme polymerase (Finnzymes) as described by the manufacturer, PCR amplifications of the 16S rRNA gene were performed. The primer set consisted of F9 and R1544 (Skirnisdottir et al. 2001). The reactions were as follows: 25 cycles at 95° C. for 50 s, 52° C. for 50 s and 72° C. for 3 min. Before sequencing of the PCR products, they were purified with QIAquick PCR Purification Kit (QIAGEN) as described by the manufacturer. The 16S rRNA genes from strains were sequenced with an ABI 377 DNA sequencer by using BigDye Terminator Cycle Sequencing Ready Reaction kit according to the manufacturer (PE Applied Biosystems). Primer R805 (5'-GACTAC-CCGGGTATCTAATCC'-3; 805-785) (SEQ ID NO: 42) was used for the sequencing. After BLAST searches, the sequences were manually aligned with other sequences within the *Thermus* group obtained from the Ribosomal Database Project (Maidak et al. 1999) and by using the ARB database alignment from the Department of Microbiology of the Technical University in Munich, Germany (W. Ludwig). Homologous nucleotide positions, based on the filter of the ARB database were included in the alignment and used for the comparative analysis. Evolutionary distances were computed from pairwise similarities by using the correction of Jukes and Cantor (Jukes et al. 1969). Distance trees were constructed by the neighbour-joining algorithm.

The GenBank accession numbers of the 16S rRNA sequences of the organisms used in this analysis are as follows: *Thermus scotoductus* SE-1 (AF032127), *Thermus* sp. NMX2 A.1 (L09661), *Thermus* sp. ViI7 (Z15061), *Thermus antranikianii* HN3-7 (Y18411), *Thermus* sp. ac-1 (L37520), *Thermus igniterrae* RF-4 (Y18406), SR1248 (AF255591), *Thermus aquaticus* YT-1 (L09663), unidentified *Thermus* OPB31 (AF027020), *Thermus* sp. α-7 (L37522), unidentified *Thermus* OPB32 (AF027021), *Thermus* YSPID A.1 (L10070), unidentified *Thermus* OPB19 (AF027019), *Thermus thermophilus* HB-8 (X07998), *Thermus filiformis* WAI 33 A.1 (X58345), *Thermus* sp. YS38 (Z15062), T oshimai SPS-17 (Y18416), *Thermus* YSPID A.1 (L10070), *Thermus* ZHGIB A.4 (L10071), *Thermus flavus* AT-62 (L09660), *Thermus* sp. Tok8 A.1 (L09666), *Thermus* sp. Tok20 A.1 (L09665), *Thermus* sp. W28 A.1 (L10068) and *Thermus* sp. T351 (L09671).

Figure 7A:
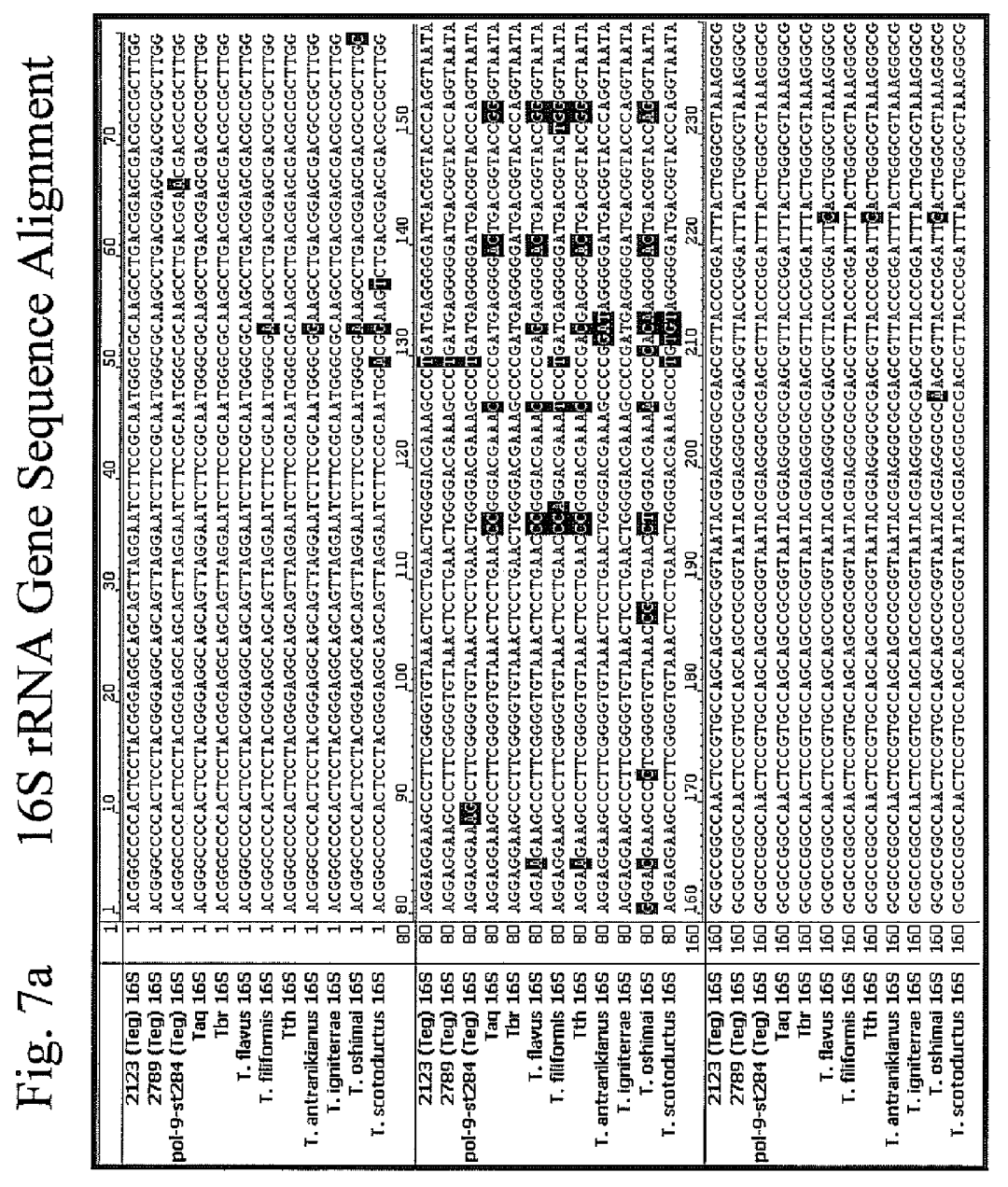
Figure 7B:
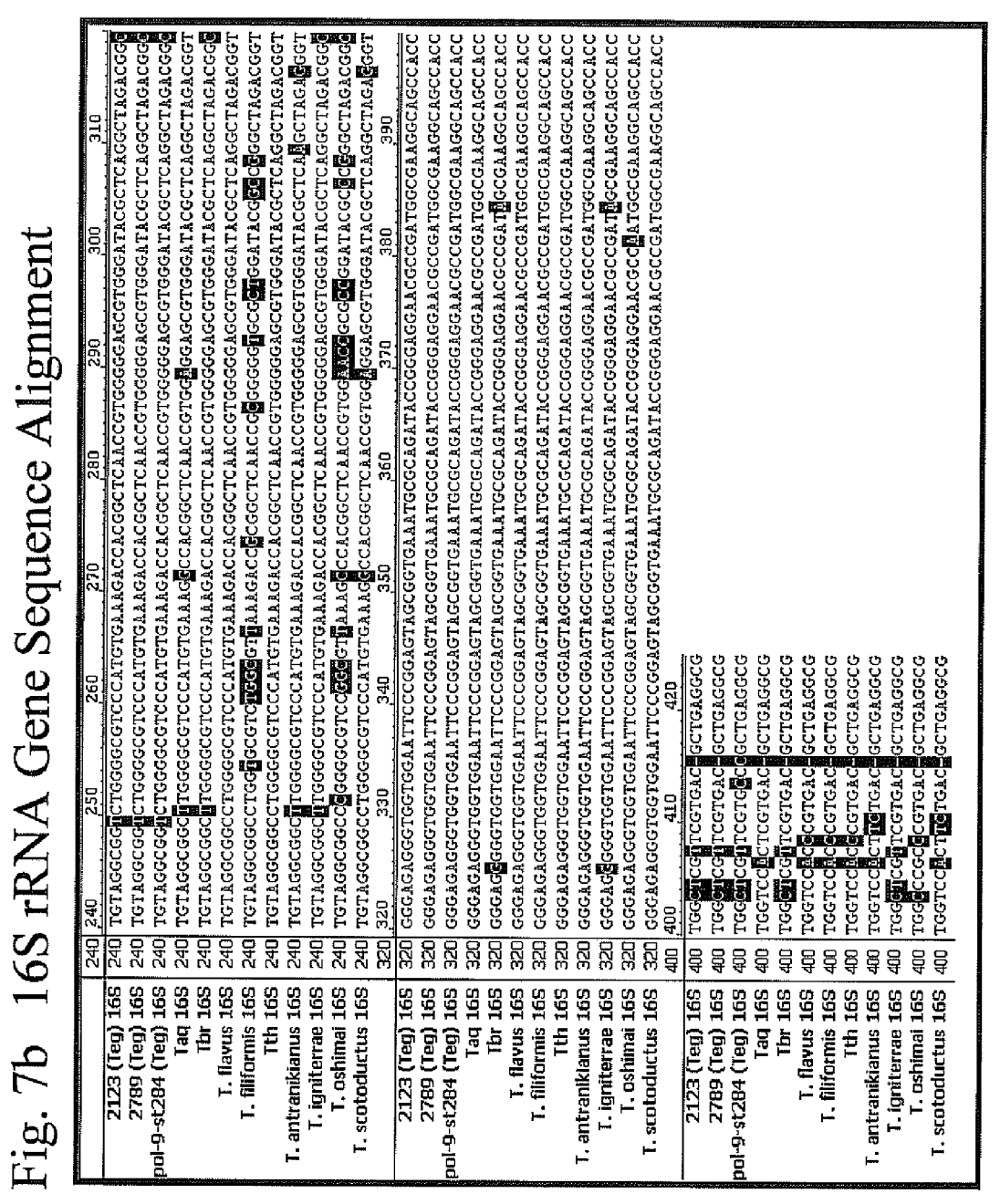

The phylogenetic dendrograms of the *Thermus* isolates and reference species resulting from the 16S rRNA gene sequence analysis are shown in FIG. 8. The alignment of all *Thermus* spec. partial 16S rRNA sequences is shown in FIGS. 7a and 7b. The pattern of the 16S rRNA dendrograms confirmed the results of the MLEE analysis in regard of association of the *Thermus* isolates with known *Thermus* species and the discovery of a new, independent genetic lineage. This new lineage comprising 5 separate isolates represents a new *Thermus* species. The new species was named *Thermus eggertssonii* in honor of Gudmundur Eggertsson. According to 16S rRNA sequencing, the isolates 2123 and 2789 that belong to this new *Thermus* species were most closely related to *T. brockianus* (strain YS38) and *T. igniterrae* (strain RF-4) giving 98.3% and 97.8% sequence similarity, respectively (see table 1). However, as seen from the MLEE results it was genetically distant from *T. brockianus* with different alleles at all loci. The isolate strain #2789 was chosen as the type strain of *Thermus eggertssonii* (*Thermus eggertssonii* IT-2789).

TABLE 1

Thermus 16S rRNA sequence homologies

|  | T. spec. strain #284 (*T. eggertssonii*) | T. spec. strain #2123 (*T. eggertssonii*) | T. spec. strain #2789 (*T. eggertssonii*) |
|---|---|---|---|
| T. flavus | 94.6% | 95.7% | 95.7% |
| T. aquaticus | 94.8% | 96.0% | 96.0% |
| T. filiformis | 92.0% | 93.1% | 93.1% |
| T. thermophilus | 94.6% | 95.7% | 95.7% |
| T. igniterrae | 97.6% | 98.8% | 98.8% |

TABLE 1-continued

Thermus 16S rRNA sequence homologies

|  | T. spec. strain #284 (*T. eggertssonii*) | T. spec. strain #2123 (*T. eggertssonii*) | T. spec. strain #2789 (*T. eggertssonii*) |
|---|---|---|---|
| T. brockianus | 97.6% | 98.8% | 98.8% |
| T. antranikianus | 95.0% | 96.2% | 96.2% |
| T. scotoductus | 94.8% | 96.0% | 96.0% |
| T. oshimai | 89.6% | 90.8% | 90.8% |

Example Two

Cloning of Partial polA Gene Sequences from *T. eggertssonii* and its Closest Relative *T. brockianus* and Alignment with Partial polA Gene Sequences of *Thermus* Reference Species Family-I DNA polymerases, also called Pol A, as suggested by Braithwaite and Ito (Braithwaite et al., Compilation, Alignment, and Phylogentic Relationships of DNA Polymerases. Nucleic Acids Res. 21 (1993) 787-802. hereby incorporated by reference) contain conserved sequence motifs forming the active site of these polymerases. These motifs contain highly conserved sequence blocks often referred to as blocks A, B and C (Joyce et al., Function and Structure Relationships in DNA Polymerases. Annu. Rev. Biochem. 63 (1994) 777-822., hereby incorporated by reference) Alignments with a number of family A DNA polymerases from *Thermus* species were done by using the conserved blocks A and C. Invariable amino acid residues in these motifs allowed the deduction degenerate primers from known *Thermus* polymerase I coding sequences: A-forw: 5'-GCCGCCGACTACTCCCARAT HGGART-3' (SEQ ID NO: 36) and C-rev: 3'-CANGTRCTRCTCTACCA-CAAGCTCCCG-5 (SEQ ID NO: 37).

The degenerate CODEHOP primers Rose et al., Concensus-degenierte Hybrid Oligonulceotide Primers for Amplification of Distantly Related Sequences. nucleic Acids Res. 26 (1998) 1620-1635, hereby incorporated by reference) made it possible to amplify a 600 bp long core fragment of the DNA polymerase I gene (polA) from various *T. eggertssonii* strains and one *T. brockianus* isolate (strain #140). This gene fragment covers the coding region between the active site motifs A and C comprising the most conservative region of type I DNA polymerases.

Resulting PCR products were separated on 1% TAE gels and bands of approximately 600 bases excised from the gel and purified by using GFX, PCR DNA and Gel Band Purification kit (GE Healthcare) according the manufacturer. Five μl of the purified PCR products were used to clone the 600 bp PCR-generated fragments into the TOPA-TA vector (TOPO TA Cloning Kit, Invitrogen). Conditions for DNA ligation, competent cell transformation and colony plating and growth were applied as stated in the manufacturer's instructions. Several colonies from each cloning experiment were picked to isolate their plasmid DNA for sequencing using standard laboratory procedures for small-scale plasmid DNA purifications (Manuatis et al., as referenced herein). Cycle sequencing reaction was performed by using BigDye Terminator Cycle Sequencing Ready Reaction kit according to the manufacturer (PE Applied Biosystems) using the M13 forward and reverse primers.

The resulting DNA sequences of the polA gene core fragment from *T. eggertssonii* and *brockianus* were translated into amino acid sequenes using the VectorNTI software package (Invitrogen, Carlsbad). These amino acid sequences of the polA core region are referenced herein as SEQ ID NO: 18 to 23 and SEQ ID NO: 17, respectively.

Using the Clustal W algorithm of the Vector NTI software package, the *T. eggertssonii* and *brockianus* partial polA sequences were aligned to the corresponding sequence region from the DNA polymerase I of *T. aquaticus* (SEQ ID NO: 16), *T. thermophilus* (SEQ ID NO: 15), *T. flavus* (SEQ ID NO: 13), and *T. filiformis* (SEQ ID NO: 14). The alignment of all partial *Thermus* spec. polA amino acid sequences is shown in FIG. 9.

Table 2 shows the results of the sequence diversity analysis on the conserved polA core region of *Thermus* spec. DNA polymerases. There is significant sequence diversity between *T. eggertssonii* and the polA region of other *Thermus* species even in the most conserved polA region. This result indicates that *T. eggertssonii* encodes a unique, novel member (Teg DNA Pol I) of the *Thermus* genus DNA polymerase I family. The polA sequence of *T. brockianus* is the sequence most closely related to Teg DNA Pol 1, as it was the case for the 16S rRNA sequences and the MLEE ETs.

TABLE 2

Amino acid sequence diversity within the conserved polA core region among *Thermus* species in regard to the polA sequence from *T. eggertssonii*

|  | *T. flavus* | *T. aquaticus* | *T. filiformis* | *T. thermophilus* | *T. brockianus* |
|---|---|---|---|---|---|
| *T. eggertssonii* strain #284 | 7.8% | 9.6% | 18.8% | 9.0% | 2.4% |

Further, partial polA sequences from five *T. eggertssonii* strains were aligned against themselves in order to determine the intra-species diversity of polA core region and compare it against the inter-species diversity of polA sequence with the closed relative *T. brockianus* (see table 3).

TABLE 3

Intra-species amino acid sequence diversity within the conserved polA core region among five *T. eggertssonii* strains versus inter-species diversity with polA sequence from *T. brockianus*

|  | strain #2123 (Teg) | strain #2124 (Teg) | strain #2789 (Teg) | strain #2795 (Teg) | strain #140 (Tbr) |
|---|---|---|---|---|---|
| strain #284 (Teg) | 0.0% | 0.0% | 0.6% | 0.6% | 2.4% |

The results in table 3 show that the average polA sequence diversity among five *T. eggertssonii* strains is 0.3%+/−0.36%. That is less than 1 amino acid substitution (0.6% diversity) per 166 residues of the polA core sequence.

When the five individual polA sequences of *T. eggertssonii* strains are aligned against the sequence of their closest species relative—*T. brockianus*, the interspecies diversity within the polA core sequence averages at 2.75%, e.g. 4 to 5 amino acid substitutions within a sequence of 166 residues (see table 5). The average polA inter-species sequence diversity between *T. eggertssonii* and *T. brockianus* is approximately 7 times higher than the intra-species diversity among different *T. eggertssonii* strains from genetically distinct geographic populations. confirming that the DNA polymerase I encoded by *T. eggertssonii* is different polymerase than the analogous enzyme of its closest relative *T. brockianus*.

TABLE 5

Inter-species amino acid sequence diversity within the conserved polA core region between five *T. eggertssonii* strains and the polA sequence from *T. brockianus*

|  | strain #2123 (Teg) | strain #2124 (Teg) | strain #2789 (Teg) | strain #2795 (Teg) | strain #284 (Teg) |
|---|---|---|---|---|---|
| strain #140 *T. brockinaus* | 2.4% | 3.0% | 3.0% | 3.0% | 2.4% |

Example Three

Cloning of the Complete polA Gene Sequence from *T. eggertssonii* and Alignment with polA Gene Sequences of *Thermus* Reference Species The nucleotide sequence of the 600 bp polA gene fragment from *T. eggertssonii* strain #248 was used to clone the complete coding sequence of the Teg DNA polymerase I employing a PCR-based gene walking technique called GENEMINING™. This method applies two sets of primers to amplify the unknown sequence downstream of the 3'-terminus of the known sequence and upstream of the 5'-terminus of the known sequence, respectively. Each of the two primer sets comprises a gene specific primer deducted from the known polA sequence and an opposing primer with an arbitrary 3'-terminal sequence. A third primer is added to both sets, which is comprises the sequence of the 5'-terminal half of the arbitrary primer. This sequence also contains two unique restriction sites to facilitate cloning of the PCR products. In the primer set for amplification of the 3'-terminal unknown polA sequence the gene-specific primer was the forward oriented primer. In the set for amplification of the unknown 5'-terminal polA the gene-specific primer was the reverse primer. The following three arbitrary primers were used:

```
                                        (SEQ ID NO: 38)
Arb1:  5'-GGCCACGCGTCGACTAGTACNNNNNNNNNNNGATAT-3', (SEQ ID NO: 39)
Arb.2: 5'-GGCCACGCGTCGACTAGTACNNNNNNNNNNACGCC-3', (SEQ ID NO: 40)
Arb.3: 5'-GGCCACGCGTCGACTAGTAC-3'.
```

Each PCR was performed in two rounds according to a previously described arbitrary primer PCR method (Caetano-Anolles, Scanning of Nucleic Acids by In Vivo Amplification: New Developments and Applications. Nat. Biotechnol. 14 (1996) 1668-1674, hereby incorporated by reference). In the first round (up to 10 cycles) at a low annealing temperature, either arbitrary primers 1 and 2 were incorporated into a population of PCR fragments, wherever the found an appropriate target sequence opposite of the gene-specific primer. In the second round at higher annealing temperatures, discrete PCR products were amplified out of the arbitrary mixture. These PCR products had incorporated either one of the arbitrary primer 1 or 2 at one end and the gene-specific primer at the opposing end.

Figure 13:
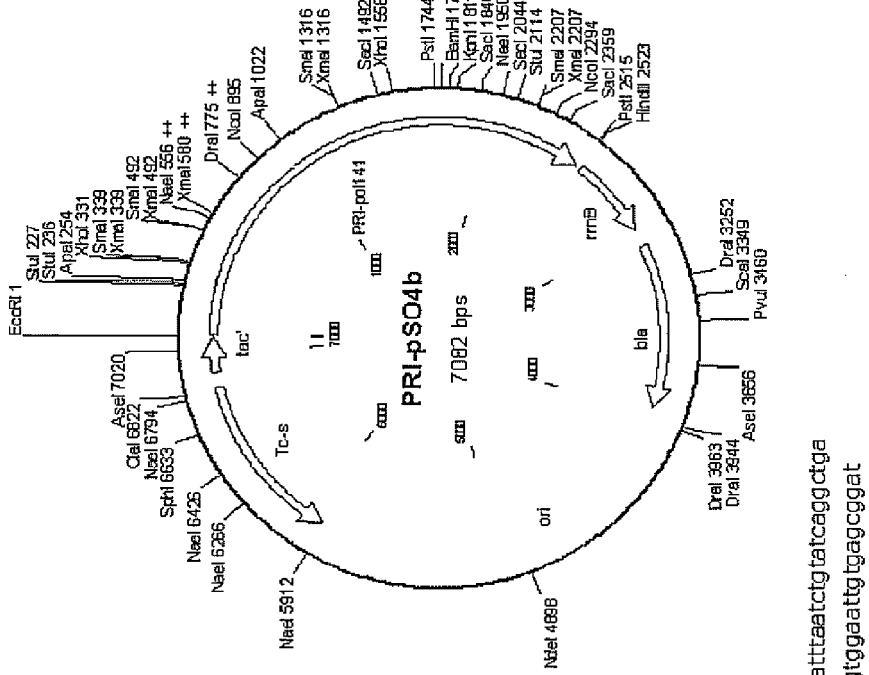
FIG. 13 provides the physical map of the expression vector PRI-pSO4 encoding the full-length polA gene from *Thermus eggertssonii*.

The PCR products obtained were then purified, cloned and sequenced as described earlier. By a series of subsequent PCR rounds using nested primer sets specific for internal sequence fragments determined in the previous round, the less conserved flanking regions of the polA gene were obtained. After the complete coding sequence of the polA gene was obtained, gene-specific primers for the extreme 5'- and 3'-termini of the coding sequence were designed. This primer set was then used to amplify the complete Teg DNA Pol I gene as one fragment. The 5'-terminal forward primer had included a unique EcoRI restriction site. The 3'-terminal forward primer had included a unique Bgl II restriction site. The full length polA PCR product was cloned into pBTac-1 expression vector (Boehringer Mannheim, Pensberg) using the unique restriction sites EcoR-I and Bam HI of the vector to accommodate the EcoRI/Bgl II fragment carrying the polA gene. The physical map of the resulting Teg DNA polymerase expression vector—PRI-pSO4—is shown in FIG. 13. It is well known to people skilled in the aft that expression vector plasmids may be used, which comprise a different type of antibiotic resistance marker gene, promoter sequence and origin of replication compared to the vector pBTAC-1 chosen.

Example Four

Figure 11A:
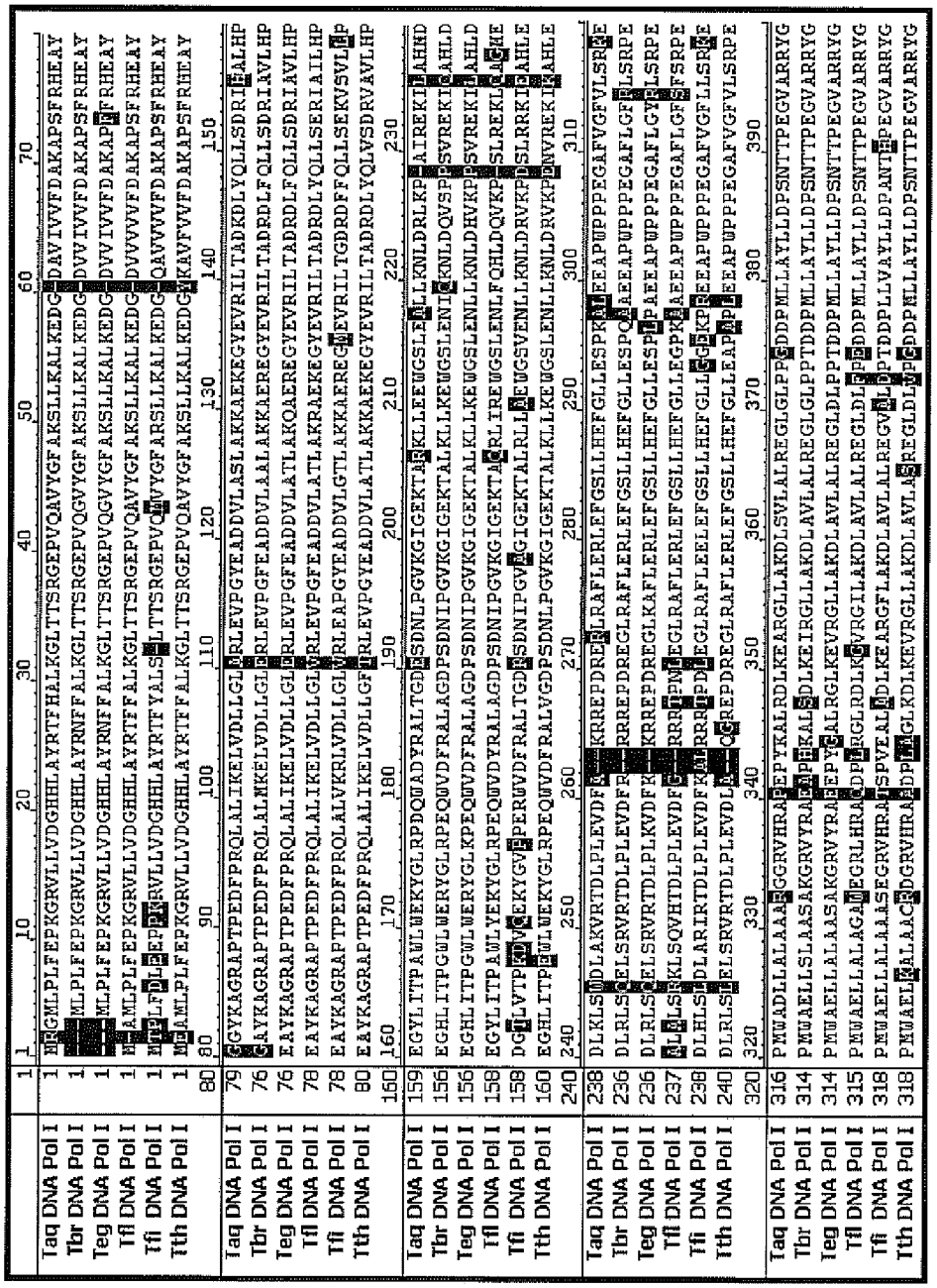
Figure 11B:
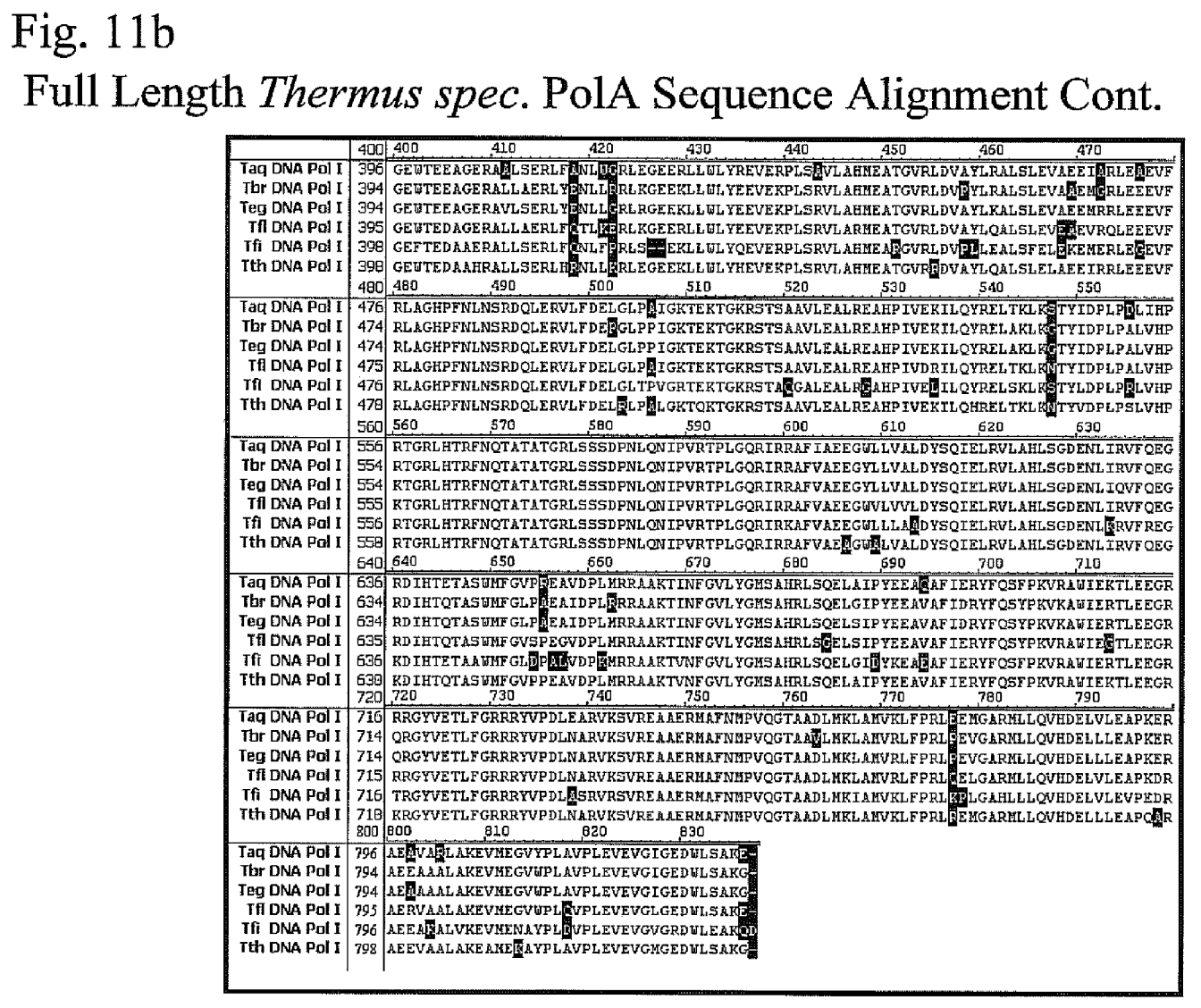
Figure 12:
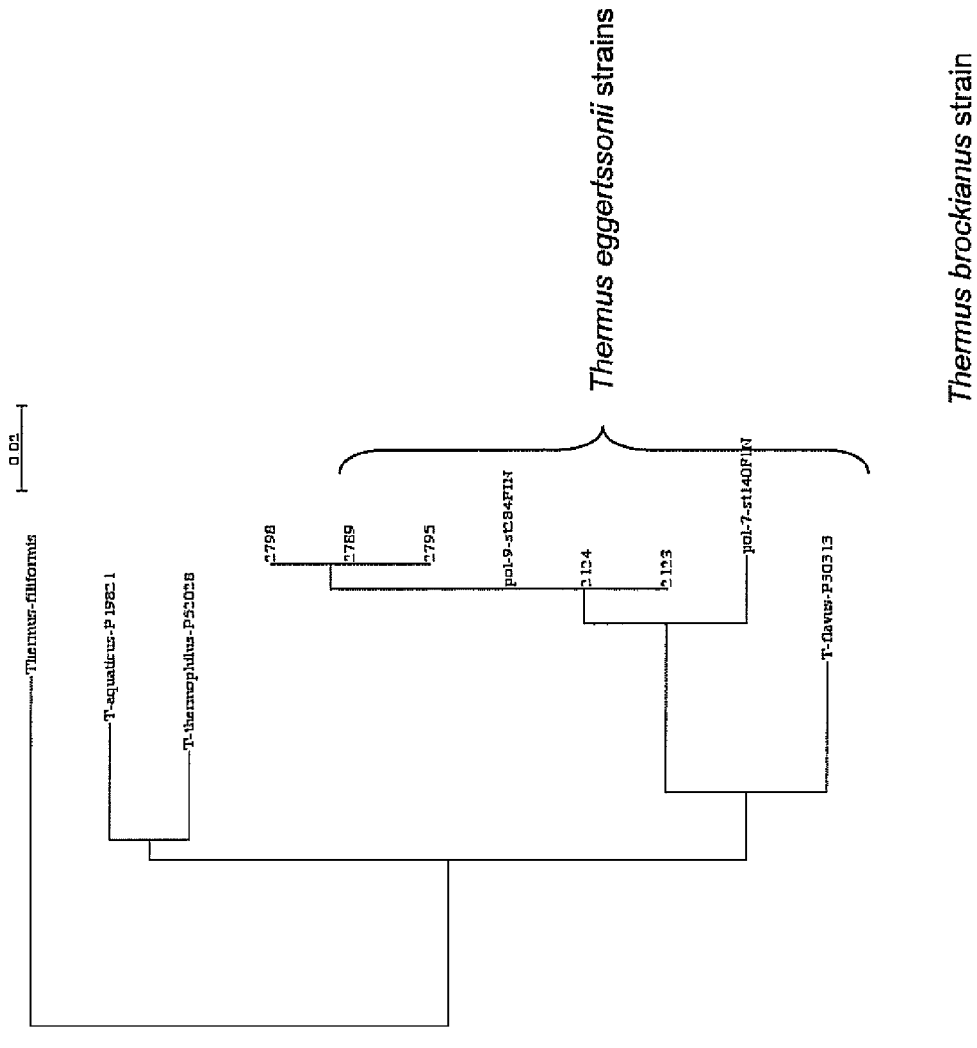
FIG. 12 provides a phylogenetic dendrogram calculated based on the amino acid sequence alignments from FIG. 11.

Alignment of the Complete polA Sequence from *T. eggertssonii* with polA Sequences of *Thermus* Reference Species The nucleotide and amino acids sequences of full length Teg, Tbr, Taq and Tth DNA polymerase were aligned using the Clustal W algorithm of the software package VectorNTI (Invitrogen, Carslbad). The results of the alignment are summarized in Table 6 for DNA sequence alignment and Table 7 for amino acid sequence alignment. The complete amino acid sequence alignments are shown in FIGS. 11a & 11b, and the corresponding phylogenetic tree is shown in FIG. 12.

TABLE 6

DNA sequence homologies of *Thermus* spec. Type I DNA polymerases

|  | Teg DNA Pol I | Tbr DNA Pol I | Taq DNA Pol I | Tth DNA Pol I |
| --- | --- | --- | --- | --- |
| Teg DNA Pol I |  | 94% | 84% | 84% |
| Tbr DNA Pol I |  |  | 84% | 84% |
| Taq DNA Pol I |  |  |  | 85% |
| Tth DNA Pol I |  |  |  |  |

TABLE 7

Amino acid sequence homologies of *Thermus* spec. Type I DNA polymerases

|  | Teg DNA Pol I | Tbr DNA Pol I | Taq DNA Pol I | Tth DNA Pol I | Tfi DNA Pol I | Tfl DNA Pol I |
| --- | --- | --- | --- | --- | --- | --- |
| Teg DNA Pol I |  | 95% | 87% | 87% | 78% | 87% |
| Tbr DNA Pol I |  |  | 86% | 86% | 78% | 86% |
| Taq DNA Pol I |  |  |  | 87% | 78% | 86% |
| Tth DNA Pol I |  |  |  |  | 79% | 86% |
| Tfi DNA Pol I |  |  |  |  |  | 77% |
| Tfl DNA Pol I |  |  |  |  |  |  |

The majority of the amino acid variations in the Teg DNA Pol I sequence reside in the N-terminal 5'-3'-exonuclease domain. Within the polymerase, a number of non-conservative amino acid substitutions are noticeable in regions known to be involved in DNA substrate binding, processivity and primer extension. As already established previously, the highest degree of sequence homology Teg DNA polymerase shares with the Tbr DNA polymerase, although at a lower level (95%) over the complete polA sequence than just in the conserved polymerase core region. There is no significant difference between the sequence homologies on the DNA versus the amino acid level. The Teg, Tbr and Tth DNA polymerases show almost the exact same sequence diversity (13-14%), when aligned pair wise against the sequence of Taq DNA polymerase. The observed degree of sequence diversity of the complete Teg DNA polymerase in regard to known DNA polymerase of other *Thermus* species establishes the Teg DNA polymerase s a novel, unique member of the *Thermus* DNA polymerase I family.

Example Five

Expression of Teg DNA Polymerase I

The PRI-pSO4 vector for the expression of Teg DNA polymerase just exemplifies one type of expression vector plasmid that one can use to express Teg DNA polymerase in *E. coli*. People skilled in the art are familiar with a large variety of expression vector plasmids suitable for expression of Teg DNA polymerase in *E. coli*, as well as in other host organisms such as the yeast fingi *Pichia pastoris, Saccharomyces cervisiae* or *Klyveromyces lactis*. Another possible choice for expressions hosts to people skilled in the art, are imortilized mamalian and insect cell lines. The choice of a particular expression vector is restricted and pre-determined by the host organism and its genetic background.

Ten ng of purified PRI-pSO4 expression vector plasmid was used to transform competent cells of the *E. coli* expression cell line Rosettagami (DE3)pLysS (Novagen, Madison). This *E. coli* strain is genetically optimized for the expression of heterologous proteins, which coding sequences bare rare codons not matched by indigenous *E. coli* tRNA molecules. The transformation kit containing competent cells of die Rosettagami (DE3)pLysS *E. coli* strain were purchased from Novagen. The transformation procedure, cell growth, plating and selection of recombinant clones were carried out according to manufacture's instructions. Single colonies of a diameter of 2-3 mm were selected after 24 hours incubation at 37° C. on 2xYT-Agar plates (TechNova) containing 100 μ/ml ampicillin.

The expression of Teg DNA polymerase on the PRI-pSO4 vector plasmid is driven by a hybrid TAC promoter comprising regulatory sequence elements of promoters from the *E. coli* genes for tryptophane synthetase and β-lactamase. The gene's transcription from this promoter is induced by the presence of the effector molecule IPTG. I mM IPTG concentration in the liquid growth media 2xYT (TechNova) was used to induce Teg DNA polymerase expression from the PRI-pSO4 vector. It is a well known fact for people skilled in the art that other effector molecules, such as rhamnose or arabinose, or other concentrations of IPTG may be applied depending on the exact promoter and expression vector construct used. Empirical optimization of the effector molecule concentration in the growth media is necessary to achieve optimal expression levels of Teg DNA polymerase with other expression constructs. The same rule applies for people skilled in the art to the composition of the growths media used. It is also well known to the people skilled in the art that the choice and the concentration of the antibiotic applied for selection of cells carrying the expression vector plasmid. Depending on the exact nature of the vector plasmid used other antibiotics, such as tetracycline, kanamycine or chloramphenicol may be used.

Figure 14:
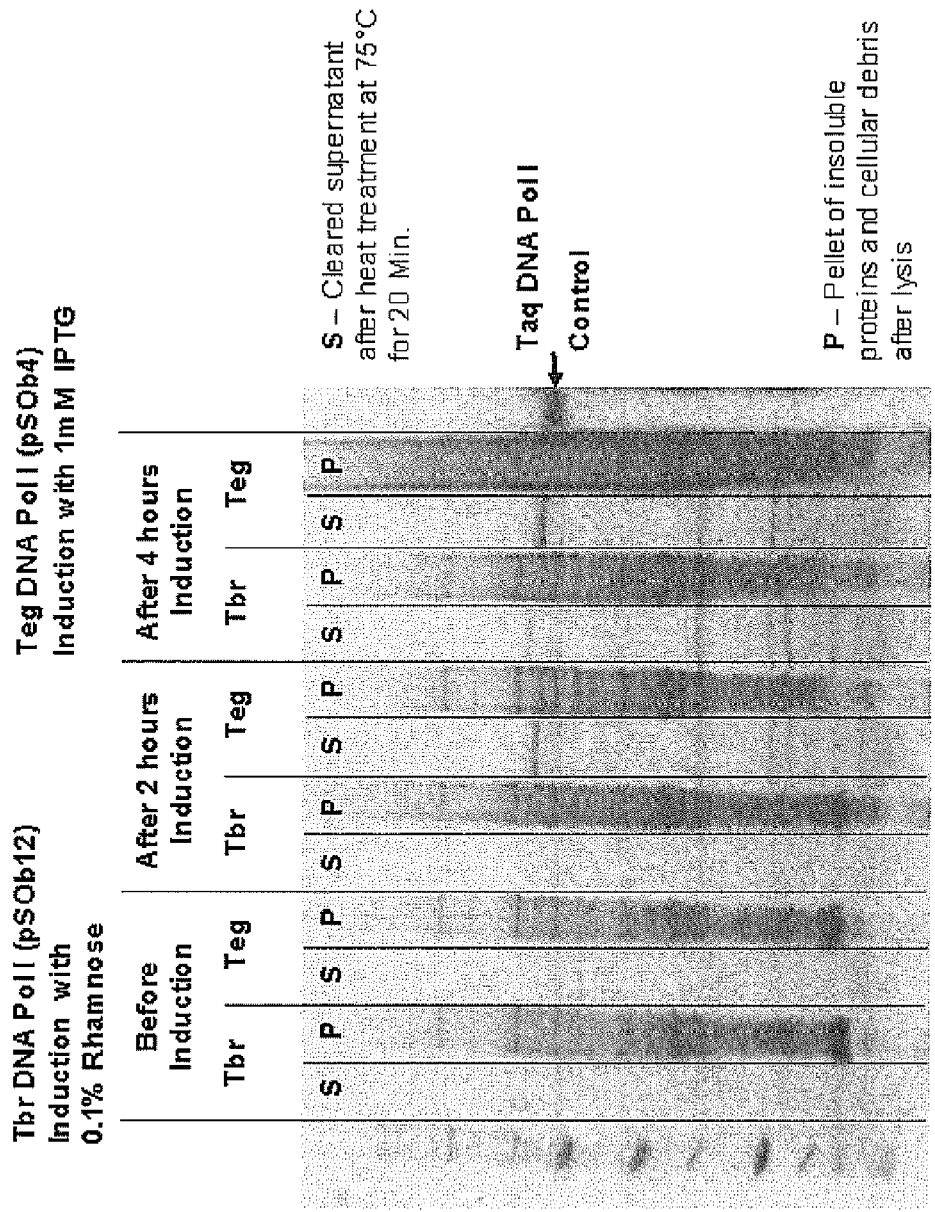
FIG. 14 provides an electrophoregram showing the induction of Teg DNA polymerase expression as a soluble protein over a time course of 4 hours.
Figure 15:
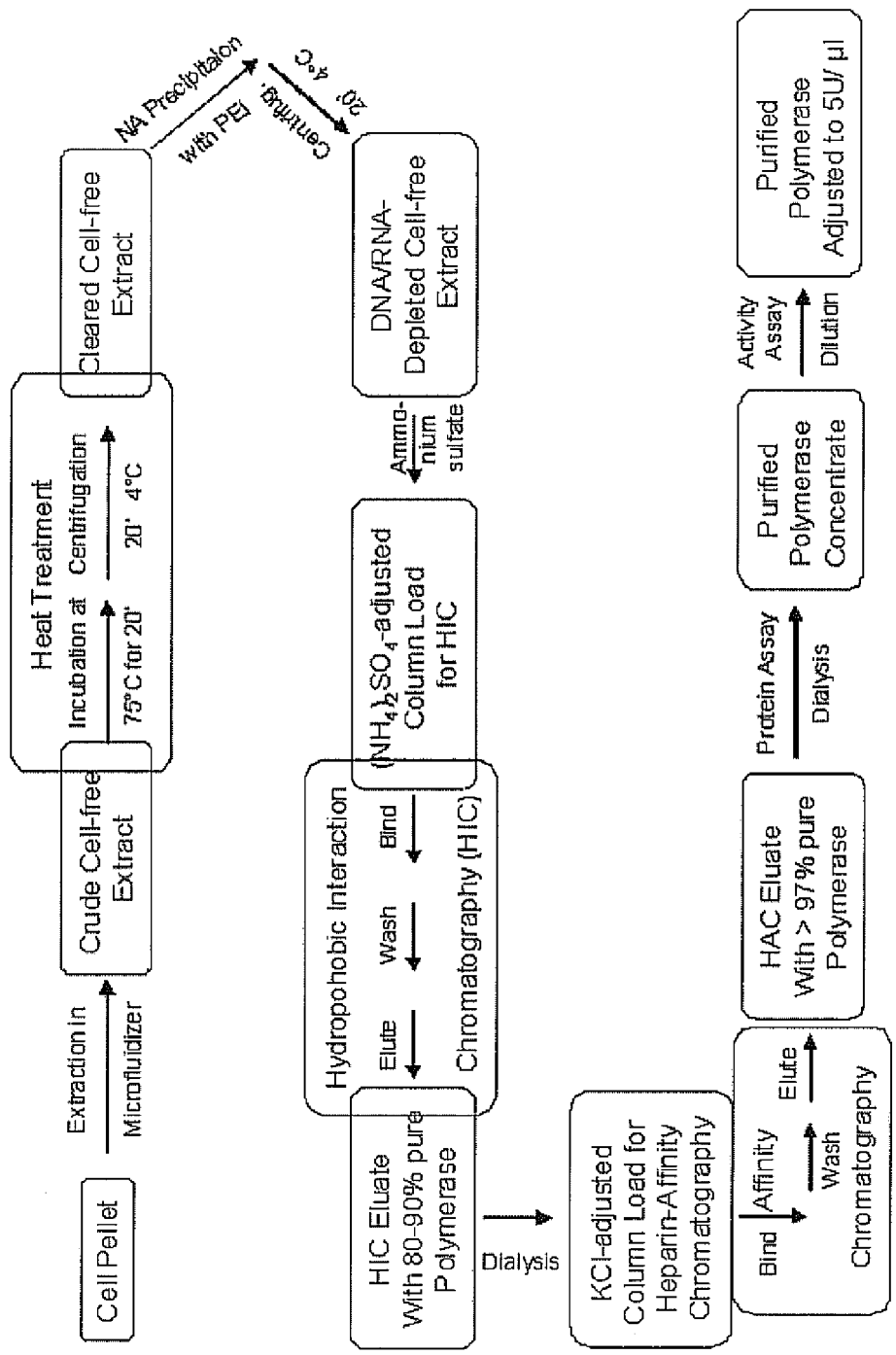
FIG. 15 provides the schematics of the large-scale purification process for the recombinant DNA polymerase I.

The incubation time after the effector molecule (IPTG) is added to turn on the expression of the polymerase, e.g. induction time, is another parameter in need of empirical optimization. For that purpose, three Erlenmeyer flasks containing 50 ml 2xYT media with 100 μg/ml ampicillin were inoculated each with a single colony of PRI-pSO4/RosettaGami-pLysS cells. The 50 ml cultures were incubated on a shaker at 37° C. and 250 rpm until the *E. coli* cultures reached density of $OD_{600}$ 0.7 to 0.8. At this point in time one ml samples of all liquid cultures were taken and IPTG was added to two of the three liquid cultures to a final concentration of 1 mM. Cells in the culture samples were harvested by centrifugation and frozen at −20° C. until further processing. Incubation of the remaining cultures was continued under conditions as described above. After 2 hours the cells of the first culture induced with IPTG were harvested by centrifugation and stored frozen at −20° C. After 6 hours the cells of the second IPTG-induced culture were harvested. The calls from all culture samples were lysed in 10 mM Tris-HCl pH 8.0, 10 mM EDTA, X mM PMSF containing 10 μg/ml lysozyme for 30 minutes at 37° C. After lysis, the crude lysate was separated into a insoluble fraction (pellet) and soluble protein fraction (supernatant) by high speed centrifugation (20000 g, 20 minutes). Aliquotes of both fractions from culture sample were mixed with one sample volume of SDS-Gel Loading Buffer (Biorad), heated for 5 minutes at 95° C. and then loaded onto to a Criterion SDS-polyacrylamide gel (Criterion Tris-HCl gel 4-20% gradient, Biorad). Electrophoretic separation of the protein fractions and Coomassie staining of the separated proteins were carried out exactly according to manufacturer's instructions. Purified Taq DNA polymerase (2 μg) was loaded on the gel as electrophoretic mobility maker to facilitate the detection of the Teg DNA polymerase protein band in the crude protein fraction. The electrophoregram of the induction time experiment are shown in FIG. 14. No polymerase was expressed in the *E. coli* cells of the culture without IPTG induction. Already after two hours of induction with 1 mM IPTG a Teg DNA polymerase band of the correct size is detectable in the soluble protein fraction. The amount of Teg DNA polymerase in the soluble cell fraction continues to rise till 4 hours after induction. No Teg DNA polymerase band was datable in the insoluble cellular fraction at any time. Further experiments (data not shown) established that after 6 hours of induction the amount of expressed Teg DNA polymerase in the soluble cellular fraction saturated. Further incubation up to 12 hours neither increase nor decrease the amount of soluble Teg DNA polymerase in the RosettaGami cells. Six hours induction time at 37° C. was then used for all further experiments.

To produce biomass for large-scale purification of Teg DNA polymerase a 100 ml (2xYT medium containing 100 μg/ml ampicillin) pre-culture in a 250 ml flask was inoculated with a single colony of PRI-pSO4/RosettaGami cells The culture was incubated at 250 rpm and 37° C. on a shaker for 16 hours overnight. The following morning four 2.8 liter Erlenmeyer flaks containing each 1 liter 2xYT medium with 100 mg/ml ampicillin each (adjusted to 37° C.) were inoculated with 1 ml of the pre-culture each. These 1 L cultures were grown at 37° C. and 250 rpm until they reached a density of $OD_{600}$ 0.6 to 0.8. At this point IPTG was added to the final concentration of 1 mM. After induction Incubation was continued under identical conditions for another 6 hours. After that the culture flasks were transferred on ice. Cells of all culture flasks were harvested by centrifugation in 500 ml bottles at 5000 rpm for 30 minutes. Table 8 summarizes the data from biomass production.

TABLE 8

Data from biomass production for large-scale purification of Teg DNA polymerase I

| | Teg DNA Pol I |
|---|---|
| Culture Volume | 4 × 1 L in 2.8 L Flasks |
| Media | 2YT + 100 μg/ml amp |
| Growths Conditions | 37° C./250 rpm |
| Induction | 1 mM IPTG |
| Conditions | at $OD_{600}$ = 0.7-0.8 |
| Induction Time | 6 h |
| Final Cell Density | $OD_{600}$ = 3.2 |
| Harvested Biomass | 23.7 g |
| Yield | 5.92 g/L |

Example Six

Large-Scale Purification of Teg DNA Polymerases

Figure 10:
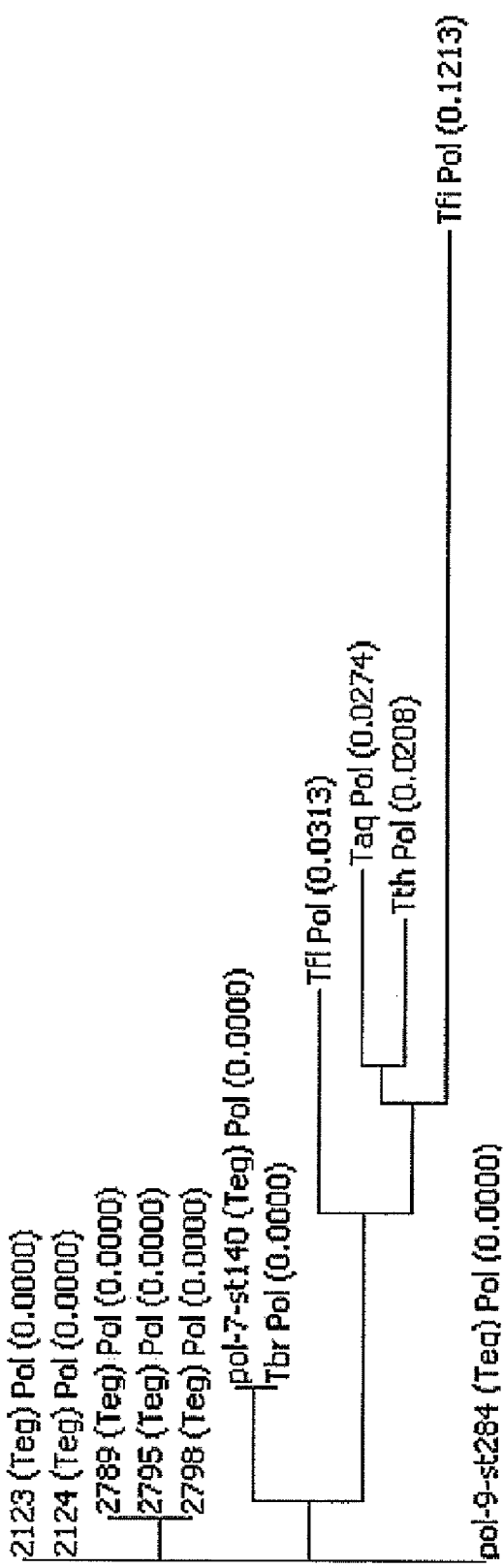
FIG. 10 provides a phylogenetic dendrogram calculated based on the conserved region alignment from FIG. 9.

The general purification procedure to purify Teg DNA polymerase is outlined in FIG. 10. The method utilizes four major purification steps. First, the crude cell extract is incubated at 75° C. to denature and remove non-thermostable *E. coli* host proteins. Second, the total nucleic fraction is depleted from the heat-treated cell extract by precipitation with polyethyleneimine (PEI). Third, the cleared supernatant is fractionated by ammonium sulfate precipitation. The fourth step comprises hydrophobic interaction chromatography on Butyl-Sepharose and the final step comprises ligand-affinity chromatography on Heparin-Sepharose.

For protein extraction, 20 g of wet cell biomass produced in the previous step was re-suspended in 200 ml Cell Extraction Buffer comprising 50 mM Tris-HCl pH 8.0, 10 mM EDTA, 1 mM DTT and 0.1% PMSF. The crude cells suspension was homogenized utilizing an ultrasonic mixer at low settings (2-3) (IKA T18) for 1 to 2 minutes. After homogenization the cell suspension was chilled on ice for 10 to 15 minutes to adjust to 4-8° C.

Next, the cells were ruptured in a microfluidizer by forcing the chilled suspension through a micro capillary at an inlet pressure of 15 kPsi. This step was carried out two more times at a higher inlet pressure of 30 kPsi. Between each passage the crude cell extract was chilled on ice. The efficiency of cell rupture was monitored after each step under a phase-contrast microscope equipped with a 100× magnifying lens. Normally, after three passages through the microfluidizer capillary >90% of all cells are lysed. The final cell extract was chilled on ice for 10 minutes to reach 4° C.

For heat treatment the crude cell extract was carefully transferred in to 100 ml polypropylene (PP) bags, which were then heat-sealed. Care was taken to trap a minimal amount of air in the sealed PP bags. The sealed PP bags were submersed into a waterbath adjusted to 75° C. and incubated for 20 minutes turning then bags every 4 to 5 minutes. After 20 minutes the PP bags containing the crude cell extract were chilled in ice for 10 minutes. Then, the denatured protein fraction was removed from the cell extract by centrifugation at 20000 g (12000 rpm) for 40 minutes at 4° C.

In the next step, the nucleic acid fraction was depleted from the cleared cell extract supernatant with polyethyleneimine (PEI). On ice, over a time course of 5 minutes under continuous gentle mixing, a concentrated PEI solution (10%) was added dropwise until its final concentration in the cell extract reached 0.1%. The cell extract containing PEI was further incubated under continuous gentle mixing for 20 minutes on ice. After 20 minutes, the nucleic acid precipitate was separated from the crude cell extract by centrifugation at 20000 g (12000 rpm) for 40 minutes at 4° C., After centrifugation, the ionic strength of the cleared, post-PEI supernatant was adjusted to prepare the cell extract for chromatographic separation the Butyl-Sepharose. Over a time course of 10 minutes ammonium sulfate powder was added in small portions under continuous gentle mixing till the saturation reached 27.5% (16 g ammonium sulfate per 100 ml cell extract). In order to separate the protein fraction, which precipitates at 27.5% ammonium sulfate saturation, the cell extract was incubated overnight at 4-8° C. for 16 hours and then centrifuged the next day at 20000 g (12000 rpm) for 40 minutes at 4° C. The Teg DNA polymerase remains soluble in the supernatant fraction.

Next, the conductivity of the cleared cell extract was adjusted within 5-10 mS of the conductivity of the Butyl-Sepharose-Column-Equilibration Buffer by adding either small portions of ammonium sulfate powder or Butyl-Sepharose-Column-Equilibration Buffer. Before the loading the cleared cell extract onto the column, the cell extract was vacuum-filtered through a 0.45 µm sterile PES-filter device with a 500 ml receiver bottle (Millex GS-SteriCup, Millipore).

For the first celromatographic separation a Fast-Flow, high substitution Butyl-Sepharose (GE-Healthcare, Pharmacia) column with 2 cm bed diameter and 10 cm bed height was applied. This column was equilibrated in a buffer comprising 50 mM Tris-HCl pH 8.0, 1 mM EDTA, 1.21M ammonium sulfate (e.g. 27.5% saturation), and 1 mM DTT.

The cleared cell extract was loaded onto the column at constant flow rate of 10 ml/min. After that, the column was washed with 2 column volumes (CV) of the column equilibration buffer.

The Teg DNA polymerase-containing fractions were eluted from the Butyl-Sepharose column at a flow rate of 10 ml/min with a stepwise decreasing gradient of ammonium sulfate salt concentration. The salt gradient was formed by mixing various ratios of the Column Equilibration Buffer and Elution Buffer in a buffer gradient valve. In the first segment of the gradient spread over 0.5 CVs the ammonium sulfate concentration in the Elution buffer decreased from 1.21 M to 666 mM. In the second segment of the gradient elution continued at a constant concentration of 666 mM ammonium sulfate over 2 CVs. In the third gradient segment the ammonium sulfate concentration in the Elution Buffer dropped from 660 mM to zero spread over two CVs. Teg DNA polymerase elutes from the column in third segment of the gradient. Fractions were collected in 2 ml volume aliquotes.

Figure 16:
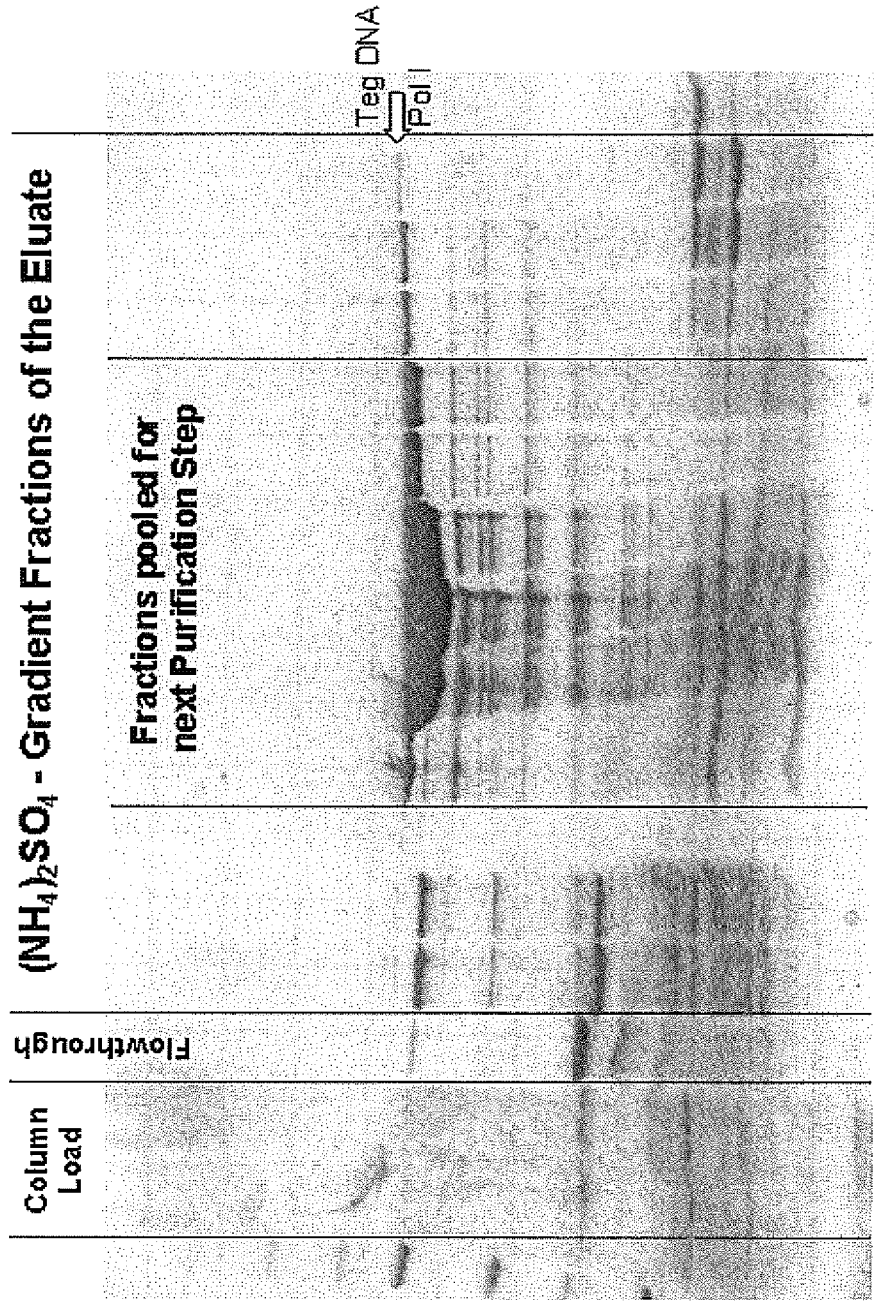
FIG. 16 provides SDS-PAGE gel analysis of purification of Teg DNA polymerase by hydrophobic interaction chromatography on butyl sepharose.

Samples from each eluted fraction (10 µl) were prepared for SDS-PAGE analysis on 4-20% Criterion gradient gels (Biorad) in order to determine the fractions containing the highest concentration of Teg DNA polymerase. Purified Taq DNA polymerase (2 µg) was loaded on the gel as a marker to identify the Teg DNA polymerase band of the right size. FIG. 16 examplifies an electrophoregram of the SDS-PAGE analysis of fractions eluted from the Butyl-Sepharose column.

Fractions containing the highest amount of Teg DNA polymerase were pooled. Next, the pooled Teg DNA polymerase fraction was dialyzed over 12 to 16 hours with two buffer changes against the Heparin Column Equilibration Buffer comprising 50 mM Tris-HCl pH 8.0, 50 mM KCl, 0.1 mM EDTA, 1 mM DTT. After dialysis the conductivity of the pooled Teg DNA polymerase fraction was adjusted to the conductivity of the column equilibration buffer. The adjusted Teg DNA polymerase pool was then loaded onto a Fast-Flow-Heparin-Sepharose column (bed height 20 cm; bed diameter 2 cm) at flow rate of 7 ml/min. After sample loading the column was washed with 2 CVs of Heparin-Sepharose-Equilibration Buffer.

The Teg DNA polymerase-containing fractions were eluted from the Heparin-Sepharose column at a flow rate of 7 ml/min with a linear increasing gradient of potassium chloride salt concentration. The potassium chloride gradient was formed by mixing various ratios of the Column Equilibration Buffer and Elution Buffer in a buffer gradient valve. The Heparin—Sepharose-Column-Elution Buffer comprises so mM Tris-HCl pH 8.0, 0.75 M KCl, 0.1 mM EDTA, 1 mM DYE. The elution gradient was run in one segment over 5 CVs ranging from 50 mM to 750 mM KCl. Eluted fractions were collected in 2 ml volumes. Teg DNA polymerase eluted at a potassium chloride concentration ranging between 0.6 and 0.75 M.

Figure 17:
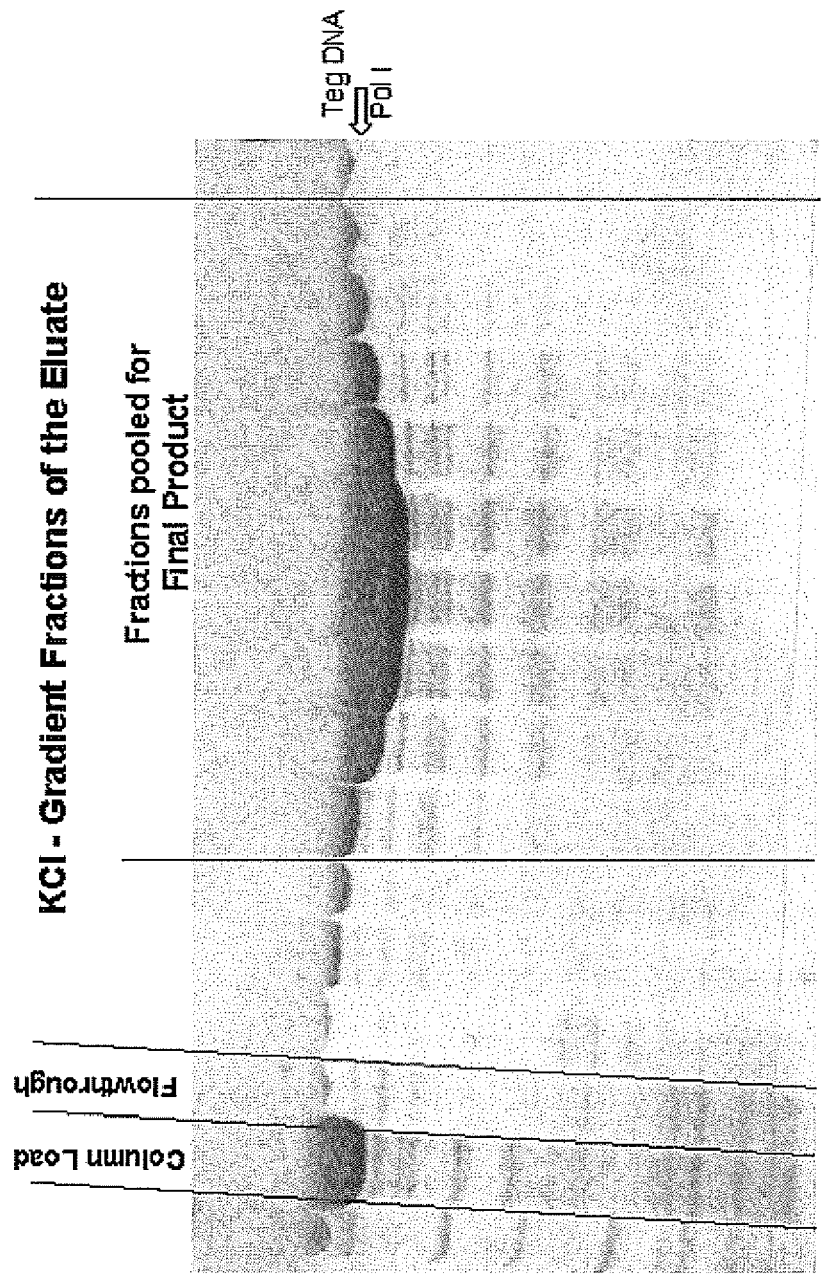
FIG. 17 provides SDS-PAGE analysis of purification of Teg DNA polymerase by ligand-affinity chromatography on heparin sepharose.

Samples from each fraction (10 µl) were prepared for SDS-PAGE analysis on 4-20% Criterion gradient gels (Biorad) in order to determine the fractions containing the highest concentration of Teg DNA polymerase. Purified Taq DNA polymerase (2 µg) was loaded on the gel as a marker to identify the Teg DNA polymerase band of the right size. FIG. 17 exemplifies an electrophoregram of the SDS-PAGE analysis of fractions eluted from the Heparin-Sepharose column.

The fractions containing the highest amount of Tog DNA polymerase were pooled and dialyzed against 2× storage without glycerol comprising 40 mM Tris-HCl pH 8.0, 0.2 mM EDTA, 2 mm DTT, 200 mM KCl, 1% Tween 20 (SIGMA), 1% IGEPAL-C630 (Sigma) over 48 hours with three buffer changes. The final, pooled and dialyzed Teg DNA polymerase fraction was sterile filtered (0.45 µm PES filter) and mixed with one fraction volume of sterile, nuclease-free 99% glycerol (SIGMA) to achieve the final storage buffer concentrations comprising 20 mM Tris-HCl pH 8.0, 100 KCl, 0.1 mM EDTA, 1 mM DTE, 0.5% Tween 20, 0.5% IGEPAL-C630

Figure 18:
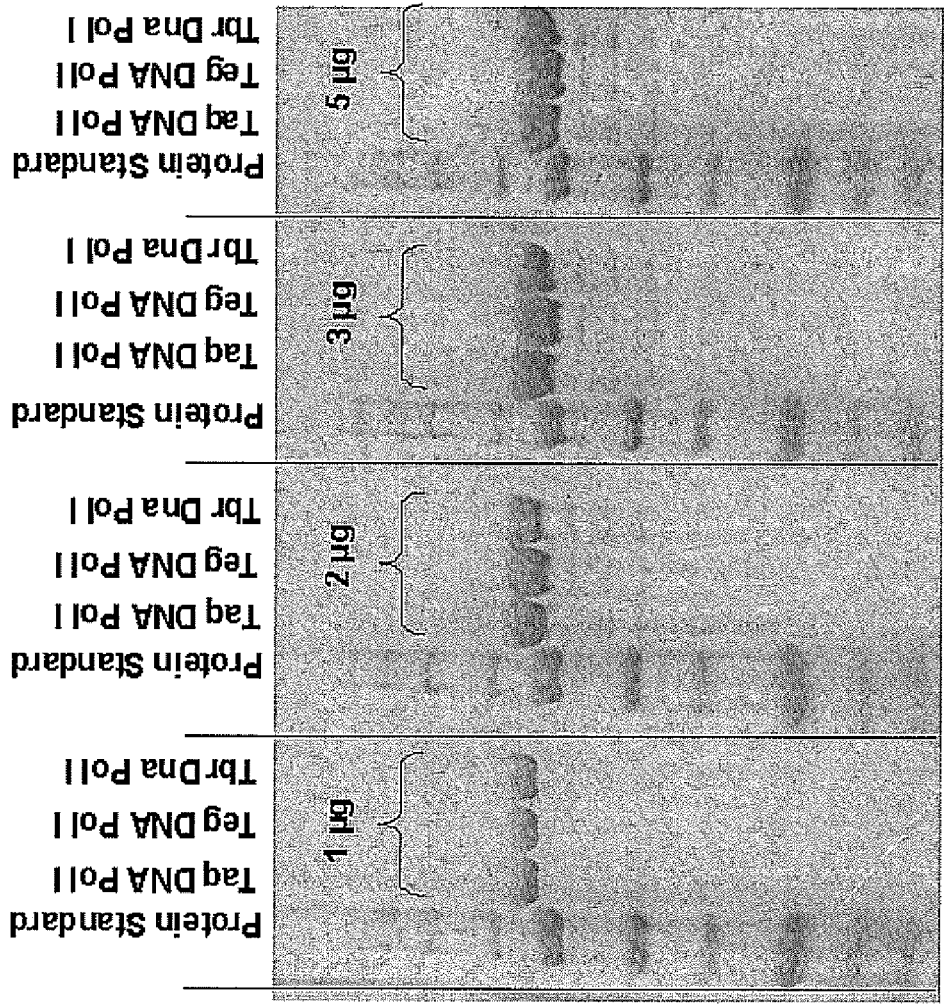
FIG. 18 provides SDS-PAGE gel analysis comparing the purified endproduct of Teg DNA polymerase isolation against purified recombinant Taq- and Thr DNA polymerase.

The protein concentration in the final purified Teg DNA polymerase was determined using a kit from Pierce according to manufacturer's instructions. FIG. 18 shows the electrophoregram of SDS-PAGE analysis of the purified recombinant Teg DNA polymerase in comparison with samples of purified recombinant Taq- and Tbr DNA polymerase. The Purity of the Teg DNA polymerase turned out >98% as measured by densitometric quantitative analysis of the Coomassie-stained protein bands in the Teg DNA polymerase gel sample. Table 9 summarizes the results of the large-scale purification of Teg DNA polymerase.

TABLE 9

| Purification summary | |
|---|---|
| | Teg DNA Pol I |
| Culture Volume | 4 L |
| Biomass | 23.7 g |
| Biomass Yield | 5.92 g/L (6 h induction) |
| Total Protein | 41.4 mg |
| Final Volume | 16 ml |
| Protein Concentration | 2.6 mg/ml |
| Protein Yield /Cells | 1.8 mg/g cells |
| Purity | >98% |

Example Seven

Determination of the Specific Activity and Activity Concentration of Purified Teg DNA Polymerase A non-radioactive, PCR-based activity assay, developed to determine the activity of Taq DNA polymerase, was used. The assay is based on the end-point quantification of a 350 bp PCR product (fragment of human beta actin gene) amplified using human genomic DNA as the template. The amounts of all reactants (250 µmol of each dNTP, 50 ng template DNA, 40 µmol primers, and 2.0 mM magnesium ions), except the DNA polymerase, are provided in excess, so that the amount of active DNA polymerase is the only limiting factor of the product yield. The time for the primer extension and annealing at each cycle was set to an absolute minimum of 8 seconds each. The total number of cycles was set to 30, where the phase of exponential amplification is turning over into the stage of product saturation. Under these conditions, the end point amount of PCR product is a linear function of the input amount of DNA polymerase within the range of 0.2 U-0.8 U per 50 µl reaction. A lot of commercial Taq DNA polymerase (Roche Molecular Diagnostica; GMP-Taq), which had been adjusted by the manufacturer to 5 U/ml in a radioactive primer extension assay, served as the enzyme calibrator in the assay.

Starting from the concentrated stock of purified Teg DNA polymerase a series of enzyme dilutions was prepared in the polymerase storage buffer as outlined in Table 10. The known protein concentrations of Teg DNA polymerase in regard to Taq DNA polymerase was used as a guide to determine the right range of dilutions to include the target concentration of 5U/µl.

TABLE 10

Dilutions prepared from the concentrated stock of Teg DNA polymerase I
Teg DNA Polymerase

| | Dilution Factor | | | | | | | |
|---|---|---|---|---|---|---|---|---|
| | 1:10 | 1:15 | 1:20 | 1:25 | 1:30 | 1:35 | 1:40 | 1:50 |
| Concentrated Polymerase Stock (µl) | 20 | 20 | 20 | 20 | 20 | 20 | 20 | 20 |
| Volume Storage Buffer (µl) | 180 | 280 | 380 | 480 | 580 | 680 | 780 | 880 |
| Total Volume (µl) | 200 | 300 | 400 | 500 | 600 | 700 | 800 | 900 |
| Protein conc. in ng/µl | 260 | 173 | 130 | 104 | 86 | 74 | 65 | 52 |

Figure 19:
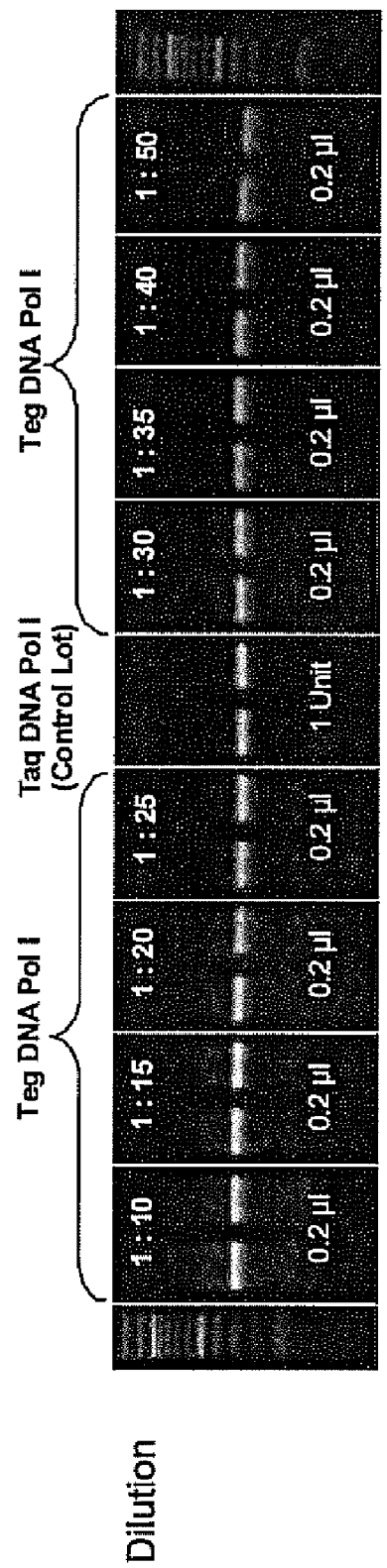
FIG. 19 provides agarose gel analysis of first-step enzyme dilution of Teg in the Beta-actin PCR activity assay.

The complete activity assay was carried out in three consecutive rounds of PCR experiments to narrow in the range of enzyme dilutions to be close to the target concentration 5U/µl. In the first PCR round, 0.2 µl of each Teg DNA polymerase dilution per 50 µl reaction were compared in two replicates against 0.2 µl (e.g. I U) of the Taq DNA polymerase. The reaction set-up is shown in table 11. The 10×Taq Reaction Buffer used in the reactions comprises 100 nM Tris-HCl pH 8.3, 500 mM KCl and 20 mM magnesium acetate. The electrophoregram of the agarose gel analysis are shown FIG. 19. Based on visual inspection of the PCR product yield the polymerase dilutions "1:15", "1:20" and "1:25" were chosen to proceed with round two of the PCR activity determination assay. Two more intermediate dilutions ("1:17.5" and "1:22.5") were added to the analysis in round two.

TABLE 11

Reaction set-up

| Reaction Components | Volumes |
|---|---|
| 10X Taq Reaction Buffer | 5 µl |
| 10 mM dNTPs | 1 µl |
| Beta Actin Fwd Primer (20 µmol) | 1 µl |
| Beta Actin Rev Primer (20 µmol) | 1 µl |
| Human genomic DNA (50 ng/µl) | 1 µl |
| $H_2O$ | 40.8 µl |
| DNA Polymerase Dilution | 0.2 µl |

Figure 20:
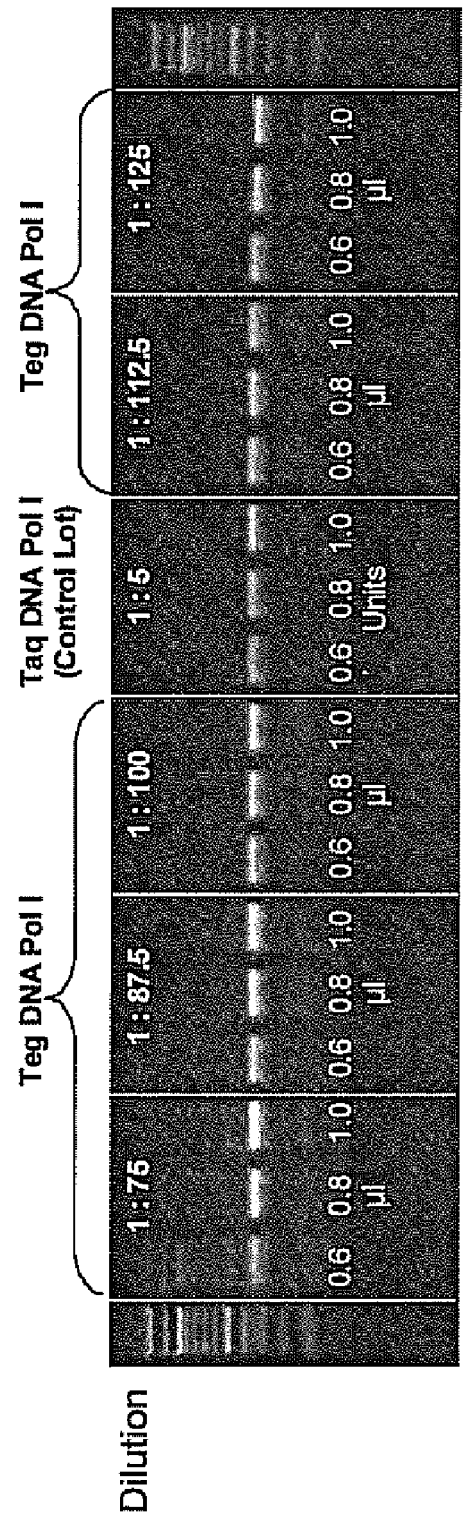
FIG. 20 provides the results of the first test in the three-step polymerase PCR-activity assay. It shows an electrophoregram comparing the amounts of endpoint PCR products generated by various dilutions of the Teg DNA polymerase concentrate in regard to the endpoint PCR products generated by a known amount of Taq DNA polymerase.

For the second round of the PCR assay, each of the chosen enzyme dilutions were further diluted 1:5 in 1×Taq Reaction Buffer to allow a more accurate dosage of small enzyme quantities into each 50 µl reaction. The Taq polymerase calibrator control was diluted accordingly in 1×Taq Reaction Buffer to a final concentration of 1 U/µl. The second round of PCR reactions were set up differently. Each polymerase dilution was represented by three test reactions. Each set of test reaction employed three different amounts of DNA polymerase ranging from 0.6 µl (0.6 U), 0.8 µl (0.8 U) to 1.0 µl (1. U), respectively. Reactions with the Taq calibrator polymerase were set up accordingly (see Table 12). The electrophoregram of the agarose gel analysis of the end point PCR products are shown FIG. 20. Based on visual inspection of the semi-quantitive PCR product yield pattern, the polymerase dilution "1:25" turned out most equivalent to the of 5U/µl Taq DNA polymerase calibrator enzyme.

TABLE 12

Reaction set-up

| Reaction Components | 0.6 µl Polymerase Dilution | 0.8 µl Polymerase Dilution | 1 µl Polymerase Dilution |
|---|---|---|---|
| 10X Taq Reaction Buffer | 5 µl | 5 µl | 5 µl |
| 10 mM dNTPs | 1 µl | 1 µl | 1 µl |
| Beta Actin Fwd Primer (20 µmol) | 1 µl | 1 µl | 1 µl |
| Beta Actin Rev Primer (20 µmol) | 1 µl | 1 µl | 1 µl |
| Human genomic DNA (50 ng/µl) | 1 µl | 1 µl | 1 µl |
| $H_2O$ | 40.4 µl | 40.2 µl | 40 µl |
| DNA Polymerase Dilution | 0.6 µl | 0.8 µl | 1.0 µl |

Figure 21:
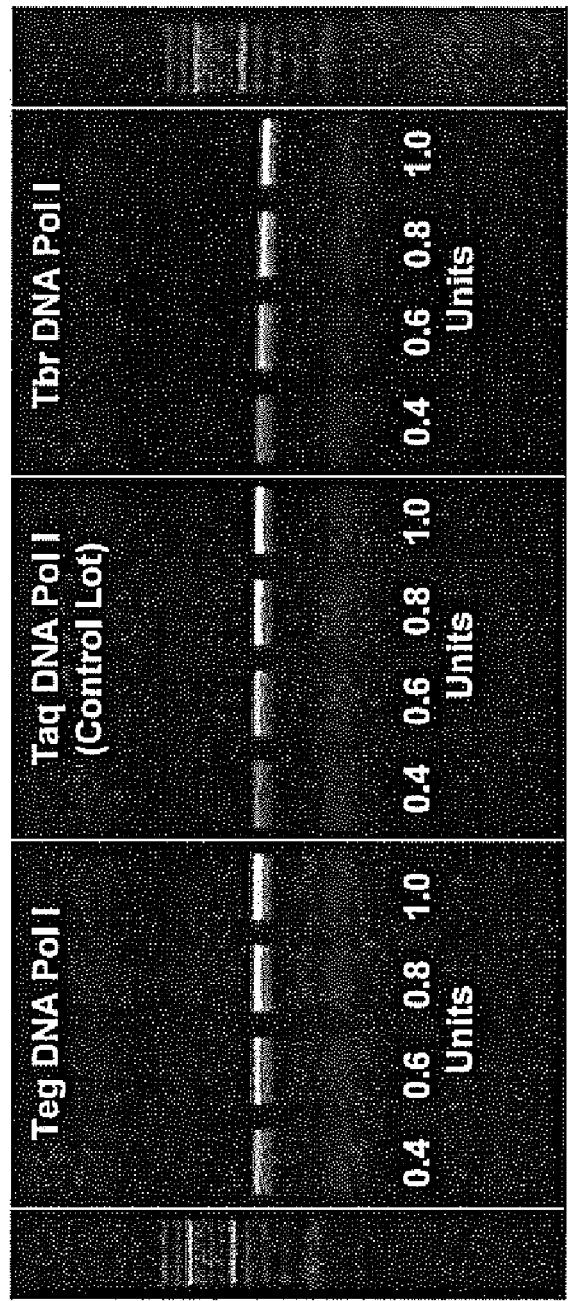
FIG. 21 provides the results of the final test in the three-step polymerase PCR-activity assay. It shows an electrophoregram comparing the amounts of endpoint PCR products generated by various dilutions of the Teg DNA polymerase concentrate in regard to the endpoint PCR products generated by a known amount of Taq DNA polymerase.

Using the established dilution factor "1:25", a volume 1 ml of adjusted Teg DNA polymerase was prepared and subjected to final activity test. As in the second round, the polymerase stock solutions for the test (at 5U/µl) were further diluted 1:5 with 1×Taq Reaction Buffer to ensure accurate liquid handling of small enzyme volumes. This time, in each test set four different polymerase volumes (0.4, 0.6, 0.8, 1.0 µl) were added into the PCR reactions providing 0.4, 0.6, 0.8, and 1.0 unit per reaction, respectively. The electrophoregram of the agarose gel analysis of the end point PCR products are shown FIG. 21.

Figure 22:
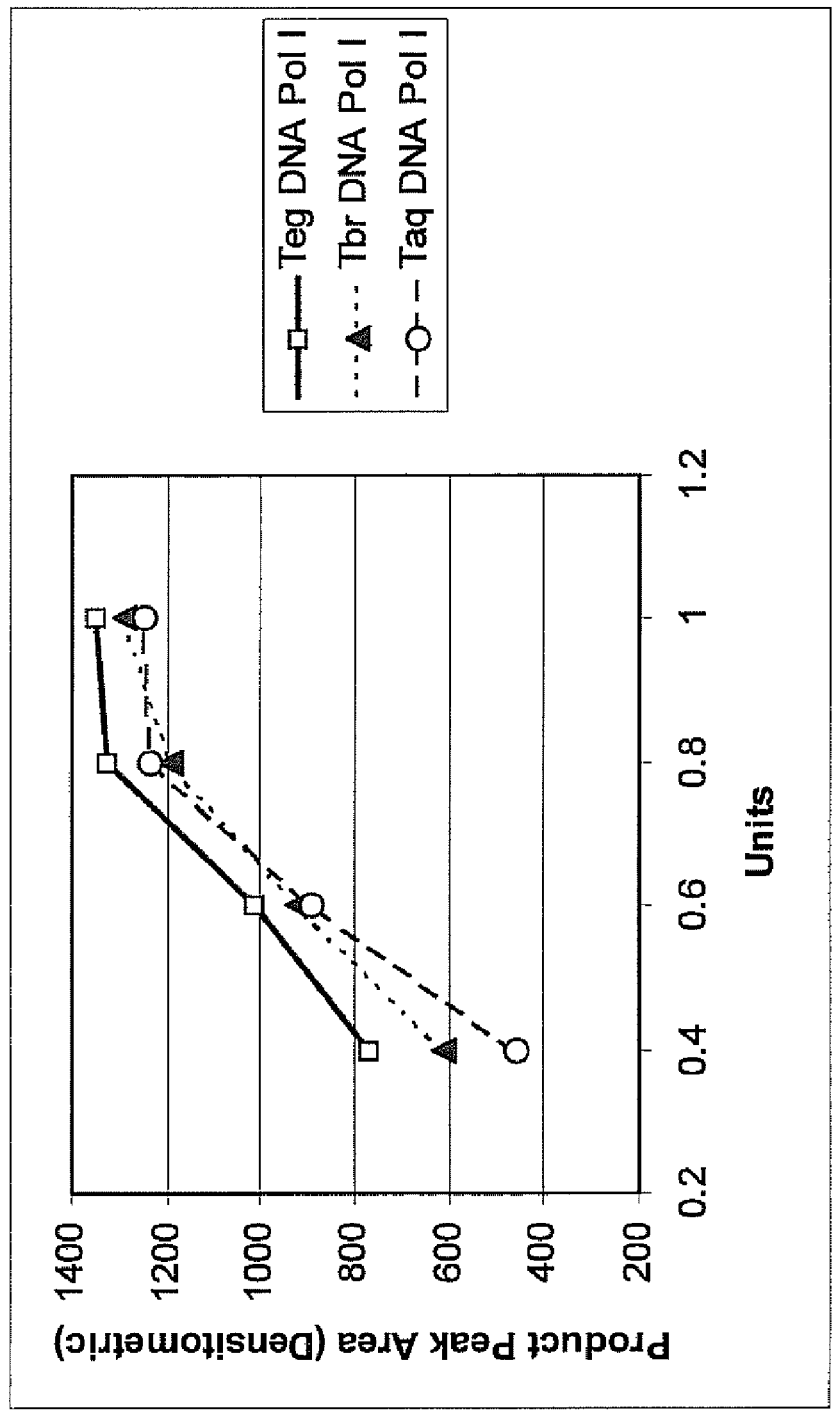
FIG. 22 provides a plot of the amount of endpoint PCR products versus the amount of polymerase units used in the PCR assay for three *Thermus* DNA polymerases: Taq DNA polymerase (5U/ul), Teg DNA polymerase (adjusted to 5U/ul) and Tbr DNA polymerase (adjusted to 5U/UI). The data points in the plot for the endpoint amounts of PCR product were calculated based on densitometric measurements of the electrophoregram in FIG. 21.

The endpoint PCR product yield was determined densitometrically using the proprietary software of the LumiImager™ gel scanner (Roche Molecular Diagnostics). The peak area of the specific PCR product band from each reaction was plotted against the amount (units or volume) of polymerase used in the corresponding reaction (see FIG. 22). The plots of three DNA polymerases compared in that experiment are shown, including the calibrator Taq DNA polymerase.

The slopes of the amplification plots of all three polymerases compared are very similar, but the plot of Teg DNA polymerase is shifted upwards. The activity concentration of the 1:25 dilution of Teg DNA polymerase turned out elevated by approximately 15% (5.8 U/µl) as a shift of the Teg curve by 0.1 U to the right would bring the Teg DNA polymerase activity plot in alignment with the Taq and Thr DNA polymerase amplification curves. The dilution of the concentrated Teg DNA polymerase was adjusted accordingly. The results of the activity assay were used to recalculate the activity concentration as well as the total activity of the concentrated Teg DNA polymerase stock solutions. The results are summarized in Table 13.

TABLE 13

Summary of the activity determination results

| | |
|---|---|
| Culture Volume | 4 L |
| Biomass | 23.7 g |
| Total Protein | 41.4 mg |
| Total Volume | 16 ml |
| Dilution Factor to 5 U/µl | 1:27.5 |
| Activity | 138 U/µl |
| Specific Activity | 53333 U/mg |
| Total Units | 2.21 Million |
| Expression Yield Activity/Biomass | 93164 U/g cells |
| Expression Yield Polymerase Activity per Culture Volume | 552000 U/L |

Example Eight

Extension Rate in M13 ssDNA Replication Assay and Thermal Stability

The extension rate of a DNA polymerase is measured by the number of bases per time interval (bases per second) the priming (+) strand is extended in 5'-3' direction. Because it is impossible to detect directly the extension of a primer by just a few bases per second, long single-stranded template molecules are used to extend the reaction (polymerization) time for measurement. In this case, a M13 phage replication assay utilizing a 7.2 kb long single-stranded M13mp18 DNA template was employed to determine extension rates of Teg-, Taq- and Tbr DNA polymerases in comparison.

The critical parameter in this assay is the first time point in a series of parallel reactions stopped at different time intervals, at which the fall-size, double-stranded replication product (7.2 kb) is detectable. The length of the template strand in bases (7200) is then divided by the minimal time interval in seconds in order to calculate the primer extension rate (bases per second).

The presence of full-length, double-stranded replication product is visualized by separation of the reaction products on an agarose gel. The full-length replication product co-migrates in the gel with a band of a reference DNA marker molecule comprising the open-circular replication form I (RF-I) of the M13 bacteriophage (M13mp18 RF-I DNA, New England Biolabs). The single-stranded M13mp18 template DNA migrates fastest in front of all reaction products. Intermediate primer extension products, partially double-stranded, do not form discrete bands, but migrate as a diffuse cloud anywhere between the band of the single-stranded template and the band of full-size double-stranded replication product (see FIG. 23).

All primer extension reactions were carried out in a 20 µl volume at 60° C. The reactions contained one unit of either Teg-, Taq-, or Thr DNA polymerase, 250 µmol of each dNTP, 375 ng ssM13mp18 (0.15 pmol) primed with 0.3 pmol M13 Reverse Primer (−48) 24mer (SEQ ID NO: 41; New England Biolabs) and a 1× reaction buffer comprising 30 mM Bicine, X mM Tris pH 8.7, 50 mM KCl and 2.0 mM magnesium acetate. The single-stranded template DNA was primed in a separate hybridization reaction prior to the replications assay. Primer hybridization was done for 10 minutes at 75° C. followed by 30 minutes incubation at room temperature.

Each primer extension reaction was started at a fixed time point by addition of the dNTP substrates and stopped after the desired time interval elapsed by the addition of EDTA to a final concentration of 10 mM. A complete set of primer extension reactions for one DNA polymerase comprised nine parallel reactions covering the reaction time intervals of 30, 60, 90, 120, 180, 210, 240, 270 and 300 seconds.

Figure 23:
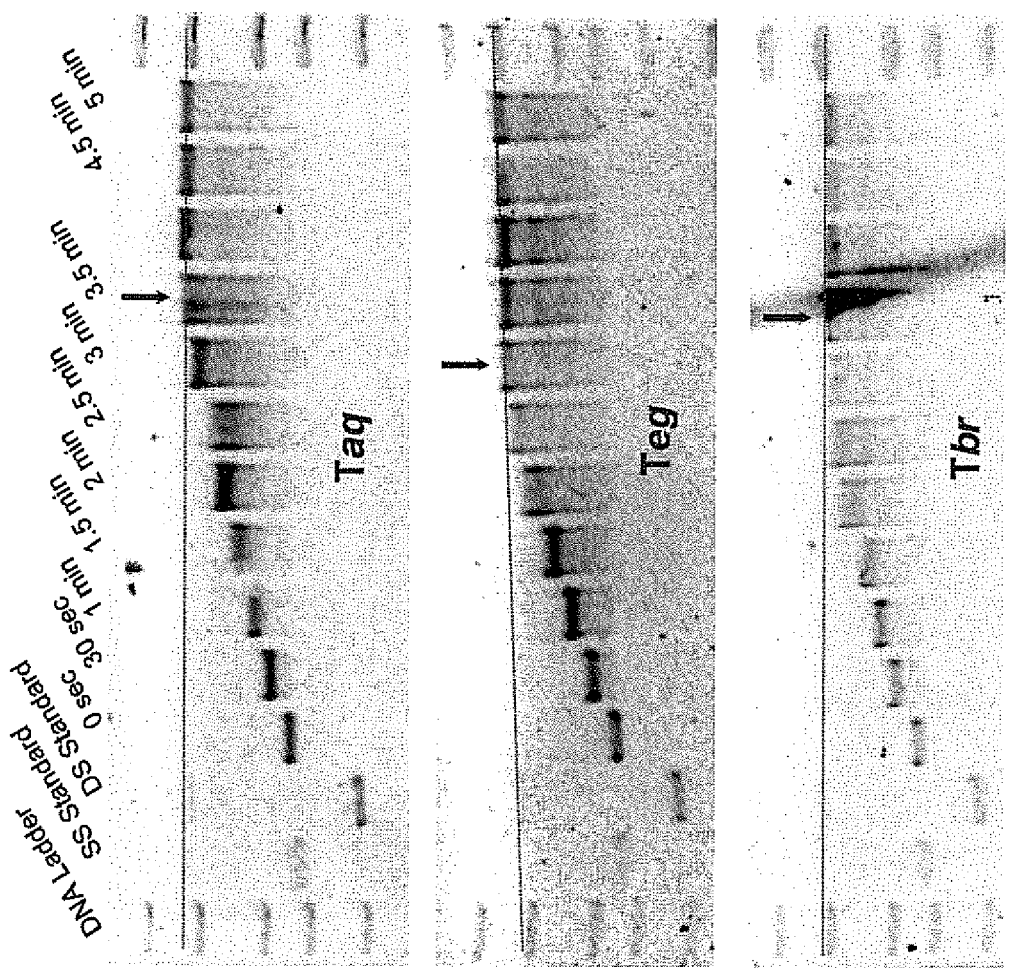
FIG. 23 provides an electrophoregram of DNA polymerase primer extension rate assay comparing Teg-, Taq- and Thr DNA polymerase expressed and purified under the same conditions.

The results of the primer extension rate assay for all three *Thermus* DNA polymerases are visualized on the electrophoregram in FIG. 23. Two minutes and 30 seconds, three minutes and three minutes and 30 seconds are the first time points at which the full-length, 7.2 kb replication product becomes detectable with either Teg-, Taq- or Thr DNA polymerase, respectively. That translates into primer extension rates of 40 bases/see, 34.3 bases/sec and 40 bases/sec for Teg-, Taq- and Thr DNA polymerase respectively. These rates were reproduced with several different purification lots of Teg- and Taq DNA polymerase.

The extension rate of Teg DNA polymerase is 5 bases/sec faster than the rate of Taq DNA polymerase. This difference may not seem significant, but it lead to time gap of 30 seconds between the two polymerases in completing the replication of the 7.2 kb template DNA. Amplifying the same DNA template in a polymerase chain reaction (by far the most important application of thermostable DNA polymerases) comprising 40 cycles, this small difference would amount to 20 minutes total time difference over the course of the experiment. For people skilled in the art of this invention, fast PCR cycling times is one of the most desired application features of thermostable DNA polymerases.

Example Nine

Thermostability of Teg DNA Polymerase in a Real-Time PCR Application in Regard to the Stability of Taq- and Tbr DNA Polymerase Thermostability is one of the most critical performance features of thermostable DNA polymerases. The origin from a thermophilic microorganism provides no guarantee for sufficient stability of a DNA polymerase against irreversible heat inactivation in PCR or thermocycle sequencing reactions. Numerous DNA polymerases have been isolated from thermophilic bacteria in search for novel functionalities or better performance features, which insufficient thermostability limited their utility for PCR. Examples of such enzymes are the type-I DNA polymerases from *Geobacillus staerothermophilus, Thermoplasma acidophilum* and *Aquifex* spec. Another example to be added to that list will be demonstrated here by the Tbr DNA polymerase.

There is no standard test to determine the thermostability of a DNA polymerase. The actual stability can vary widely depending on the reaction conditions used in the test. A pure, single enzyme in a diluted aqueous buffer has lower thermostability than in the presence of stabilizing co-solvents, substrates and co-factors. Pure Taq DNA polymerase has half life less than 5 minutes when exposed to 95° C. Under "normal" PCR-reaction conditions, dNTPs, the primed template DNA substrate and magnesium ions bound to the polymerase exert a stabilizing effect. In praxis, only the thermostability under PCR conditions is relevant for people skilled in the art.

We chose a real-time PCR assay to challenge the thermostability of Teg DNA polymerase in comparison to Taq- and Thr DNA polymerase. The challenge consisted of pre-incubation of the PCR reaction mixture at 95° C. up to 15 minutes before starting the actual PCR cycling program. Real-time PCR allows the exact relative quantification in real time of the PCR product generated. The threshold cycle number determined in real-time PCR assays ($C_T$) is a indirect measure for the amount of PCR product amplified (if the input amount of template DNA is kept constant). The threshold cycle is the first cycle in the PCR experiment at which the fluorescence emitted from the PCR product amplified exceeds the level of background fluorescence. The amount of PCR product, in tuna, is a direct measure of the amount of active DNA polymerase available in the reaction, if all other factors are kept constant among all test reactions. Therefore, all reactions were set-up from a single master mix to ensure that the only variable allowed in the experiment was the pre-amplification exposure tine at 95° C. ranging from 5 to 10 minutes.

Figure 24:
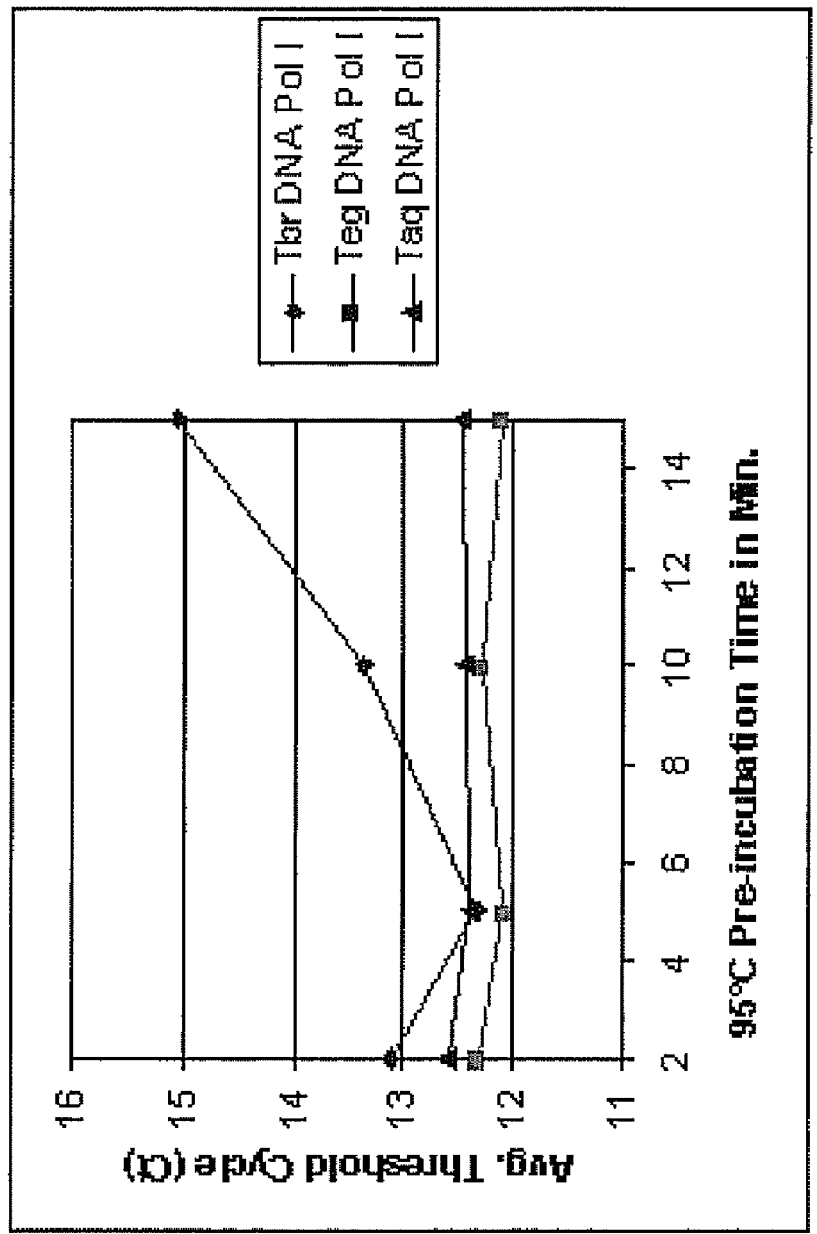
FIG. 24 provides heat stability data comparison between Teg, Taq, and Thr using real-time PCR.

FIG. 25 shows exact reaction conditions and the amplification plots of the real-time PCR experiments with Teg-, Taq- and Tbr DNA polymerase. Even 15 minutes exposure to 95° C. had no measurable negative effect on the PCR performance, e.g. activity of Teg and Taq DNA polymerase. The Thr DNA polymerase, instead, was negatively affected. The plot in FIG. 24 shows Ct value versus exposure time at 95° C. a 2.5 cycle shift upwards.

Example 10

DNA Synthesis Fidelity Teg DNA Polymerase

The synthesis fidelity of a DNA polymerase is its ability to discriminate against the incorporation of a "wrong" nucleotide at the 3'-terminus of the priming strand. A "wrong" nucleotide refers to a nucleotide with a base that can not engage in Watson/Crick-type hydrogen bonding with the opposing base in the template strand. Thermodynamic restrictions for conformational changes in the polymerase active site provide the underlying mechanism for "wrong" base discrimination. The conformational restrictions are imposed by DNA helix distortions of a "Non-Watson-Crick" base pair.

In scientific literature, fidelity is often confused with the reverse numeric value of the error rate. The error rate of a polymerase represents a complex parameter, which depends on the outcome of three different processes that all occur simultaneously during replication: incorporation of a mismatched base, excision of a mismatched base (e.g. exonuclease proof-reading) or extension of a mismatched base. Fidelity controls only the outcome of the first process. It takes the concerted action of mismatched base incorporation and mismatch extension to permanently fix a polymerase copy error in the replication product.

Each of the 12 possible base mismatch combinations has specific helix distortion characteristics. Therefore, the synthesis fidelity of a given polymerase comprises the average of 12 individual mismatch base pair fidelities. A G/T base pair causes the lowest distortion in a DNA double helix compared to a standard Watson/Crick base pair. A G/G base pair is so distorted that it is almost impossible for a DNA polymerase to incorporate it into the helix of a nascent DNA chain during replication. Therefore, discriminations against a G/T base pair or a G/G base pair mark the lowest and highest fidelity extremes, respectively, among a panel of 12 theoretically possible mismatch base pairs. The generic fidelity of a DNA polymerase can be expressed as the average of the two extreme base pair fidelities.

The G/T- and G/G mismatch fidelities of Teg- and Taq DNA polymerase were determined using a steady-state kinetics dNTP incorporation assay developed by Echols and Goodman for the *E. coli* DNA polymerase III. (Echols and Goodman, "Fidelity Mechanisms in DNA Replication," Annual Review of Biochemistry, 60:477-511, 1991, herein incorporated by reference). The same assay was successfully used by the authors of the paper to determine the fidelity of Taq DNA polymerase.

Figure 26:
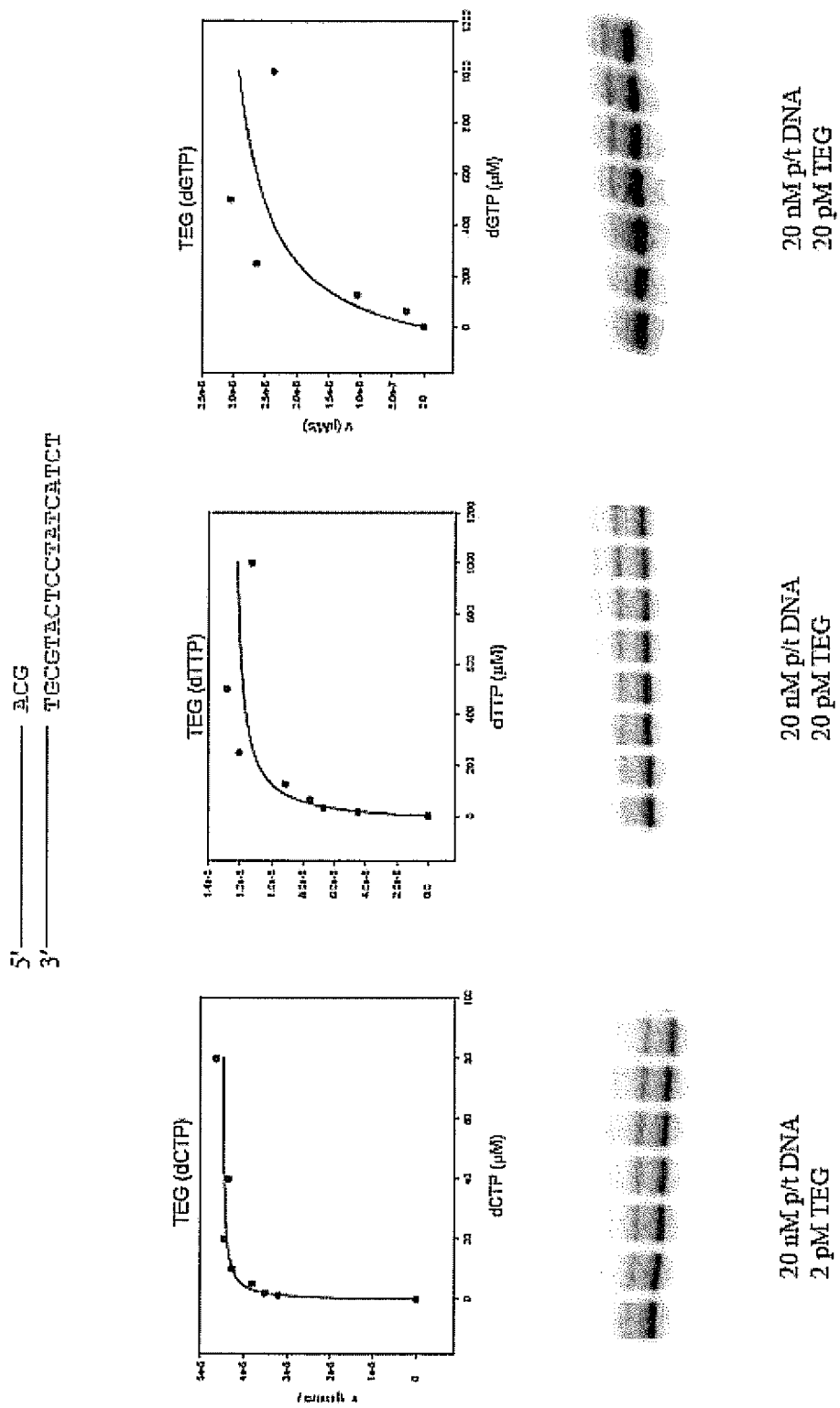
FIG. 26 shows the fidelity of Teg DNA polymerase on a G-T and G-G base pair mismatch.

The "Goodman" assay employs a partially double-stranded DNA template molecule with a recessed 3'-terminus on the priming (+) strand shown in FIG. 26. The 5'-terminus of the priming strand is labeled with $^{32}P$ for detection and quantification of the primer extension product. A "G" forms the template base adjacent to the 3'-terminus of the priming strand that needs to be matched by the polymerase with the incoming dNTP substrate. The reaction product in all assay reactions is a one-base extended primer strand (n+1), which is separated from the non-extended DNA template molecule by PAAGE under denaturing conditions.

Each polymerase was evaluated for its ability to generate a T/G, and G/G mismatch base pairing at position n+1 of the 3'-recessed priming strand. Two sets of reactions were run for each of the two base mismatch pairs. In the first set of reactions increasing concentrations of the matching nucleotide dCTP were applied. In the second set increasing concentrations of a mismatching nucleotide were used (either dGTP or dTTP). The concentrations of all other reactants were kept constant for all reactions. All reactions were carried out in 20 µl containing 30 mM Bicine, 59 mM Tris pH 8.7, 50 mM KCl, 2 mM magnesium acetate at 60° C. over 8 minutes.

The reactions were stopped by addition of an EDTA/formamide-containing sample loading buffer. All reaction products were separated side-by-side on a 20%, TBE-buffered PAAG under denaturing conditions (8M urea). The "n+1" primer extension products in the gel were detected and quantified densitometrically with a Phospholinager (Amersham).

Figure 27:
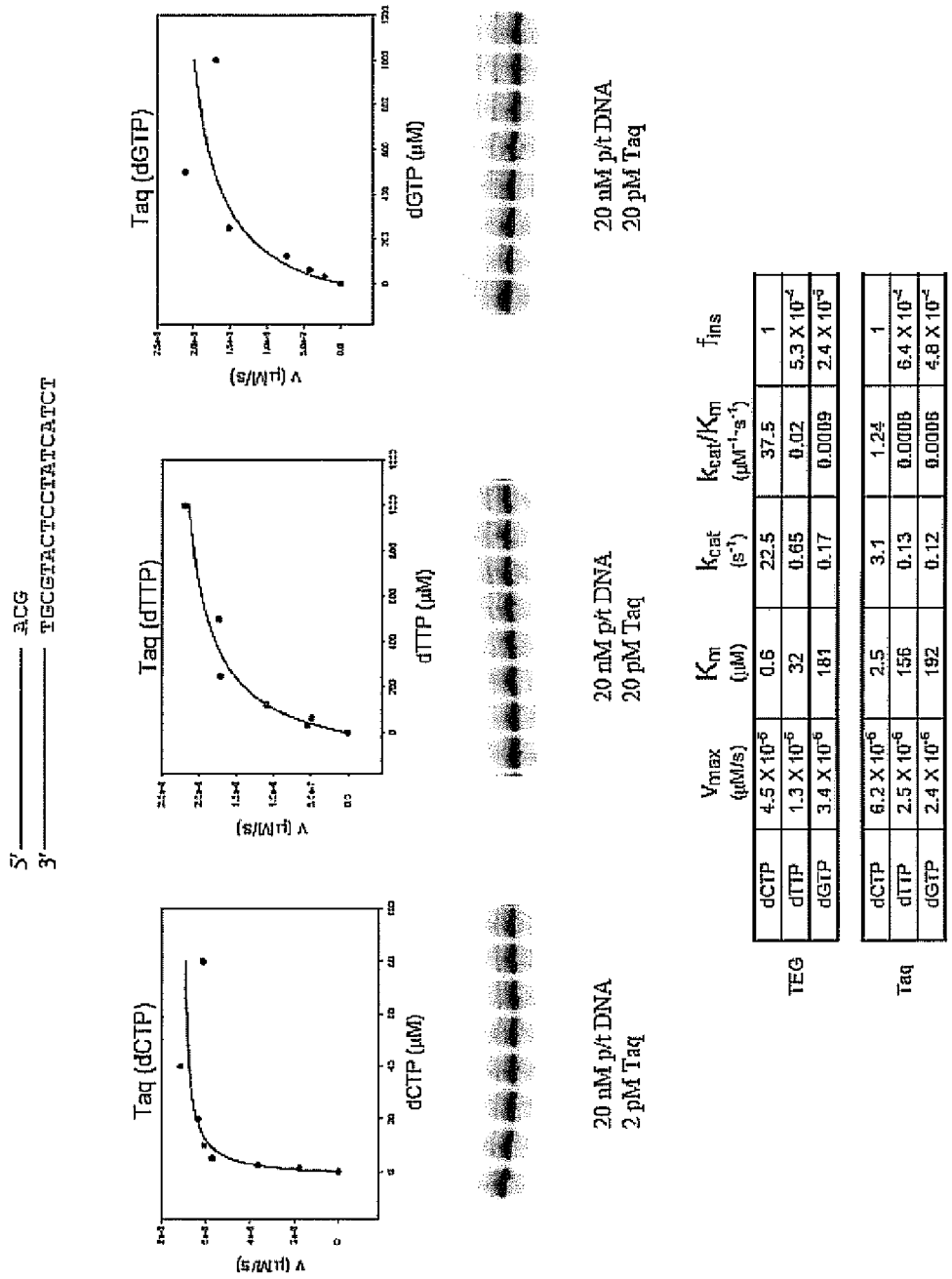
FIG. 27 shows the fidelity of Taq DNA polymerase on G-T and G-G base pair mismatch.
Figure 28:
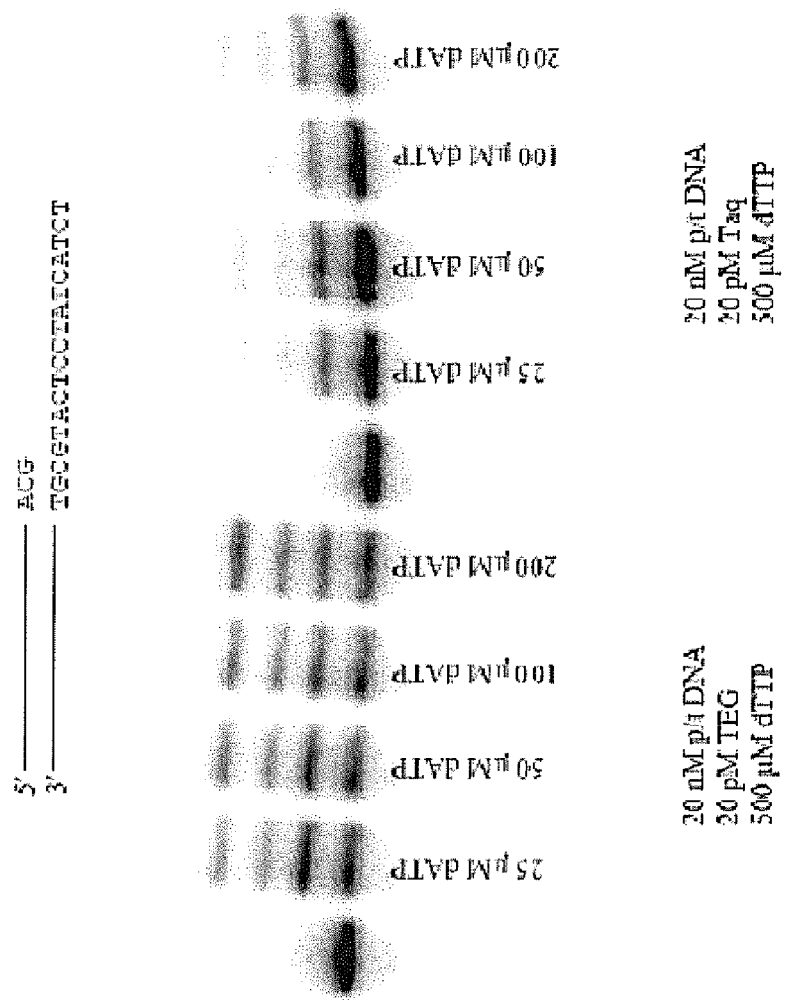
FIG. 28 provides mismatch extension data for Teg and Taq.
Figure 29:
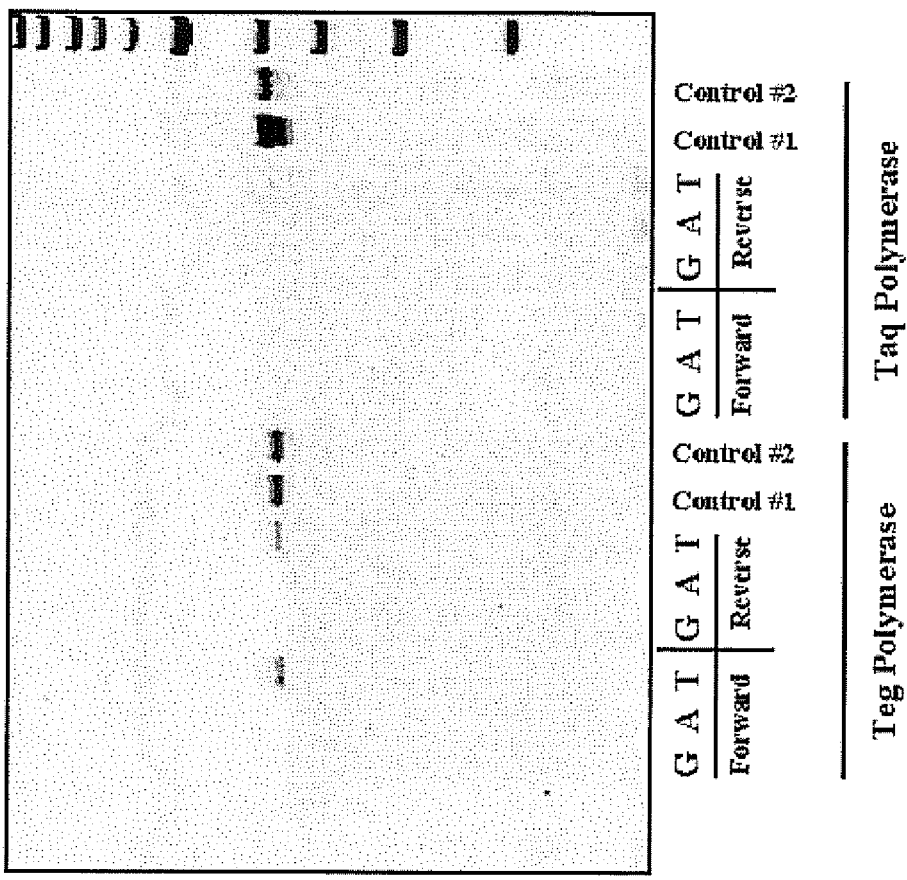
FIG. 29 provides PCR amplification data for mismatched primer combination using Teg and Taq.

FIGS. 26 and 27 summarize the results of the kinetic fidelity analysis for Teg- (FIG. 26) and Taq DNA polymerase (FIG. 27). The pronounced lower band on each electrophoregram represents the labeled, non-extended DNA template, which was kept in all reactions in a 10-fold molar excess over the polymerase enzyme for steady-state kinetics. The faint band above the template band represents the n+1 primer extension product, which was quantified. In table 15 summarizes the fidelity data of Teg- and Tag DNA polymerase.

TABLE 15

Misinsertion frequency ($f_{ins}$) and mismatch fidelity of Teg- and Taq DNA polymerase

| DNA Polymerase | G/T Misinsertion Frequency ($f_{ins}$) | G/T Mismatch Fidelity | G/G Misinsertion Frequency ($f_{ins}$) | G/G Mismatch Fidelity | Average Fidelity |
|---|---|---|---|---|---|
| Teg | $5.3 \times 10^{-4}$ | $1.9 \times 10^3$ | $2.4 \times 10^{-5}$ | $4.2 \times 10^4$ | $2.2 \times 10^4$ |
| Taq | $6.4 \times 10^{-4}$ | $1.6 \times 10^3$ | $4.8 \times 10^{-4}$ | $2.1 \times 10^3$ | $1.8 \times 10^3$ |

While for the G/T mismatch the fidelity of Teg DNA polymerase is only slightly better than the fidelity of Taq, Teg shows a more than 1000-fold higher fidelity for the G/G mismatch. This represents a significant benefit of Teg DNA polymerase over Taq for all applications, more so, because there is no proof-reading exonuclease activity involved.

The invention claimed is:

1. An isolated DNA polymerase, wherein the DNA polymerase comprises an amino acid sequence selected from the group consisting of: SEQ ID NO: 6 and SEQ ID NO: 44.

2. An isolated nucleic acid sequence encoding the amino acid sequence selected from the group consisting of: SEQ ID NO: 6 and SEQ ID NO: 44.

3. A vector comprising the nucleic acid sequence of claim 2.

4. An isolated nucleic acid sequence comprising a sequence selected from the group consisting of: SEQ ID NO: 5 and SEQ ID NO: 43.

5. A vector comprising the nucleic acid sequence of claim 4.

6. The vector of claim 3, wherein the vector further comprises:
   a) a promoter element operably linked to the nucleic acid sequence of claim 2;
   b) a ribosome binding site;
   c) a selectable metabolic marker gene;

d) an origin of replication functional in a host cell and; optionally, e) 3'-non-translated sequence elements enhancing the translation of the nucleic acid sequence transcript encoding the DNA polymerase.

7. The vector of claim 5, wherein the vector further comprises:

a) a promoter element operably linked to the nucleic acid sequence of claim 4;

b) a ribosome binding site;

c) a selectable metabolic marker gene;

d) an origin of replication functional in a host cell and; optionally, e) 3'-non-translated sequence elements enhancing the translation of the nucleic acid sequence transcript encoding the DNA polymerase.

8. A nucleic acid replication kit comprising a DNA polymerase according to claim 1.

9. The nucleic acid replication kit of claim 8, further comprising a reaction buffer.

10. The nucleic acid replication kit of claim 8, further comprising nucleotides.

11. The nucleic acid replication kit of claim 9, further comprising nucleotides.

12. A nucleic acid replication kit according to claim 8, wherein the kit is selected from the group consisting of a DNA sequencing kit and a DNA amplification kit.

* * * * *